United States Patent

Goto et al.

[11] Patent Number: 5,589,439
[45] Date of Patent: Dec. 31, 1996

[54] TETRAZOLINONE DERIVATIVES

[75] Inventors: Toshio Goto, Shimotusga-gun; Koichi Moriya, Oaza; Fritz Maurer, Tochigi; Seishi Ito, Oyama; Katsuaki Wada, Tochigi; Kazuhiro Ukawa, Oyama; Ryo Watanabe, Tochigi; Asami Ito, Tochigi; Natsuko Minegishi, Tochigi, all of Japan

[73] Assignee: Nihon Bayer Agrochem K.K., Tokyo, Japan

[21] Appl. No.: 508,776

[22] Filed: Jul. 28, 1995

[30] Foreign Application Priority Data

Aug. 5, 1994 [JP] Japan .................. 6-202919
Mar. 3, 1995 [JP] Japan .................. 7-068837

[51] Int. Cl.$^6$ .......... A01N 43/82; A01N 43/824; A01N 43/828; A01N 43/832; C07D 409/04; C07D 407/04; C07D 405/04; C07D 403/04; A01N 43/836; A01N 43/713; C07D 417/04; C07D 413/04

[52] U.S. Cl. .......... 504/261; 548/251; 548/196; 548/214; 548/233; 548/245; 548/125; 548/133; 548/143; 548/127; 548/128; 548/135; 548/140; 504/262; 504/265; 504/263; 504/266; 504/269; 504/270; 504/271; 504/273; 504/282; 504/277; 504/283; 504/289; 504/294

[58] Field of Search .................. 548/251, 196, 548/214, 233, 245, 125, 133, 143, 127, 128, 135, 140; 504/261

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,019,152 | 5/1991 | Covey et al. | 71/92 |
| 5,342,954 | 8/1994 | Goto et al. | 548/251 |
| 5,344,814 | 9/1994 | Goto et al. | 504/261 |
| 5,347,009 | 9/1994 | Goto et al. | 548/251 |
| 5,347,010 | 9/1994 | Goto et al. | 548/251 |
| 5,362,704 | 11/1994 | Goto et al. | 504/134 |
| 5,502,204 | 3/1996 | Yanagi et al. | 548/251 |

FOREIGN PATENT DOCUMENTS 0578090 1/1994 European Pat. Off. .
0643049 3/1995 European Pat. Off. .

*Primary Examiner*—Johann Richter
*Assistant Examiner*—Laura R. Cross
*Attorney, Agent, or Firm*—Sprung Horn Kramer & Woods

[57] ABSTRACT

Herbicidal novel tetrazolinone derivatives of the formula:

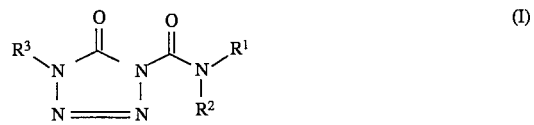

wherein $R^1$ is alkyl, haloalkyl, cycloalkyl, alkenyl, haloalkenyl, alkynyl, alkoxy or phenyl which is optionally substituted, and $R^2$ is alkyl, haloalkyl, cycloalkyl, alkenyl, haloalkenyl, alkynyl, alkoxy or phenyl which is optionally substituted, or $R^1$ and $R^2$ form, together with the nitrogen atom to which $R^1$ and $R^2$ are bonded, a 5- or 6-membered heterocyclic ring, optionally fused to a carbocyclic ring optionally and independently substituted by $C_{1-4}$ alkyl, and $R^3$ is a 5-membered heterocyclic radical containing at least one hereto atom selected from the group consisting of nitrogen, oxygen, and sulfur, optionally substituted by at least one substituent selected from the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkylsulfonyl and $C_{3-8}$ cycloalkyl, processes for their preparation and novel intermediates therefor.

12 Claims, No Drawings

TETRAZOLINONE DERIVATIVES

The present invention relates to tetrazolinone derivatives, to processes for their preparation and to their use as herbicides, as well as to intermediates therefor.

It has already been known that tetrazolinone derivatives are useful as herbicides (see U.S. Pat. Nos. 4,618,365; 4,826,529; 4,830,661; 4,956,469; 5,003,075; 5,019,152; 5,342,954; 5,344,814; 5,347,009, 5,347,010; and 5,362,704).

There have been found novel tetrazolinone derivatives of the formula

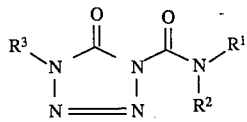

(I)

wherein $R^1$ represents alkyl, haloalkyl, cycloalkyl, alkenyl, haloalkenyl, alkynyl, alkoxy or phenyl which may be substituted, $R^2$ represents alkyl, haloalkyl, cycloalkyl, alkenyl, haloalkenyl, alkynyl, alkoxy or phenyl which may be substituted, or $R^1$ and $R^2$ may form, together with the nitrogen atom to which $R^1$ and $R^2$ are bonded, a 5- or 6-membered heterocyclic ring, and said heterocyclic ring may be fused to a carbocyclic ring and/or may be substituted by $C_{1-4}$ alkyl, and $R^3$ represents a 5-membered heterocyclic ring containing at least one hetero atom selected from the group consisting of nitrogen, oxygen and sulfur, and said 5-membered heterocyclic ring is optionally substituted by at least one substituent selected from the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkyl-sulfonyl and $C_{3-8}$ cycloalkyl.

The novel tetrazolinone derivatives of the formula (I) are obtained when (a) compounds of the formula

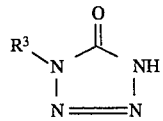

(II)

wherein $R^3$ has the above mentioned meanings, are reacted with compounds of the formula

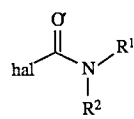

(III)

wherein $R^1$ and $R^2$ have the above mentioned meanings, and hal represents a releasable group such as chlorine or bromine, in the presence of an acid-binder, and in the presence of inert solvents, or (b) when $R^3$ represents a 5-membered heterocyclic ring including a group of the

so that $R^3$ is

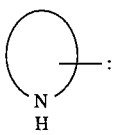

compounds of the formula

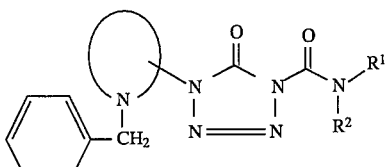

(IV)

wherein $R^1$ and $R^2$ have the same meanings as defined above, are reduced, if appropriate in the presence of catalysts, and in the presence of inert solvents.

The novel tetrazolinone derivatives of the formula (I) exhibit powerful herbicidal properties.

Surprisingly, the tetrazolinone derivatives of the formula (I), according to the present invention, exhibit substantially higher herbicidal activities than those known from the prior art, for instance, the aforementioned U.S. Pat. Nos. 4,618,365; 4,826,529; 4,830,661; 4,956,469; 5,003,075; 5,019,152; 5,342,954; 5,344,814; 5,347,009, 5,347,010; and 5,362,704.

In the compounds of the formula (I) according to the invention, and the respective general formulae representing their intermediates employed for the production of compounds of the formula (I), each of the halogen atoms may be fluorine, chlorine, bromine or iodine, preferably chlorine or fluorine.

Alkyl represents, for example, methyl, ethyl, propyl, isopropyl, (n-iso-, sec-, tert-)butyl, (n-iso-, sec-, tert-, neo-) pentyl or (n-iso-, sec-, tert-, neo-)hexyl.

Haloalkyl represents the above mentioned alkyl groups which are substituted with the same or different halogen atoms, for example, trifluoromethyl, 2-chloroethyl and 2,2,2-trifluoroethyl.

Cycloalkyl represents, for example, cyclopropyl, cyclobutyl, cyclopentyl, cyclohexyl, cycloheptyl or cyclooctyl.

Alkenyl represents, for example, vinyl, allyl, isopropenyl, 1-methyl-2-propenyl, 2-methyl-2-propenyl, (2- or 3-)butenyl or (2-, 3- or 4-)pentenyl.

Haloalkenyl represents the above mentioned alkenyl group which are substituted with the same or different halogen atoms, and for example, 2-chloro-2-propenyl.

Alkynyl represents, for example, propargyl.

Alkoxy represents, for example, methoxy, ethoxy, propoxy, isopropoxy, (n-iso-, sec-, tert-)butoxy, (n-iso-, sec-, tert-, neo-)pentyloxy or (n-iso-, sec-, tert-, neo- )hexyloxy.

The phenyl may optionally be substituted by at least one substituent independently selected from the group consisting of halogen, cyano, nitro, alkyl, haloalkyl, alkoxy, haloalkoxy and alkylthio.

The 5- or 6-membered heterocyclic ring represents those which contain, as a hetero-atom, at least one nitrogen and may further contain at least one hetero-atom selected from the group consisting of nitrogen, oxygen and sulfur. Said heterocyclic group may be fused to a carbocyclic ring and/or substituted by one or more $C_{1-4}$ alkyl radicals, as for example, pyrrolidinyl, 2,5-dimethyl-pyrrolidinyl, pyrrolinyl, 2,5-dimethyl-3-pyrrolinyl, imidazolidinyl, pyrazolidinyl, pyrazolinyl, 5-methyl-2-pyrazolinyl, piperidyl, 2-methylpiperidyl, 2,6-dimethylpiperidyl, piperazinyl, indolinyl, morpholinyl, 1,2,3,4-tetrahydroquinolyl, 2-methyl-1,2,3,4-tetrahydroquinolyl, perhydroindol-1-yl and perhydroquinotin-1-yl.

The 5-membered heterocyclic ring has at least one hetero atom selected from the group consisting of nitrogen, oxygen and sulfur, for example, furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl and 1,2,4-triazolyl. The 5-membered heterocyclic ring may be substituted by at least one substituent independently selected from halogen (fluorine, chlorine, bromine), alkyl (methyl, ethyl, isopropyl, propyl, (n-iso-, sec-, tert-)butyl), cycloalkyl (cyclopropyl, cyclohexyl, cyclopentyl), alkoxy (methoxy, ethoxy, isopropoxy, propoxy), haloalkyl (trifluoromethyl), haloalkoxy(fluoromethoxy), alkylthio (methylthio, ethylthio, propylthio, isopropylthio, (n-iso-, sec-, tert-)butylthio), alkyl-sulfonyl(methyl-sulfonyl, ethyl-sulfonyl, n-propyl-sulfonyl), benzyl, phenyl and halogen substituted phenyl.

Among the tetrazolinone derivatives according to the invention, of the formula (I), preferred compounds are those in which $R^1$ represents $C_{1-6}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynyl, $C_{1-6}$ alkoxy or phenyl, and $R^2$ represents $C_{1-6}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynyl, $C_{1-6}$ alkoxy or phenyl, or $R^1$ and $R^2$ may form, together with the nitrogen atom to which $R^1$ and $R^2$ are bonded, a 5- or 6-membered heterocyclic ring, which optionally can contain a further hetero atom selected from the group consisting of nitrogen, oxygen and sulfur and said heterocyclic ring, may be fused to cyclohexyl or phenyl and/or may be substituted by one or more methyl radicals, $R^3$ represents a 5-membered heterocyclic ring selected from the group consisting of furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxdiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl and 1,2,4-triazolyl, said 5-membered heterocyclic ring optionally being substituted by at least one substituent independently selected from the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkyl-sulfonyl and $C_{3-8}$ cycloalkyl.

Particularly preferred tetrazolinone derivatives of the formula (I) are those in which $R^1$ represents $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl, $C_{1-4}$ alkoxy or phenyl, and $R^2$ represents $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl, $C_{1-4}$ alkoxy or phenyl, or $R^1$ and $R^2$ form, together with the nitrogen atom to which $R^1$ and $R^2$ are bonded, pyrrolidin-1-yl, 2,5-dimethylpyrrolidin-1-yl, pyrrolin-1-yl, 2,5-dimethyl-3-pyrrolinyl, 5-methyl-2-pyrazolin-1-yl, piperidino, 2-methylpiperidino, 2,6-dimethylpiperidino, piperazin-1-yl, morpholino, 1,2,3,4-tetrahydro-quinolin-1-yl, 2-methyl-1,2,3,4-tetrahydroquinolin-1-yl, perhydroindol-1-yl or perhydroquinolin-1-yl.

$R^3$ represents a 5-membered heterocyclic ring selected from the group consisting of furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxdiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl and 1,2,4-triazolyl, and said 5-membered heterocyclic ring may be substituted by at least one substituent independently selected from the group consisting of fluorine, chlorine, bromine, methyl, ethyl, isopropyl, propyl, (n-iso-, sec-, tert-)butyl, cyclopropyl, cyclohexyl, cyclopentyl, methoxy, ethoxy, isopropoxy, propoxy, trifluoromethyl, fluoromethoxy, methylthio, ethylthio, propylthio, isopropylthio, (n-iso-, sec-, tert-)butylthio, methyl-sulfonyl, ethyl-sulfonyl, n-propylsulfonyl, benzyl, phenyl and chlorophenyl.

Specifically, compounds according to the invention wherein $R^1$ and $R^2$ each represent an independent group are shown hereinbelow in Table 1, and compounds wherein $R^1$ and $R^2$ form, together with the nitrogen to which $R^1$ and $R^2$ are bonded, a heterocyclic ring are shown in Table 2 hereinbelow. In Tables 1, 2 and 3, hereinbelow,

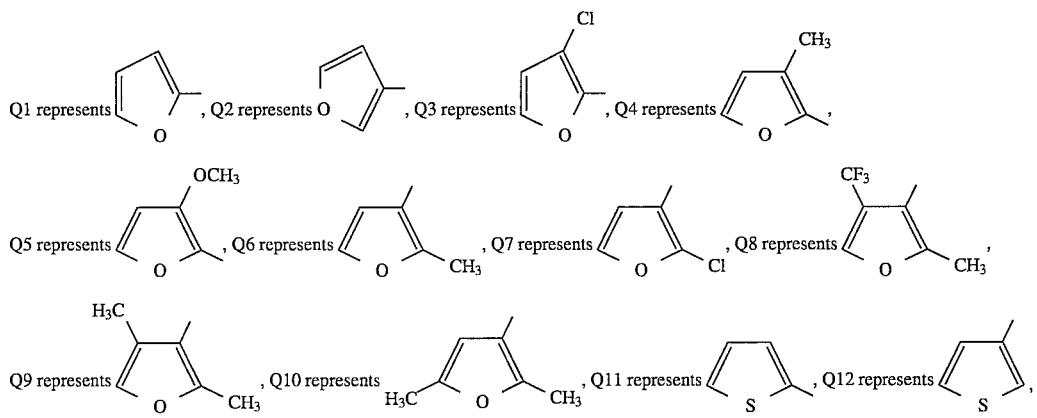

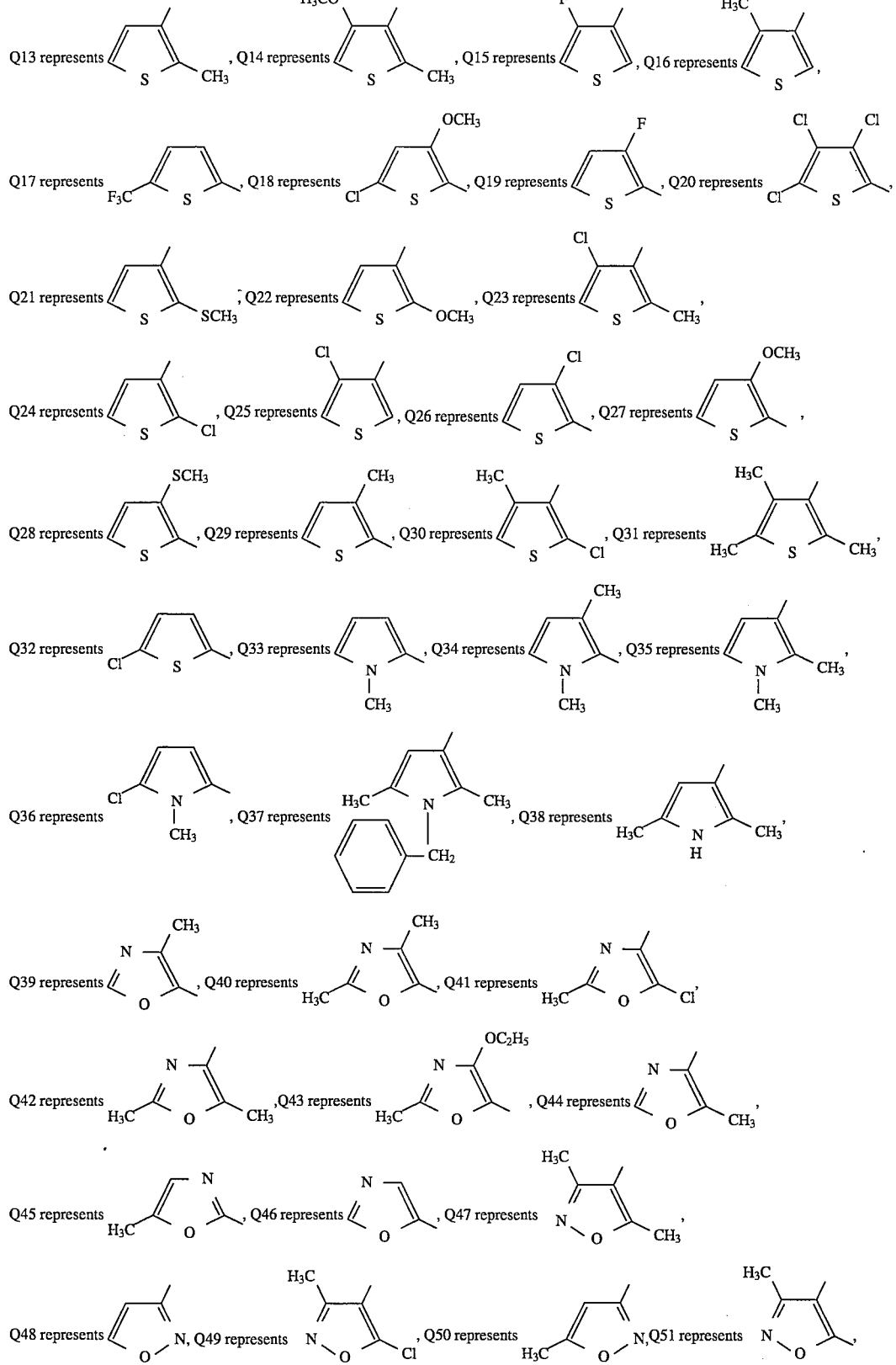

-continued
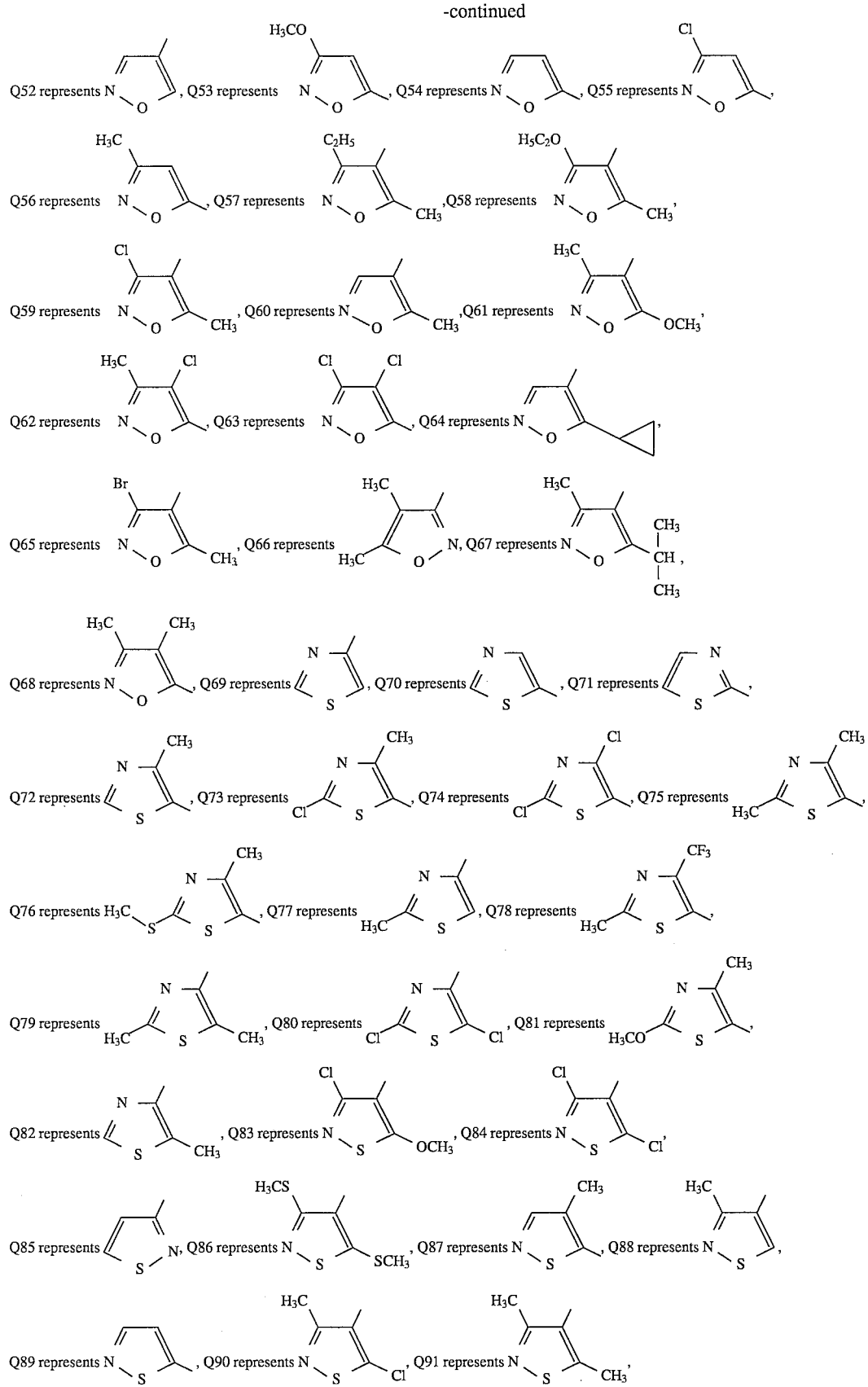

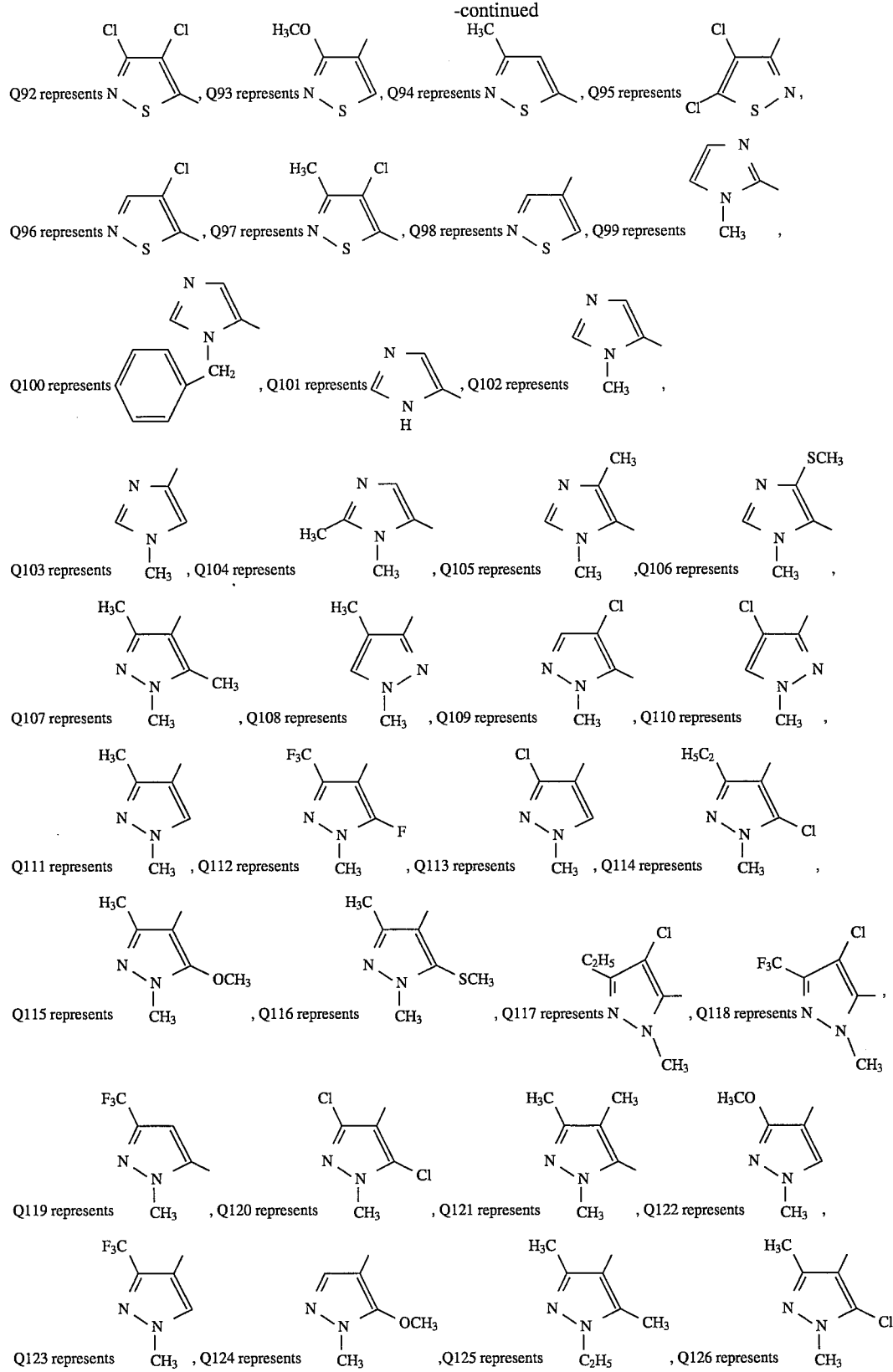

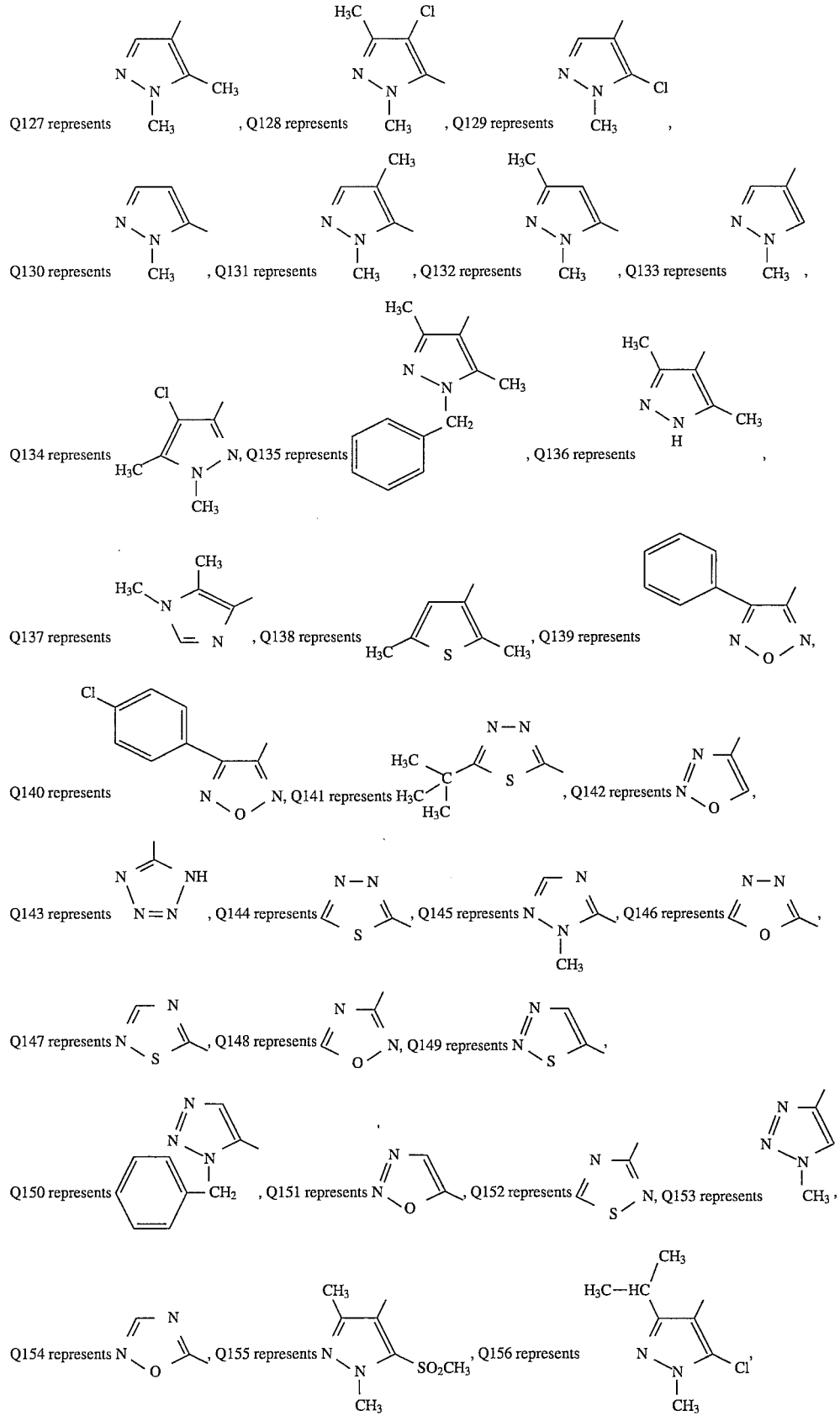

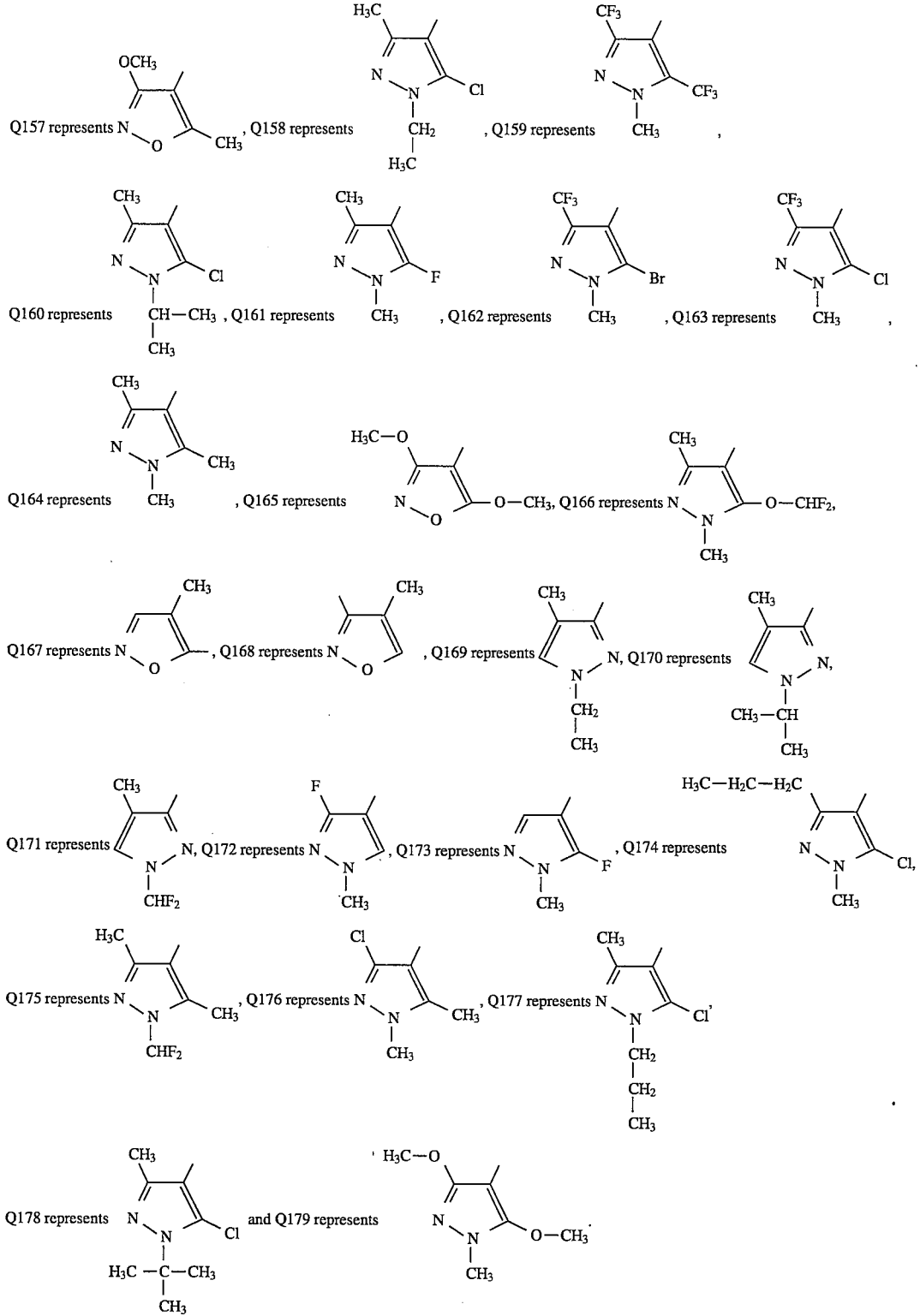

TABLE 1

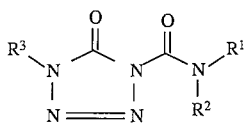

| R³ | R¹ | R² |
| --- | --- | --- |
| Q1 | ethyl | ethyl |
| Q1 | ethyl | isopropyl |
| Q1 | isopropyl | phenyl |
| Q2 | ethyl | ethyl |
| Q2 | ethyl | isopropyl |
| Q2 | ethyl | cyclohexyl |
| Q3 | methyl | cyclopropyl |
| Q3 | ethyl | ethyl |
| Q3 | ethyl | isopropyl |
| Q3 | ethyl | cyclohexyl |
| Q3 | n-propyl | isopropyl |
| Q3 | isopropyl | isopropyl |
| Q4 | methyl | isopropyl |
| Q4 | ethyl | ethyl |
| Q4 | ethyl | isopropyl |
| Q4 | ethyl | cyclopropyl |
| Q4 | ethyl | s-butyl |
| Q4 | n-propyl | isopropyl |
| Q4 | isopropyl | isopropyl |
| Q5 | methyl | isopropyl |
| Q5 | ethyl | isopropyl |
| Q5 | ethyl | cyclopropyl |
| Q5 | ethyl | cyclohexyl |
| Q5 | n-propyl | isopropyl |
| Q6 | methyl | isopropyl |
| Q6 | ethyl | ethyl |
| Q6 | ethyl | isopropyl |
| Q6 | ethyl | cyclohexyl |
| Q6 | n-propyl | isopropyl |
| Q6 | isopropyl | isopropyl |
| Q7 | methyl | isopropyl |
| Q7 | ethyl | ethyl |
| Q7 | ethyl | n-propyl |
| Q7 | ethyl | isopropyl |
| Q7 | ethyl | cyclohexyl |
| Q7 | n-propyl | isopropyl |
| Q8 | methyl | isopropyl |
| Q8 | ethyl | etyl |
| Q8 | ethyl | isopropyl |
| Q8 | ethyl | propyl |
| Q8 | ethyl | cyclopropyl |
| Q8 | ethyl | s-butyl |
| Q8 | n-propyl | isopropyl |
| Q9 | methyl | n-propyl |
| Q9 | methyl | isopropyl |
| Q9 | methyl | t-butyl |
| Q9 | methyl | cyclopentyl |
| Q9 | methyl | cyclohexyl |
| Q9 | methyl | 2-methyl-2-propenyl |
| Q9 | ethyl | ethyl |
| Q9 | ethyl | isopropyl |
| Q9 | ethyl | cyclopropyl |
| Q9 | ethyl | cyclohexyl |
| Q9 | n-propyl | isopropyl |
| Q9 | n-propyl | cyclopropyl |
| Q9 | n-propyl | s-butyl |
| Q9 | isopropyl | isopropyl |
| Q9 | isopropyl | phenyl |
| Q9 | isopropyl | allyl |
| Q10 | methyl | isopropyl |
| Q10 | ethyl | ethyl |
| Q10 | ethyl | isopropyl |
| Q10 | ethyl | cyclopropyl |
| Q10 | ethyl | cyclopentyl |
| Q10 | ethyl | cyclopropyl |
| Q10 | ethyl | 2-chloroethyl |
| Q10 | ethyl | 2,2,2-trifluoroethyl |
| Q10 | 2-chloroethyl | 2-chloroethyl |
| Q10 | n-propyl | isopropyl |
| Q10 | n-propyl | 2-chloroethyl |
| Q10 | n-propyl | 2,2,2-trifluoroethyl |

TABLE 1-continued

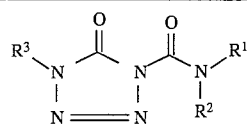

| R³ | R¹ | R² |
| --- | --- | --- |
| Q10 | isopropyl | cyclohexyl |
| Q10 | isopropyl | phenyl |
| Q10 | isopropyl | 2-chloroethyl |
| Q10 | isopropyl | 2,2,2-trifluoroethyl |
| Q11 | methyl | isopropyl |
| Q11 | ethyl | ethyl |
| Q11 | ethyl | isopropyl |
| Q11 | ethyl | cyclopropyl |
| Q12 | methyl | isopropyl |
| Q12 | ethyl | ethyl |
| Q12 | ethyl | isopropyl |
| Q12 | ethyl | cyclopropyl |
| Q12 | ethyl | cyclohexyl |
| Q12 | n-propyl | isopropyl |
| Q13 | methyl | isopropyl |
| Q13 | ethyl | ethyl |
| Q13 | ethyl | isopropyl |
| Q13 | ethyl | cyclopropyl |
| Q13 | ethyl | cyclohexyl |
| Q13 | n-propyl | isopropyl |
| Q13 | isopropyl | isopropyl |
| Q13 | isopropyl | phenyl |
| Q14 | methyl | ethyl |
| Q14 | methyl | n-propyl |
| Q14 | methyl | isopropyl |
| Q14 | methyl | cyclopropyl |
| Q14 | methyl | t-butyl |
| Q14 | methyl | cyclohexyl |
| Q14 | ethyl | ethyl |
| Q14 | ethyl | isopropyl |
| Q14 | ethyl | cyclopropyl |
| Q14 | ethyl | s-butyl |
| Q14 | ethyl | cyclopentyl |
| Q14 | ethyl | cyclopropyl |
| Q14 | ethyl | phenyl |
| Q14 | n-propyl | isopropyl |
| Q14 | n-propyl | s-butyl |
| Q14 | n-propyl | cyclohexyl |
| Q14 | isopropyl | isopropyl |
| Q14 | isopropyl | phenyl |
| Q14 | isopropyl | allyl |
| Q15 | methyl | isopropyl |
| Q15 | ethyl | ethyl |
| Q15 | ethyl | isopropyl |
| Q15 | ethyl | cyclohexyl |
| Q15 | n-propyl | isopropyl |
| Q15 | isopropyl | isopropyl |
| Q16 | methyl | isopropyl |
| Q16 | ethyl | ethyl |
| Q16 | ethyl | isopropyl |
| Q16 | ethyl | cyclopropyl |
| Q16 | ethyl | s-butyl |
| Q16 | ethyl | cyclohexyl |
| Q16 | n-propyl | isopropyl |
| Q16 | isopropyl | isopropyl |
| Q17 | methyl | isopropyl |
| Q17 | ethyl | ethyl |
| Q17 | ethyl | isopropyl |
| Q18 | methyl | isopropyl |
| Q18 | ethyl | ethyl |
| Q18 | ethyl | isopropyl |
| Q19 | methyl | isopropyl |
| Q19 | ethyl | ethyl |
| Q19 | ethyl | isopropyl |
| Q19 | ethyl | cyclopropyl |
| Q20 | methyl | isopropyl |
| Q20 | ethyl | isopropyl |
| Q20 | ethyl | cyclohexyl |
| Q23 | methyl | isopropyl |
| Q23 | ethyl | ethyl |

TABLE 1-continued

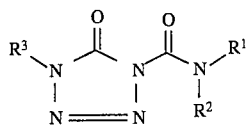

| R³ | R¹ | R² |
|---|---|---|
| Q23 | ethyl | isopropyl |
| Q23 | ethyl | cyclopropyl |
| Q23 | methyl | isopropyl |
| Q23 | ethyl | ethyl |
| Q23 | ethyl | isopropyl |
| Q23 | ethyl | cyclopropyl |
| Q23 | methyl | ethyl |
| Q23 | methyl | n-propyl |
| Q23 | methyl | isopropyl |
| Q23 | methyl | cyclopropyl |
| Q23 | methyl | s-butyl |
| Q23 | methyl | cyclopentyl |
| Q23 | methyl | cyclohexyl |
| Q23 | methyl | 2-methyl-2-propenyl |
| Q23 | ethyl | ethyl |
| Q23 | ethyl | n-propyl |
| Q23 | ethyl | isopropyl |
| Q23 | ethyl | cyclopropyl |
| Q23 | ethyl | s-butyl |
| Q23 | ethyl | cyclopropyl |
| Q23 | n-propyl | isopropyl |
| Q23 | n-propyl | cyclopropyl |
| Q23 | n-propyl | cyclopropyl |
| Q23 | isopropyl | isopropyl |
| Q23 | isopropyl | phenyl |
| Q23 | isopropyl | allyl |
| Q24 | methyl | isopropyl |
| Q24 | methyl | cyclopropyl |
| Q24 | ethyl | ethyl |
| Q24 | ethyl | isopropyl |
| Q24 | ethyl | cyclopropyl |
| Q24 | ethyl | cyclohexyl |
| Q24 | n-propyl | isopropyl |
| Q24 | isopropyl | isopropyl |
| Q25 | methyl | isopropyl |
| Q25 | ethyl | ethyl |
| Q25 | ethyl | isopropyl |
| Q25 | ethyl | cyclopropyl |
| Q26 | methyl | isopropyl |
| Q26 | ethyl | ethyl |
| Q26 | ethyl | n-propyl |
| Q26 | ethyl | isopropyl |
| Q26 | ethyl | cyclopropyl |
| Q26 | ethyl | cyclohexyl |
| Q26 | n-propyl | isopropyl |
| Q26 | isopropyl | isopropyl |
| Q27 | methyl | isopropyl |
| Q27 | ethyl | ethyl |
| Q27 | ethyl | isopropyl |
| Q27 | ethyl | cyclohexyl |
| Q28 | methyl | isopropyl |
| Q28 | ethyl | ethyl |
| Q28 | ethyl | isopropyl |
| Q28 | ethyl | cyclopropyl |
| Q29 | methyl | isopropyl |
| Q29 | methyl | cyclopropyl |
| Q29 | ethyl | ethyl |
| Q29 | ethyl | isopropyl |
| Q29 | ethyl | cyclopropyl |
| Q29 | ethyl | cyclohexyl |
| Q29 | ethyl | 2-chloroethyl |
| Q29 | ethyl | 2,2,2-trifluoroethyl |
| Q29 | 2-chloroethyl | 2-chloroethyl |
| Q29 | n-propyl | isopropyl |
| Q29 | n-propyl | 2-chloroethyl |
| Q29 | n-propyl | 2,2,2-trifluoroethyl |
| Q29 | isopropyl | isopropyl |
| Q29 | isopropyl | 2-chloroethyl |
| Q29 | isopropyl | 2,2,2-trifluoroethyl |
| Q30 | methyl | n-propyl |
| Q30 | methyl | isopropyl |

TABLE 1-continued

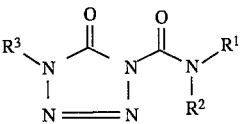

| R³ | R¹ | R² |
|---|---|---|
| Q30 | methyl | cyclopropyl |
| Q30 | methyl | s-butyl |
| Q30 | methyl | cyclopentyl |
| Q30 | methyl | 2-methyl-2-propenyl |
| Q30 | ethyl | ethyl |
| Q30 | ethyl | n-propyl |
| Q30 | ethyl | isopropyl |
| Q30 | ethyl | cyclopropyl |
| Q30 | ethyl | s-butyl |
| Q30 | ethyl | cyclohexyl |
| Q30 | n-propyl | isopropyl |
| Q30 | n-propyl | cyclohexyl |
| Q30 | isopropyl | isopropyl |
| Q30 | isopropyl | cyclohexyl |
| Q30 | isopropyl | allyl |
| Q31 | methyl | isopropyl |
| Q31 | ethyl | ethyl |
| Q31 | ethyl | isopropyl |
| Q31 | ethyl | cyclopropyl |
| Q31 | ethyl | cyclohexyl |
| Q31 | n-methyl | isopropyl |
| Q31 | isopropyl | isopropyl |
| Q32 | methyl | isopropyl |
| Q32 | ethyl | |
| Q32 | ethyl | isopropyl |
| Q32 | ethyl | cyclohexyl |
| 33 | methyl | isopropyl |
| Q33 | ethyl | ethyl |
| Q33 | ethyl | isopropyl |
| Q33 | ethyl | cyclopropyl |
| Q33 | ethyl | chloroethyl |
| Q33 | ethyl | 2,2,2-trifluoroethyl |
| Q33 | 2-chloroethyl | 2-chloroethyl |
| Q34 | methyl | isopropyl |
| Q34 | ethyl | ethyl |
| Q34 | ethyl | isopropyl |
| Q34 | ethyl | cyclopropyl |
| Q34 | ethyl | cyclohexyl |
| Q34 | n-propyl | isopropyl |
| Q34 | isopropyl | isopropyl |
| Q35 | methyl | isopropyl |
| Q35 | ethyl | ethyl |
| Q35 | ethyl | isopropyl |
| Q35 | isopropyl | phenyl |
| Q36 | methyl | isopropyl |
| Q36 | ethyl | ethyl |
| Q36 | ethyl | isopropyl |
| Q36 | ethyl | cyclohexyl |
| Q37 | methyl | isopropyl |
| Q37 | ethyl | ethyl |
| Q37 | ethyl | isopropyl |
| Q37 | ethyl | cyclopropyl |
| Q37 | methyl | isopropyl |
| Q37 | ethyl | ethyl |
| Q38 | ethyl | isopropyl |
| Q38 | ethyl | cyclopropyl |
| Q38 | isopropyl | phenyl |
| Q38 | methyl | isopropyl |
| Q38 | ethyl | ethyl |
| Q39 | ethyl | isopropyl |
| Q39 | isopropyl | phenyl |
| Q40 | methyl | isopropyl |
| Q40 | ethyl | ethyl |
| Q40 | ethyl | isopropyl |
| Q40 | ethyl | cyclopropyl |
| Q41 | methyl | isopropyl |
| Q41 | ethyl | ethyl |
| Q41 | ethyl | isopropyl |
| Q41 | ethyl | cyclopropyl |
| Q41 | ethyl | 2-chloroethyl |
| Q41 | ethyl | 2,2,2-trifluoroethyl |

TABLE 1-continued

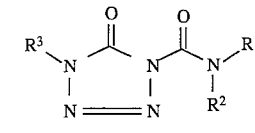

| R³ | R¹ | R² |
|---|---|---|
| Q41 | 2-chloroethyl | 2-chloroethyl |
| Q42 | methyl | isopropyl |
| Q42 | ethyl | ethyl |
| Q42 | ethyl | isopropyl |
| Q42 | ethyl | cyclopropyl |
| Q42 | ethyl | s-butyl |
| Q42 | ethyl | cyclohexyl |
| Q42 | n-propyl | isopropyl |
| Q42 | isopropyl | phenyl |
| Q43 | methyl | isopropyl |
| Q43 | ethyl | ethyl |
| Q43 | ethyl | isopropyl |
| Q43 | ethyl | cyclopropyl |
| Q44 | methyl | isopropyl |
| Q44 | ethyl | ethyl |
| Q44 | ethyl | isopropyl |
| Q44 | ethyl | cyclohexyl |
| Q45 | ethyl | ethyl |
| Q45 | ethyl | isopropyl |
| Q46 | ethyl | ethyl |
| Q46 | ethyl | isopropyl |
| Q46 | ethyl | cyclohexyl |
| Q47 | methyl | methyl |
| Q47 | methyl | ethyl |
| Q47 | methyl | n-propyl |
| Q47 | methyl | isopropyl |
| Q47 | methyl | cyclopropyl |
| Q47 | methyl | s-butyl |
| Q47 | methyl | t-butyl |
| Q47 | methyl | cyclopentyl |
| Q47 | methyl | cyclohexyl |
| Q47 | methyl | phenyl |
| Q47 | methyl | 2-methyl-2-propenyl |
| Q47 | methoxy | isopropyl |
| Q47 | ethyl | ethyl |
| Q47 | ethyl | n-propyl |
| Q47 | ethyl | isopropyl |
| Q47 | ethyl | cyclopropyl |
| Q47 | ethyl | s-butyl |
| Q47 | ethyl | cyclopentyl |
| Q47 | ethyl | cyclohexyl |
| Q47 | ethyl | phenyl |
| Q47 | ethyl | 2-chloroethyl |
| Q47 | ethyl | 2,2,2-trifluoroethyl |
| Q47 | 2-chloroethyl | 2-chloroethyl |
| Q47 | n-propyl | isopropyl |
| Q47 | n-propyl | cyclopropyl |
| Q47 | n-propyl | s-butyl |
| Q47 | n-propyl | cyclopentyl |
| Q47 | n-propyl | cyclohexyl |
| Q47 | n-propyl | 2-chloroethyl |
| Q47 | n-propyl | 2,2,2-trifluoroethyl |
| Q47 | isopropyl | isopropyl |
| Q47 | isopropyl | cyclohexyl |
| Q47 | isopropyl | phenyl |
| Q47 | isopropyl | allyl |
| Q47 | isopropyl | 2-chloroethyl |
| Q47 | isopropyl | 2,2,2-trifluoroethyl |
| Q48 | ethyl | ethyl |
| Q48 | ethyl | isopropyl |
| Q48 | isopropyl | phenyl |
| Q49 | methyl | methyl |
| Q49 | methyl | ethyl |
| Q49 | methyl | n-propyl |
| Q49 | methyl | isopropyl |
| Q49 | methyl | cyclopropyl |
| Q49 | methyl | s-butyl |
| Q49 | methyl | t-butyl |
| Q49 | methyl | cyclopentyl |
| Q49 | methyl | cyclohexyl |
| Q49 | methyl | phenyl |
| Q49 | methyl | 2-methyl-2-propenyl |
| Q49 | ethyl | ethyl |
| Q49 | ethyl | n-propyl |
| Q49 | ethyl | isopropyl |
| Q49 | ethyl | cyclopropyl |
| Q49 | ethyl | s-butyl |
| Q49 | ethyl | cyclopentyl |
| Q49 | ethyl | cyclohexyl |
| Q49 | ethyl | phenyl |
| Q49 | n-propyl | isopropyl |
| Q49 | n-propyl | cyclopropyl |
| Q49 | n-propyl | s-butyl |
| Q49 | n-propyl | cyclopentyl |
| Q49 | n-propyl | cyclohexyl |
| Q49 | isopropyl | isopropyl |
| Q49 | isopropyl | cyclohexyl |
| Q49 | isopropyl | phenyl |
| Q49 | isopropyl | allyl |
| Q50 | ethyl | ethyl |
| Q50 | ethyl | isopropyl |
| Q50 | isopropyl | phenyl |
| Q51 | methyl | isopropyl |
| Q51 | ethyl | ethyl |
| Q51 | ethyl | isopropyl |
| Q51 | isopropyl | phenyl |
| Q52 | ethyl | ethyl |
| Q52 | ethyl | isopropyl |
| Q52 | isopropyl | phenyl |
| Q53 | methyl | isopropyl |
| Q53 | ethyl | ethyl |
| Q53 | ethyl | isopropyl |
| Q53 | isopropyl | phenyl |
| Q54 | methyl | isopropyl |
| Q54 | ethyl | ethyl |
| Q54 | ethyl | isopropyl |
| Q54 | ethyl | cyclopropyl |
| Q54 | isopropyl | phenyl |
| Q55 | ethyl | ethyl |
| Q55 | ethyl | isopropyl |
| Q55 | isopropyl | phenyl |
| Q56 | methyl | isopropyl |
| Q56 | methyl | cyclopropyl |
| Q56 | ethyl | ethyl |
| Q56 | ethyl | isopropyl |
| Q56 | isopropyl | isopropyl |
| Q56 | isopropyl | phenyl |
| Q57 | methyl | ethyl |
| Q57 | methyl | n-propyl |
| Q57 | methyl | isopropyl |
| Q57 | methyl | cyclopropyl |
| Q57 | methyl | s-butyl |
| Q57 | methyl | t-butyl |
| Q57 | methyl | cyclopentyl |
| Q57 | methyl | cyclohexyl |
| Q57 | methyl | phenyl |
| Q57 | methyl | 2-methyl-2-propenyl |
| Q57 | ethyl | ethyl |
| Q57 | ethyl | n-propyl |
| Q57 | ethyl | isopropyl |
| Q57 | ethyl | cyclopropyl |
| Q57 | ethyl | s-butyl |
| Q57 | ethyl | cyclopentyl |
| Q57 | ethyl | cyclohexyl |
| Q57 | ethyl | phenyl |
| Q57 | n-propyl | isopropyl |
| Q57 | n-propyl | cyclopropyl |
| Q57 | n-propyl | s-butyl |
| Q57 | n-propyl | cyclopentyl |
| Q57 | n-propyl | cyclohexyl |
| Q57 | isopropyl | isopropyl |
| Q57 | isopropyl | cyclohexyl |

TABLE 1-continued

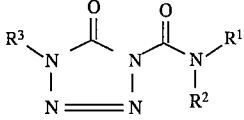

| R³ | R¹ | R² |
|---|---|---|
| Q57 | isopropyl | phenyl |
| Q57 | isopropyl | allyl |
| Q58 | methyl | isopropyl |
| Q58 | ethyl | ethyl |
| Q58 | ethyl | n-propyl |
| Q58 | ethyl | isopropyl |
| Q58 | ethyl | cyclopropyl |
| Q58 | ethyl | s-butyl |
| Q58 | ethyl | cyclohexyl |
| Q58 | n-propyl | isopropyl |
| Q58 | isopropyl | isopropyl |
| Q58 | isopropyl | phenyl |
| Q59 | methyl | methyl |
| Q59 | methyl | ethyl |
| Q59 | methyl | n-propyl |
| Q59 | methyl | isopropyl |
| Q59 | methyl | cyclopropyl |
| Q59 | methyl | s-butyl |
| Q59 | methyl | t-butyl |
| Q59 | methyl | cyclopentyl |
| Q59 | methyl | cyclohexyl |
| Q59 | methyl | propyl |
| Q59 | methyl | 2-methyl-2-propenyl |
| Q59 | ethyl | ethyl |
| Q59 | ethyl | n-propyl |
| Q59 | ethyl | isopropyl |
| Q59 | ethyl | cyclopropyl |
| Q59 | ethyl | s-butyl |
| Q59 | ethyl | cyclopentyl |
| Q59 | ethyl | cyclohexyl |
| Q59 | ethyl | phenyl |
| Q59 | n-propyl | isopropyl |
| Q59 | n-propyl | cyclopropyl |
| Q59 | n-propyl | s-butyl |
| Q59 | n-propyl | cyclopentyl |
| Q59 | n-propyl | cyclohexyl |
| Q59 | isopropyl | isopropyl |
| Q59 | isopropyl | cyclohexyl |
| Q59 | isopropyl | phenyl |
| Q59 | isopropyl | allyl |
| Q60 | methyl | isopropyl |
| Q60 | ethyl | ethyl |
| Q60 | ethyl | isopropyl |
| Q60 | ethyl | cyclopropyl |
| Q60 | ethyl | cyclohexyl |
| Q60 | n-propyl | isopropyl |
| Q60 | isopropyl | phenyl |
| Q61 | methyl | methyl |
| Q61 | methyl | ethyl |
| Q61 | methyl | n-propyl |
| Q61 | methyl | isopropyl |
| Q61 | methyl | cyclopropyl |
| Q61 | methyl | s-butyl |
| Q61 | methyl | t-butyl |
| Q61 | methyl | cyclopentyl |
| Q61 | methyl | cyclohexyl |
| Q61 | methyl | phenyl |
| Q61 | methyl | 2-methyl-2-propenyl |
| Q61 | ethyl | ethyl |
| Q61 | ethyl | n-propyl |
| Q61 | ethyl | isopropyl |
| Q61 | ethyl | cyclopropyl |
| Q61 | ethyl | cyclopentyl |
| Q61 | ethyl | cyclohexyl |
| Q61 | ethyl | phenyl |
| Q61 | ethyl | isopropyl |
| Q61 | n-methyl | cyclopropyl |
| Q61 | n-propyl | s-butyl |
| Q61 | n-propyl | cyclopentyl |
| Q61 | n-propyl | cyclohexyl |
| Q61 | isopropyl | isopropyl |

TABLE 1-continued

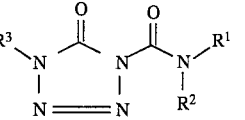

| R³ | R¹ | R² |
|---|---|---|
| Q61 | isopropyl | cyclohexyl |
| Q61 | isopropyl | phenyl |
| Q61 | isopropyl | allyl |
| Q62 | methyl | isopropyl |
| Q62 | ethyl | ethyl |
| Q62 | ethyl | isopropyl |
| Q62 | isopropyl | phenyl |
| Q63 | methyl | isopropyl |
| Q63 | ethyl | ethyl |
| Q63 | ethyl | isopropyl |
| Q63 | ethyl | cyclohexyl |
| Q64 | methyl | isopropyl |
| Q64 | ethyl | ethyl |
| Q64 | ethyl | isopropyl |
| Q64 | ethyl | cyclohexyl |
| Q64 | n-propyl | isopropyl |
| Q64 | isopropyl | isopropyl |
| Q65 | methyl | isopropyl |
| Q65 | ethyl | ethyl |
| Q65 | ethyl | n-propyl |
| Q65 | ethyl | isopropyl |
| Q65 | ethyl | cyclopropyl |
| Q65 | ethyl | s-butyl |
| Q65 | ethyl | cyclohexyl |
| Q65 | n-propyl | isopropyl |
| Q65 | isopropyl | isopropyl |
| Q65 | isopropyl | phenyl |
| Q66 | methyl | isopropyl |
| Q66 | ethyl | ethyl |
| Q66 | ethyl | isopropyl |
| Q66 | ethyl | cyclopropyl |
| Q67 | methyl | isopropyl |
| Q67 | methyl | cyclopropyl |
| Q67 | ethyl | ethyl |
| Q67 | ethyl | isopropyl |
| Q67 | ethyl | cyclopropyl |
| Q67 | ethyl | cyclohexyl |
| Q67 | n-propyl | isopropyl |
| Q67 | isopropyl | phenyl |
| Q68 | methyl | isopropyl |
| Q68 | ethyl | ethyl |
| Q68 | ethyl | isopropyl |
| Q68 | ethyl | cyclopropyl |
| Q69 | ethyl | ethyl |
| Q69 | ethyl | isopropyl |
| Q70 | ethyl | ethyl |
| Q70 | ethyl | isopropyl |
| Q71 | ethyl | ethyl |
| Q71 | ethyl | isopropyl |
| Q71 | ethyl | cyclopropyl |
| Q72 | methyl | isopropyl |
| Q72 | methyl | cyclopropyl |
| Q72 | ethyl | ethyl |
| Q72 | ethyl | isopropyl |
| Q72 | ethyl | cyclopropyl |
| Q72 | ethyl | cyclohexyl |
| Q72 | n-propyl | isopropyl |
| Q72 | isopropyl | isopropyl |
| Q73 | methyl | isopropyl |
| Q73 | ethyl | ethyl |
| Q73 | ethyl | n-propyl |
| Q73 | ethyl | isopropyl |
| Q73 | ethyl | cyclopropyl |
| Q73 | ethyl | cyclohexyl |
| Q73 | isopropyl | isopropyl |
| Q74 | methyl | isopropyl |
| Q74 | ethyl | ethyl |
| Q74 | ethyl | isopropyl |
| Q74 | ethyl | cyclopropyl |
| Q74 | ethyl | cyclohexyl |
| Q74 | n-propyl | isopropyl |

TABLE 1-continued

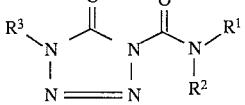

| R³ | R¹ | R² |
|---|---|---|
| Q74 | isopropyl | isopropyl |
| Q75 | methyl | isopropyl |
| Q75 | ethyl | ethyl |
| Q75 | ethyl | isopropyl |
| Q75 | ethyl | cyclopropyl |
| Q75 | ethyl | cyclohexyl |
| Q75 | ethyl | 2-chloroethyl |
| Q75 | ethyl | 2,2,2-trifluoroethyl |
| Q75 | 2-chloroethyl | 2-chloroethyl |
| Q75 | isopropyl | isopropyl |
| Q76 | methyl | isopropyl |
| Q76 | ethyl | ethyl |
| Q76 | ethyl | isopropyl |
| Q77 | methyl | isopropyl |
| Q77 | ethyl | ethyl |
| Q77 | ethyl | isopropyl |
| Q77 | ethyl | cyclohexyl |
| Q78 | methyl | isopropyl |
| Q78 | ethyl | ethyl |
| Q78 | ethyl | isopropyl |
| Q78 | ethyl | cyclopropyl |
| Q78 | ethyl | cyclopropyl |
| Q78 | n-propyl | isopropyl |
| Q79 | methyl | isopropyl |
| Q79 | ethyl | ethyl |
| Q79 | ethyl | n-propyl |
| Q79 | ethyl | isopropyl |
| Q79 | ethyl | cyclopropyl |
| Q79 | ethyl | s-butyl |
| Q79 | ethyl | cyclohexyl |
| Q79 | n-propyl | isopropyl |
| Q79 | isopropyl | phenyl |
| Q80 | methyl | isopropyl |
| Q80 | ethyl | ethyl |
| Q80 | ethyl | isopropyl |
| Q80 | ethyl | cyclopropyl |
| Q81 | methyl | isopropyl |
| Q81 | ethyl | ethyl |
| Q81 | ethyl | isopropyl |
| Q81 | ethyl | cyclopropyl |
| Q81 | ethyl | cyclohexyl |
| Q81 | n-propyl | isopropyl |
| Q81 | isopropyl | isopropyl |
| Q82 | methyl | isopropyl |
| Q82 | ethyl | ethyl |
| Q82 | ethyl | isopropyl |
| Q82 | ethyl | cyclohexyl |
| Q82 | methyl | methyl |
| Q83 | methyl | ethyl |
| Q83 | methyl | n-propyl |
| Q83 | methyl | isopropyl |
| Q83 | methyl | cyclopropyl |
| Q83 | methyl | s-butyl |
| Q83 | methyl | t-butyl |
| Q83 | methyl | cyclopentyl |
| Q83 | methyl | cyclohexyl |
| Q83 | methyl | phenyl |
| Q83 | methyl | 2-methyl-2-propenyl |
| Q83 | ethyl | ethyl |
| Q83 | ethyl | n-propyl |
| Q83 | ethyl | isopropyl |
| Q83 | ethyl | cyclopropyl |
| Q83 | ethyl | s-butyl |
| Q83 | ethyl | cyclopentyl |
| Q83 | ethyl | cyclohexyl |
| Q83 | ethyl | phenyl |
| Q83 | n-propyl | isopropyl |
| Q83 | n-propyl | cyclopropyl |
| Q83 | n-propyl | s-butyl |
| Q83 | n-propyl | cyclopentyl |
| Q83 | n-propyl | cyclohexyl |

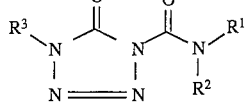

| R³ | R¹ | R² |
|---|---|---|
| Q83 | isopropyl | isopropyl |
| Q83 | isopropyl | cyclohexyl |
| Q83 | isopropyl | phenyl |
| Q83 | isopropyl | allyl |
| Q84 | methyl | methyl |
| Q84 | methyl | ethyl |
| Q84 | methyl | n-propyl |
| Q84 | methyl | isopropyl |
| Q84 | methyl | cyclopropyl |
| Q84 | methyl | s-butyl |
| Q84 | methyl | t-butyl |
| Q84 | methyl | cyclopentyl |
| Q84 | methyl | cyclohexyl |
| Q84 | methyl | phenyl |
| Q84 | methyl | 2-methyl-2-propenyl |
| Q84 | ethyl | ethyl |
| Q84 | ethyl | n-propyl |
| Q84 | ethyl | isopropyl |
| Q84 | ethyl | cyclopropyl |
| Q84 | ethyl | s-butyl |
| Q84 | ethyl | cyclopentyl |
| Q84 | ethyl | cyclohexyl |
| Q84 | ethyl | phenyl |
| Q84 | n-propyl | isopropyl |
| Q84 | n-propyl | cyclopropyl |
| Q84 | n-propyl | s-butyl |
| Q84 | n-propyl | cyclopentyl |
| Q84 | n-propyl | cyclohexyl |
| Q84 | isopropyl | isopropyl |
| Q84 | isopropyl | cyclohexyl |
| Q84 | isopropyl | phenyl |
| Q84 | isopropyl | allyl |
| Q85 | methyl | isopropyl |
| Q85 | ethyl | isopropyl |
| Q85 | ethyl | cyclopropyl |
| Q85 | methyl | methyl |
| Q86 | methyl | ethyl |
| Q86 | methyl | n-propyl |
| Q86 | methyl | isopropyl |
| Q86 | methyl | cyclopropyl |
| Q86 | methyl | s-butyl |
| Q86 | methyl | t-butyl |
| Q86 | methyl | cyclohexyl |
| Q86 | methyl | 2-methyl-2-propenyl |
| Q86 | ethyl | ethyl |
| Q86 | ethyl | n-propyl |
| Q86 | ethyl | isopropyl |
| Q86 | ethyl | cyclopropyl |
| Q86 | ethyl | s-butyl |
| Q86 | ethyl | cyclohexyl |
| Q86 | n-propyl | isopropyl |
| Q86 | n-propyl | cyclopropyl |
| Q86 | n-propyl | cyclohexyl |
| Q86 | isopropyl | isopropyl |
| Q86 | isopropyl | allyl |
| Q87 | methyl | isopropyl |
| Q87 | ethyl | ethyl |
| Q87 | ethyl | isopropyl |
| Q87 | ethyl | cyclopropyl |
| Q87 | isopropyl | phenyl |
| Q88 | methyl | isopropyl |
| Q88 | methyl | cyclopropyl |
| Q88 | ethyl | ethyl |
| Q88 | ethyl | isopropyl |
| Q88 | ethyl | cyclopropyl |
| Q88 | ethyl | cyclohexyl |
| Q88 | n-propyl | isopropyl |
| Q88 | isopropyl | isopropyl |
| Q89 | methyl | isopropyl |
| Q89 | ethyl | ethyl |
| Q89 | ethyl | isopropyl |

TABLE 1-continued

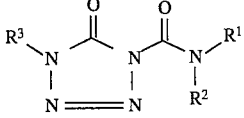

| | R³ | R¹ | R² |
|---|---|---|---|
| Q89 | ethyl | | cyclohexyl |
| Q90 | methyl | | methyl |
| Q90 | methyl | | ethyl |
| Q90 | methyl | | n-propyl |
| Q90 | methyl | | isopropyl |
| Q90 | methyl | | cyclopropyl |
| Q90 | methyl | | s-butyl |
| Q90 | methyl | | t-butyl |
| Q90 | methyl | | cyclopentyl |
| Q90 | methyl | | cyclohexyl |
| Q90 | methyl | | phenyl |
| Q90 | methyl | | 2-methyl-2-propenyl |
| Q90 | ethyl | | ethyl |
| Q90 | ethyl | | n-propyl |
| Q90 | ethyl | | isopropyl |
| Q90 | ethyl | | cyclopropyl |
| Q90 | ethyl | | s-butyl |
| Q90 | ethyl | | cyclopentyl |
| Q90 | ethyl | | cyclohexyl |
| Q90 | ethyl | | phenyl |
| Q90 | n-propyl | | isopropyl |
| Q90 | n-propyl | | cyclopropyl |
| Q90 | n-propyl | | s-butyl |
| Q90 | n-propyl | | cyclopentyl |
| Q90 | n-propyl | | cyclohexyl |
| Q90 | isopropyl | | isopropyl |
| Q90 | isopropyl | | cyclohexyl |
| Q90 | isopropyl | | phenyl |
| Q90 | isopropyl | | allyl |
| Q91 | methyl | | methyl |
| Q91 | methyl | | ethyl |
| Q91 | methyl | | n-propyl |
| Q91 | methyl | | isopropyl |
| Q91 | methyl | | cyclopropyl |
| Q91 | methyl | | s-butyl |
| Q91 | methyl | | t-butyl |
| Q91 | methyl | | cyclopentyl |
| Q91 | methyl | | cyclohexyl |
| Q91 | methyl | | phenyl |
| Q91 | methyl | | 2-methyl-2-propenyl |
| Q91 | ethyl | | ethyl |
| Q91 | ethyl | | n-propyl |
| Q91 | ethyl | | isopropyl |
| Q91 | ethyl | | cyclopropyl |
| Q91 | ethyl | | s-butyl |
| Q91 | ethyl | | cyclopentyl |
| Q91 | ethyl | | cyclohexyl |
| Q91 | ethyl | | phenyl |
| Q91 | n-propyl | | isopropyl |
| Q91 | n-propyl | | cyclopropyl |
| Q91 | n-propyl | | s-butyl |
| Q91 | n-propyl | | cyclopentyl |
| Q91 | n-propyl | | cyclopropyl |
| Q91 | isopropyl | | isopropyl |
| Q91 | isopropyl | | cyclohexyl |
| Q91 | isopropyl | | phenyl |
| Q91 | isopropyl | | allyl |
| Q92 | methyl | | isopropyl |
| Q92 | methyl | | cyclopropyl |
| Q92 | ethyl | | ethyl |
| Q92 | ethyl | | isopropyl |
| Q92 | ethyl | | cyclopropyl |
| Q92 | ethyl | | cyclohexyl |
| Q92 | n-propyl | | isopropyl |
| Q92 | isopropyl | | isopropyl |
| Q92 | isopropyl | | phenyl |
| Q93 | ethyl | | ethyl |
| Q93 | ethyl | | isopropyl |
| Q93 | ethyl | | cyclopropyl |
| Q94 | methyl | | isopropyl |
| Q94 | ethyl | | ethyl |
| Q94 | ethyl | | isopropyl |
| Q94 | ethyl | | cyclohexyl |
| Q94 | ethyl | | 2-chloroethyl |
| Q94 | ethyl | | 2,2,2-trifluoroethyl |
| Q94 | 2-chloroethyl | | 2-chloroethyl |
| Q95 | methyl | | isopropyl |
| Q95 | ethyl | | ethyl |
| Q95 | ethyl | | isopropyl |
| Q95 | ethyl | | cyclopropyl |
| Q96 | ethyl | | ethyl |
| Q96 | ethyl | | isopropyl |
| Q96 | ethyl | | cyclohexyl |
| Q96 | isopropyl | | phenyl |
| Q97 | ethyl | | ethyl |
| Q97 | ethyl | | isopropyl |
| Q97 | ethyl | | cyclopropyl |
| Q98 | ethyl | | ethyl |
| Q98 | ethyl | | isopropyl |
| Q99 | methyl | | isopropyl |
| Q99 | ethyl | | ethyl |
| Q99 | ethyl | | isopropyl |
| Q99 | ethyl | | cyclopropyl |
| Q100 | methyl | | isopropyl |
| Q100 | ethyl | | ethyl |
| Q100 | ethyl | | isopropyl |
| Q100 | ethyl | | cyclohexyl |
| Q100 | isopropyl | | phenyl |
| Q101 | methyl | | isopropyl |
| Q101 | ethyl | | ethyl |
| Q101 | ethyl | | isopropyl |
| Q101 | ethyl | | cyclohexyl |
| Q101 | isopropyl | | phenyl |
| Q102 | methyl | | isopropyl |
| Q102 | ethyl | | ethyl |
| Q102 | methyl | | isopropyl |
| Q103 | ethyl | | cyclohexyl |
| Q103 | ethyl | | ethyl |
| Q103 | ethyl | | isopropyl |
| Q103 | ethyl | | 2-chloroethyl |
| Q103 | ethyl | | 2,2,2-trifluoroethyl |
| Q103 | 2-chloroethyl | | 2-chloroethyl |
| Q104 | methyl | | isopropyl |
| Q104 | ethyl | | ethyl |
| Q104 | ethyl | | isopropyl |
| Q104 | ethyl | | cyclohexyl |
| Q105 | methyl | | isopropyl |
| Q105 | methyl | | cyclopropyl |
| Q105 | ethyl | | ethyl |
| Q105 | ethyl | | isopropyl |
| Q105 | ethyl | | cyclopropyl |
| Q105 | ethyl | | cyclohexyl |
| Q105 | n-propyl | | isopropyl |
| Q105 | isopropyl | | isopropyl |
| Q105 | isopropyl | | phenyl |
| Q106 | methyl | | isopropyl |
| Q106 | ethyl | | ethyl |
| Q106 | ethyl | | n-propyl |
| Q106 | ethyl | | isopropyl |
| Q106 | ethyl | | cyclopropyl |
| Q107 | methyl | | methyl |
| Q107 | methyl | | ethyl |
| Q107 | methyl | | n-propyl |
| Q107 | methyl | | isopropyl |
| Q107 | methyl | | cyclopropyl |
| Q107 | methyl | | s-butyl |
| Q107 | methyl | | t-butyl |
| Q107 | methyl | | cyclopentyl |
| Q107 | methyl | | cyclohexyl |
| Q107 | methyl | | phenyl |
| Q107 | methyl | | 2-methyl-2-propenyl |
| Q107 | ethyl | | ethyl |

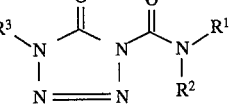

TABLE 1-continued

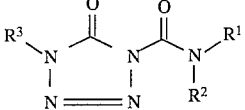

| R³ | R¹ | R² |
|---|---|---|
| Q107 | ethyl | n-propyl |
| Q107 | ethyl | isopropyl |
| Q107 | ethyl | cyclopropyl |
| Q107 | ethyl | s-butyl |
| Q167 | ethyl | cyclopentyl |
| Q107 | ethyl | cyclohexyl |
| Q107 | ethyl | phenyl |
| Q107 | n-propyl | isopropyl |
| Q107 | n-propyl | cyclopropyl |
| Q107 | n-propyl | s-butyl |
| Q107 | n-propyl | cyclopentyl |
| Q107 | n-propyl | cyclohexyl |
| Q107 | isopropyl | isopropyl |
| Q107 | isopropyl | cyclohexyl |
| Q107 | isopropyl | phenyl |
| Q107 | isopropyl | allyl |
| Q108 | methyl | isopropyl |
| Q108 | ethyl | ethyl |
| Q108 | ethyl | n-propyl |
| Q108 | ethyl | isopropyl |
| Q108 | ethyl | cyclopropyl |
| Q108 | ethyl | s-butyl |
| Q108 | ethyl | cyclohexyl |
| Q108 | n-propyl | isopropyl |
| Q108 | isopropyl | isopropyl |
| Q108 | isopropyl | phenyl |
| Q108 | methyl | methyl |
| Q108 | methyl | ethyl |
| Q108 | methyl | n-propyl |
| Q108 | methyl | cyclopropyl |
| Q108 | methyl | s-butyl |
| Q108 | methyl | t-butyl |
| Q108 | methyl | cyclopentyl |
| Q108 | methyl | cyclohexyl |
| Q108 | methyl | phenyl |
| Q108 | methyl | 2-methyl-2-propenyl |
| Q108 | ethyl | cyclopentyl |
| Q108 | ethyl | phenyl |
| Q108 | n-propyl | cyclopropyl |
| Q108 | n-propyl | s-butyl |
| Q108 | n-propyl | cyclopentyl |
| Q108 | n-propyl | cyclohexyl |
| Q108 | isopropyl | cyclohexyl |
| Q108 | isopropyl | allyl |
| Q109 | methyl | methyl |
| Q109 | methyl | ethyl |
| Q109 | methyl | n-propyl |
| Q109 | methyl | isopropyl |
| Q109 | methyl | cyclopropyl |
| Q109 | methyl | s-butyl |
| Q109 | methyl | t-butyl |
| Q109 | methyl | cyclopentyl |
| Q109 | methyl | cyclohexyl |
| Q109 | methyl | phenyl |
| Q109 | methyl | 2-methyl-2-propenyl |
| Q109 | ethyl | ethyl |
| Q109 | ethyl | n-propyl |
| Q109 | ethyl | isopropyl |
| Q109 | ethyl | cyclopropyl |
| Q109 | ethyl | s-butyl |
| Q109 | ethyl | cyclopentyl |
| Q109 | ethyl | cyclohexyl |
| Q109 | ethyl | phenyl |
| Q109 | n-propyl | isopropyl |
| Q109 | n-propyl | cyclopropyl |
| Q109 | n-propyl | s-butyl |
| Q109 | n-propyl | cyclopentyl |
| Q109 | n-propyl | cyclohexyl |
| Q109 | isopropyl | isopropyl |
| Q109 | isopropyl | cyclohexyl |
| Q109 | isopropyl | phenyl |
| Q109 | isopropyl | allyl |
| Q110 | methyl | isopropyl |
| Q110 | methyl | cyclopropyl |
| Q110 | ethyl | ethyl |
| Q110 | ethyl | isopropyl |
| Q110 | ethyl | cyclopropyl |
| Q110 | ethyl | cyclohexyl |
| Q110 | n-propyl | isopropyl |
| Q110 | ethyl | ethyl |
| Q110 | ethyl | isopropyl |
| Q110 | ethyl | cyclopropyl |
| Q110 | ethyl | cyclohexyl |
| Q110 | n-propyl | isopropyl |
| Q110 | isopropyl | isopropyl |
| Q110 | isopropyl | phenyl |
| Q111 | methyl | isopropyl |
| Q111 | ethyl | ethyl |
| Q111 | ethyl | n-propyl |
| Q111 | ethyl | isopropyl |
| Q111 | ethyl | cyclopropyl |
| Q111 | ethyl | s-butyl |
| Q111 | ethyl | cyclohexyl |
| Q111 | n-propyl | isopropyl |
| Q111 | isopropyl | isopropyl |
| Q111 | isopropyl | phenyl |
| Q112 | methyl | methyl |
| Q112 | methyl | ethyl |
| Q112 | methyl | n-propyl |
| Q112 | methyl | isopropyl |
| Q112 | methyl | cyclopropyl |
| Q112 | methyl | s-butyl |
| Q112 | methyl | t-butyl |
| Q112 | methyl | cyclopentyl |
| Q112 | methyl | cyclopropyl |
| Q112 | methyl | phenyl |
| Q112 | methyl | 2-methyl-2-propenyl |
| Q112 | ethyl | ethyl |
| Q112 | ethyl | n-propyl |
| Q112 | ethyl | isopropyl |
| Q112 | ethyl | cyclopropyl |
| Q112 | ethyl | s-butyl |
| Q112 | ethyl | cyclopentyl |
| Q112 | ethyl | cyclohexyl |
| Q112 | ethyl | phenyl |
| Q112 | n-propyl | isopropyl |
| Q112 | ethyl | s-butyl |
| Q112 | ethyl | cyclopentyl |
| Q112 | ethyl | cyclohexyl |
| Q112 | ethyl | phenyl |
| Q112 | n-propyl | isopropyl |
| Q112 | n-propyl | cyclopropyl |
| Q112 | n-propyl | s-butyl |
| Q112 | n-propyl | cyclopentyl |
| Q112 | n-propyl | cyclohexyl |
| Q112 | isopropyl | isopropyl |
| Q112 | isopropyl | cyclohexyl |
| Q112 | isopropyl | phenyl |
| Q112 | isopropyl | allyl |
| Q113 | methyl | isopropyl |
| Q113 | methyl | cyclopropyl |
| Q113 | ethyl | ethyl |
| Q113 | ethyl | isopropyl |
| Q113 | ethyl | cyclopropyl |
| Q113 | ethyl | cyclohexyl |
| Q113 | n-propyl | isopropyl |
| Q113 | isopropyl | isopropyl |
| Q113 | isopropyl | phenyl |
| Q114 | methyl | methyl |
| Q114 | methyl | ethyl |
| Q114 | methyl | n-propyl |
| Q114 | methyl | isopropyl |

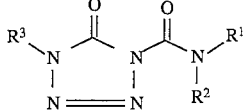

TABLE 1-continued

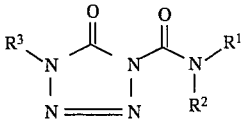

| R³ | R¹ | R² |
|---|---|---|
| Q114 | methyl | cyclopropyl |
| Q114 | methyl | s-butyl |
| Q114 | methyl | t-butyl |
| Q114 | methyl | cyclopentyl |
| Q114 | methyl | cyclohexyl |
| Q114 | methyl | phenyl |
| Q114 | methyl | 2-methyl-2-propenyl |
| Q114 | ethyl | ethyl |
| Q114 | ethyl | n-propyl |
| Q114 | ethyl | isopropyl |
| Q114 | ethyl | cyclopropyl |
| Q114 | ethyl | s-butyl |
| Q114 | ethyl | cyclopentyl |
| Q114 | ethyl | cyclopropyl |
| Q114 | ethyl | phenyl |
| Q114 | n-propyl | isopropyl |
| Q114 | n-propyl | cyclopropyl |
| Q114 | n-propyl | s-butyl |
| Q114 | n-propyl | cyclopentyl |
| Q114 | n-propyl | cyclohexyl |
| Q114 | isopropyl | isopropyl |
| Q114 | isopropyl | cyclohexyl |
| Q114 | isopropyl | phenyl |
| Q114 | isopropyl | allyl |
| Q115 | methyl | methyl |
| Q115 | methyl | ethyl |
| Q115 | methyl | n-propyl |
| Q115 | methyl | isopropyl |
| Q115 | methyl | cyclopropyl |
| Q115 | methyl | s-butyl |
| Q115 | methyl | t-butyl |
| Q115 | methyl | cyclopentyl |
| Q115 | methyl | cyclohexyl |
| Q115 | methyl | phenyl |
| Q115 | methyl | 2-methyl-2-propenyl |
| Q115 | ethyl | ethyl |
| Q115 | ethyl | n-propyl |
| Q115 | ethyl | isopropyl |
| Q115 | ethyl | cyclopropyl |
| Q115 | ethyl | s-butyl |
| Q115 | ethyl | cyclopentyl |
| Q115 | ethyl | cyclohexyl |
| Q115 | ethyl | phenyl |
| Q115 | n-propyl | isopropyl |
| Q115 | n-propyl | cyclopropyl |
| Q115 | n-propyl | s-butyl |
| Q115 | n-propyl | cyclopentyl |
| Q115 | n-propyl | cyclohexyl |
| Q115 | isopropyl | isopropyl |
| Q115 | isopropyl | cyclohexyl |
| Q115 | isopropyl | phenyl |
| Q115 | isopropyl | allyl |
| Q116 | methyl | methyl |
| Q116 | methyl | ethyl |
| Q116 | methyl | n-propyl |
| Q116 | methyl | isopropyl |
| Q116 | methyl | cyclopropyl |
| Q116 | methyl | s-butyl |
| Q116 | methyl | t-butyl |
| Q116 | methyl | cyclopentyl |
| Q116 | methyl | cyclohexyl |
| Q116 | methyl | phenyl |
| Q116 | methyl | 2-methyl-2-propenyl |
| Q116 | ethyl | ethyl |
| Q116 | ethyl | n-propyl |
| Q116 | ethyl | isopropyl |
| Q116 | ethyl | cyclopropyl |
| Q116 | ethyl | s-butyl |
| Q116 | ethyl | cyclopentyl |
| Q116 | ethyl | cyclohexyl |
| Q116 | ethyl | phenyl |

TABLE 1-continued

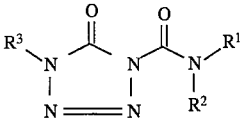

| R³ | R¹ | R² |
|---|---|---|
| Q116 | n-propyl | isopropyl |
| Q116 | n-propyl | cyclopropyl |
| Q116 | n-propyl | s-butyl |
| Q116 | n-propyl | cyclopentyl |
| Q116 | n-propyl | cyclohexyl |
| Q116 | isopropyl | isopropyl |
| Q116 | isopropyl | cyclohexyl |
| Q116 | isopropyl | phenyl |
| Q116 | isopropyl | allyl |
| Q117 | methyl | methyl |
| Q117 | methyl | ethyl |
| Q117 | methyl | n-propyl |
| Q117 | methyl | isopropyl |
| Q117 | methyl | cyclopropyl |
| Q117 | methyl | s-butyl |
| Q117 | methyl | t-butyl |
| Q117 | methyl | cyclopentyl |
| Q117 | methyl | cyclohexyl |
| Q117 | methyl | phenyl |
| Q117 | methyl | 2-methyl-2-propenyl |
| Q117 | ethyl | ethyl |
| Q117 | ethyl | n-propyl |
| Q117 | ethyl | isopropyl |
| Q117 | ethyl | cyclopropyl |
| Q117 | ethyl | s-butyl |
| Q117 | ethyl | cyclopentyl |
| Q117 | ethyl | cyclohexyl |
| Q117 | ethyl | phenyl |
| Q117 | n-propyl | isopropyl |
| Q117 | n-propyl | cyclopropyl |
| Q117 | n-propyl | s-butyl |
| Q117 | n-propyl | cyclopentyl |
| Q117 | n-propyl | cyclohexyl |
| Q117 | isopropyl | isopropyl |
| Q117 | isopropyl | cyclohexyl |
| Q117 | isopropyl | phenyl |
| Q117 | isopropyl | allyl |
| Q118 | methyl | methyl |
| Q118 | methyl | ethyl |
| Q118 | methyl | n-propyl |
| Q118 | methyl | isopropyl |
| Q118 | methyl | cyclopropyl |
| Q118 | methyl | s-butyl |
| Q118 | methyl | t-butyl |
| Q118 | methyl | cyclopentyl |
| Q118 | methyl | cyclohexyl |
| Q118 | methyl | phenyl |
| Q118 | methyl | 2-methyl-2-propenyl |
| Q118 | ethyl | ethyl |
| Q118 | ethyl | n-propyl |
| Q118 | ethyl | isopropyl |
| Q118 | ethyl | cyclopropyl |
| Q118 | ethyl | s-butyl |
| Q118 | ethyl | cyclopentyl |
| Q118 | ethyl | cyclohexyl |
| Q118 | ethyl | phenyl |
| Q118 | n-propyl | isopropyl |
| Q118 | n-propyl | cyclopropyl |
| Q118 | n-propyl | s-butyl |
| Q118 | n-propyl | cyclopentyl |
| Q118 | n-propyl | cyclohexyl |
| Q118 | isopropyl | isopropyl |
| Q118 | isopropyl | cyclohexyl |
| Q118 | isopropyl | phenyl |
| Q118 | isopropyl | allyl |
| Q119 | methyl | isopropyl |
| Q119 | methyl | cyclopropyl |
| Q119 | ethyl | ethyl |
| Q119 | ethyl | isopropyl |
| Q119 | ethyl | cyclopropyl |
| Q119 | ethyl | cyclohexyl |

TABLE 1-continued $$\underset{N=\!=\!N}{\overset{R^3}{\underset{|}{N}}\!\!-\!\!\overset{\overset{O}{\|}}{C}\!\!-\!\!\overset{|}{\underset{|}{N}}\!\!-\!\!\overset{\overset{O}{\|}}{C}\!\!-\!\!\overset{R^1}{\underset{R^2}{N}}}$$

| R³ | R¹ | R² |
|---|---|---|
| Q119 | n-propyl | isopropyl |
| Q119 | isopropyl | isopropyl |
| Q119 | isopropyl | phenyl |
| Q120 | methyl | methyl |
| Q120 | methyl | ethyl |
| Q120 | methyl | n-propyl |
| Q120 | methyl | isopropyl |
| Q120 | methyl | cyclopropyl |
| Q120 | methyl | s-butyl |
| Q120 | methyl | t-butyl |
| Q120 | methyl | cyclopentyl |
| Q120 | methyl | cyclohexyl |
| Q120 | methyl | phenyl |
| Q120 | methyl | 2-methyl-2-propenyl |
| Q120 | ethyl | ethyl |
| Q120 | ethyl | n-propyl |
| Q120 | ethyl | isopropyl |
| Q120 | ethyl | cyclopropyl |
| Q120 | ethyl | s-butyl |
| Q120 | ethyl | cyclopentyl |
| Q120 | ethyl | cyclohexyl |
| Q120 | ethyl | phenyl |
| Q120 | n-propyl | isopropyl |
| Q120 | n-propyl | cyclopropyl |
| Q120 | n-propyl | s-butyl |
| Q120 | n-propyl | cyclopentyl |
| Q120 | n-propyl | cyclohexyl |
| Q120 | isopropyl | isopropyl |
| Q120 | isopropyl | cyclohexyl |
| Q120 | isopropyl | phenyl |
| Q120 | isopropyl | allyl |
| Q121 | methyl | methyl |
| Q121 | methyl | ethyl |
| Q121 | methyl | n-propyl |
| Q121 | methyl | isopropyl |
| Q121 | methyl | cyclopropyl |
| Q121 | methyl | s-butyl |
| Q121 | methyl | t-butyl |
| Q121 | methyl | cyclopentyl |
| Q121 | methyl | cyclohexyl |
| Q121 | methyl | phenyl |
| Q121 | methyl | 2-methyl-2-propenyl |
| Q121 | ethyl | ethyl |
| Q121 | ethyl | n-propyl |
| Q121 | ethyl | isopropyl |
| Q121 | ethyl | cyclopropyl |
| Q121 | ethyl | s-butyl |
| Q121 | ethyl | cyclopentyl |
| Q121 | ethyl | cyclohexyl |
| Q121 | ethyl | phenyl |
| Q121 | n-propyl | isopropyl |
| Q121 | n-propyl | cyclopropyl |
| Q121 | n-propyl | s-butyl |
| Q121 | n-propyl | cyclopentyl |
| Q121 | n-prod | cyclohexyl |
| Q121 | isopropyl | isopropyl |
| Q121 | isopropyl | cyclohexyl |
| Q121 | isopropyl | phenyl |
| Q121 | isopropyl | allyl |
| Q122 | methyl | isopropyl |
| Q122 | methyl | cyclopropyl |
| Q122 | ethyl | ethyl |
| Q122 | ethyl | isopropyl |
| Q122 | ethyl | cyclopropyl |
| Q122 | ethyl | cyclohexyl |
| Q122 | n-propyl | isopropyl |
| Q122 | isopropyl | isopropyl |
| Q122 | isopropyl | phenyl |
| Q123 | methyl | isopropyl |
| Q123 | ethyl | ethyl |
| Q123 | ethyl | n-propyl |
| Q123 | ethyl | isopropyl |
| Q123 | ethyl | cyclopropyl |
| Q123 | ethyl | s-butyl |
| Q123 | ethyl | cyclohexyl |
| Q123 | n-propyl | isopropyl |
| Q123 | isopropyl | isopropyl |
| Q123 | isopropyl | phenyl |
| Q124 | methyl | isopropyl |
| Q124 | methyl | cyclopropyl |
| Q124 | ethyl | ethyl |
| Q124 | ethyl | isopropyl |
| Q124 | ethyl | cyclopropyl |
| Q124 | ethyl | cyclohexyl |
| Q124 | n-propyl | isopropyl |
| Q124 | isopropyl | isopropyl |
| Q124 | isopropyl | phenyl |
| Q125 | methyl | methyl |
| Q125 | methyl | ethyl |
| Q125 | methyl | n-propyl |
| Q125 | methyl | isopropyl |
| Q125 | methyl | cyclopropyl |
| Q125 | methyl | s-butyl |
| Q125 | methyl | t-butyl |
| Q125 | methyl | cyclopentyl |
| Q125 | methyl | cyclohexyl |
| Q125 | methyl | phenyl |
| Q125 | methyl | 2-methyl-2-propenyl |
| Q125 | ethyl | ethyl |
| Q125 | ethyl | n-propyl |
| Q125 | ethyl | isopropyl |
| Q125 | ethyl | cyclopropyl |
| Q125 | ethyl | s-butyl |
| Q125 | ethyl | cyclopentyl |
| Q125 | ethyl | cyclohexyl |
| Q125 | ethyl | phenyl |
| Q125 | n-propyl | cyclopropyl |
| Q125 | n-propyl | s-butyl |
| Q125 | n-propyl | cyclopentyl |
| Q125 | n-propyl | cyclohexyl |
| Q125 | isopropyl | isopropyl |
| Q125 | isopropyl | cyclohexyl |
| Q125 | isopropyl | phenyl |
| Q125 | isopropyl | allyl |
| Q126 | methyl | methyl |
| Q126 | methyl | ethyl |
| Q126 | methyl | n-propyl |
| Q126 | methyl | isopropyl |
| Q126 | methyl | allyl |
| Q126 | methyl | propargyl |
| Q126 | methyl | cyclopropyl |
| Q126 | methyl | s-butyl |
| Q126 | methyl | t-butyl |
| Q126 | methyl | isobutyl |
| Q126 | methyl | cyclopentyl |
| Q126 | methyl | cyclohexyl |
| Q126 | methyl | cycloheptyl |
| Q126 | methyl | phenyl |
| Q126 | methyl | 2-methyl-2-propenyl |
| Q126 | methoxy | cyclohexyl |
| Q126 | ethyl | ethyl |
| Q126 | ethyl | n-propyl |
| Q126 | ethyl | isopropyl |
| Q126 | ethyl | cyclopropyl |
| Q126 | ethyl | s-butyl |
| Q126 | ethyl | n-butyl |
| Q126 | ethyl | cyclopentyl |
| Q126 | ethyl | cyclohexyl |
| Q126 | ethyl | cycloheptyl |
| Q126 | ety | phenyl |
| Q126 | ethyl | 2-chloroethyl |
| Q126 | ethyl | 2,2,2-trifluoroethyl |

TABLE 1-continued

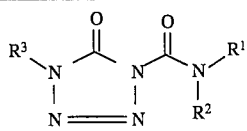

| R³ | R¹ | R² |
|---|---|---|
| Q126 | 2-chloroethyl | 2-chloroethyl |
| Q126 | n-propyl | n-propane |
| Q126 | n-propyl | isopropyl |
| Q126 | n-propyl | cyclopropyl |
| Q126 | n-propyl | s-butyl |
| Q126 | n-propyl | cyclopentyl |
| Q126 | n-propyl | cyclohexyl |
| Q126 | n-propyl | 2-chloroethyl |
| Q126 | n-propyl | 2,2,2-trifluoroethyl |
| Q126 | isopropyl | isopropyl |
| Q126 | isopropyl | cyclohexyl |
| Q126 | isopropyl | phenyl |
| Q126 | isopropyl | allyl |
| Q126 | isopropyl | 2-chloro-2-propenyl |
| Q126 | isopropyl | 2-methyl-2-propenyl |
| Q126 | isopropyl | propargyl |
| Q126 | isopropyl | 2-chloroethyl |
| Q126 | isopropyl | 2,2,2-trifluoroethyl |
| Q126 | propargyl | propargyl |
| Q126 | allyl | allyl |
| Q127 | methyl | isopropyl |
| Q127 | ethyl | ethyl |
| Q127 | ethyl | n-propyl |
| Q127 | ethyl | isopropyl |
| Q127 | ethyl | cyclopropyl |
| Q127 | ethyl | s-butyl |
| Q127 | ethyl | cyclohexyl |
| Q127 | n-propyl | isopropyl |
| Q127 | isopropyl | isopropyl |
| Q127 | isopropyl | phenyl |
| Q128 | methyl | isopropyl |
| Q128 | methyl | cyclopropyl |
| Q128 | ethyl | ethyl |
| Q128 | ethyl | isopropyl |
| Q128 | ethyl | cyclopropyl |
| Q128 | ethyl | cyclohexyl |
| Q128 | n-propyl | isopropyl |
| Q128 | isopropyl | isopropyl |
| Q128 | isopropyl | phenyl |
| Q129 | methyl | isopropyl |
| Q129 | ethyl | ethyl |
| Q129 | ethyl | n-propyl |
| Q129 | ethyl | isopropyl |
| Q129 | ethyl | cyclopropyl |
| Q129 | ethyl | s-butyl |
| Q129 | ethyl | cyclohexyl |
| Q129 | n-propyl | isopropyl |
| Q129 | isopropyl | isopropyl |
| Q129 | isopropyl | phenyl |
| Q130 | methyl | isopropyl |
| Q130 | ethyl | ethyl |
| Q130 | ethyl | isopropyl |
| Q130 | ethyl | cyclopropyl |
| Q131 | isopropyl | phenyl |
| Q131 | methyl | methyl |
| Q131 | methyl | ethyl |
| Q131 | methyl | n-propyl |
| Q131 | methyl | isopropyl |
| Q131 | methyl | cyclopropyl |
| Q131 | methyl | s-butyl |
| Q131 | methyl | t-butyl |
| Q131 | methyl | cyclopentyl |
| Q131 | methyl | cyclopropyl |
| Q131 | methyl | phenyl |
| Q131 | methyl | 2-methyl-2-propenyl |
| Q131 | ethyl | ethyl |
| Q131 | ethyl | n-propyl |
| Q131 | ethyl | isopropyl |
| Q131 | ethyl | cyclopropyl |
| Q131 | ethyl | s-butyl |
| Q131 | ethyl | cyclopentyl |

TABLE 1-continued

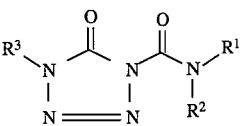

| R³ | R¹ | R² |
|---|---|---|
| Q131 | ethyl | allyl |
| Q131 | ethyl | phenyl |
| Q131 | n-propyl | isopropyl |
| Q131 | n-propyl | cyclopropyl |
| Q131 | n-propyl | s-butyl |
| Q131 | n-propyl | cyclopentyl |
| Q131 | n-propyl | cyclohexyl |
| Q131 | isopropyl | isopropyl |
| Q131 | isopropyl | cyclohexyl |
| Q131 | isopropyl | phenyl |
| Q131 | isopropyl | allyl |
| Q132 | methyl | isopropyl |
| Q132 | methyl | cyclopropyl |
| Q132 | ethyl | ethyl |
| Q132 | ethyl | isopropyl |
| Q132 | ethyl | cyclopropyl |
| Q132 | ethyl | cyclohexyl |
| Q132 | n-propyl | isopropyl |
| Q132 | isopropyl | isopropyl |
| Q132 | isopropyl | phenyl |
| Q133 | methyl | isopropyl |
| Q133 | ethyl | ethyl |
| Q133 | ethyl | isopropyl |
| Q133 | ethyl | cyclopropyl |
| Q133 | isopropyl | phenyl |
| Q134 | methyl | methyl |
| Q134 | methyl | isopropyl |
| Q134 | ethyl | ethyl |
| Q134 | ethyl | isopropyl |
| Q134 | ethyl | cyclohexyl |
| Q134 | isopropyl | isopropyl |
| Q134 | isopropyl | phenyl |
| Q135 | methyl | isopropyl |
| Q135 | ethyl | ethyl |
| Q135 | ethyl | isopropyl |
| Q135 | ethyl | cyclopropyl |
| Q135 | isopropyl | phenyl |
| Q136 | ethyl | ethyl |
| Q136 | ethyl | isopropyl |
| Q136 | ethyl | cyclopropyl |
| Q136 | isopropyl | phenyl |
| Q137 | methyl | isopropyl |
| Q137 | ethyl | ethyl |
| Q137 | ethyl | isopropyl |
| Q137 | ethyl | cyclopropyl |
| Q137 | isopropyl | phenyl |
| Q138 | methyl | isopropyl |
| Q138 | ethyl | ethyl |
| Q138 | ethyl | isopropyl |
| Q138 | ethyl | cyclopropyl |
| Q139 | methyl | isopropyl |
| Q139 | ethyl | ethyl |
| Q139 | ethyl | isopropyl |
| Q139 | ethyl | cyclopropyl |
| Q139 | ethyl | 2-chloroethyl |
| Q139 | ethyl | 2,2,2-trifluoroethyl |
| Q139 | 2-chloroethyl | 2-chloroethyl |
| Q139 | isopropyl | phenyl |
| Q140 | methyl | isopropyl |
| Q140 | ethyl | ethyl |
| Q140 | ethyl | isopropyl |
| Q141 | methyl | isopropyl |
| Q141 | ethyl | ethyl |
| Q141 | ethyl | isopropyl |
| Q141 | ethyl | cyclopropyl |
| Q141 | isopropyl | phenyl |
| Q142 | methyl | isopropyl |
| Q142 | ethyl | ethyl |
| Q142 | ethyl | isopropyl |
| Q142 | ethyl | cyclopropyl |
| Q142 | isopropyl | phenyl |

TABLE 1-continued

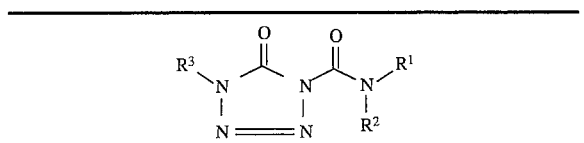

| R³ | R¹ | R² |
|---|---|---|
| Q143 | methyl | isopropyl |
| Q143 | ethyl | ethyl |
| Q143 | ethyl | isopropyl |
| Q143 | ethyl | cyclopropyl |
| Q143 | isopropyl | phenyl |
| Q144 | methyl | isopropyl |
| Q144 | ethyl | ethyl |
| Q144 | ethyl | isopropyl |
| Q144 | ethyl | cyclopropyl |
| Q144 | isopropyl | phenyl |
| Q145 | methyl | isopropyl |
| Q145 | ethyl | ethyl |
| Q145 | ethyl | isopropyl |
| Q145 | ethyl | cyclopropyl |
| Q145 | isopropyl | phenyl |
| Q146 | methyl | isopropyl |
| Q146 | ethyl | ethyl |
| Q146 | ethyl | isopropyl |
| Q146 | ethyl | cyclopropyl |
| Q146 | isopropyl | phenyl |
| Q147 | methyl | isopropyl |
| Q147 | ethyl | ethyl |
| Q147 | ethyl | isopropyl |
| Q147 | ethyl | cyclopropyl |
| Q147 | isopropyl | phenyl |
| Q148 | methyl | isopropyl |
| Q148 | ethyl | ethyl |
| Q148 | ethyl | isopropyl |
| Q148 | ethyl | cyclopropyl |
| Q148 | isopropyl | phenyl |
| Q149 | methyl | isopropyl |
| Q149 | ethyl | ethyl |
| Q149 | ethyl | isopropyl |
| Q149 | ethyl | cyclopropyl |
| Q149 | isopropyl | phenyl |
| Q150 | methyl | isopropyl |
| Q150 | ethyl | ethyl |
| Q150 | ethyl | isopropyl |
| Q150 | ethyl | cyclopropyl |
| Q150 | isopropyl | phenyl |
| Q151 | methyl | isopropyl |
| Q151 | ethyl | ethyl |
| Q151 | ethyl | isopropyl |
| Q151 | ethyl | cyclopropyl |
| Q151 | isopropyl | phenyl |
| Q152 | methyl | isopropyl |
| Q152 | ethyl | ethyl |
| Q152 | ethyl | isopropyl |
| Q152 | ethyl | cyclopropyl |
| Q152 | isopropyl | phenyl |
| Q153 | methyl | isopropyl |
| Q153 | ethyl | ethyl |
| Q153 | ethyl | isopropyl |
| Q153 | ethyl | cyclopropyl |
| Q153 | isopropyl | phenyl |
| Q154 | methyl | isopropyl |
| Q154 | ethyl | ethyl |
| Q154 | ethyl | isopropyl |
| Q154 | ethyl | cyclopropyl |
| Q154 | isopropyl | phenyl |
| Q155 | ethyl | ethyl |
| Q155 | methyl | isopropyl |
| Q156 | methyl | isopropyl |
| Q156 | ethyl | ethyl |
| Q156 | ethyl | isopropyl |
| Q157 | methyl | isopropyl |
| Q157 | ethyl | isopropyl |
| Q158 | ethyl | n-propyl |
| Q158 | n-propyl | n-propyl |
| Q158 | isopropyl | 2-chloro-2-propenyl |
| Q158 | isopropyl | 2-methyl-2-propenyl |

TABLE 1-continued

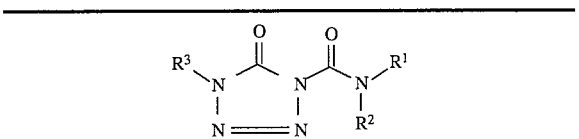

| R³ | R¹ | R² |
|---|---|---|
| Q158 | isopropyl | propargyl |
| Q158 | propargyl | propargyl |
| Q159 | ethyl | n-propyl |
| Q159 | n-propyl | n-propyl |
| Q159 | isopropyl | 2-chloro-2-propenyl |
| Q159 | isopropyl | 2-methyl-2-propenyl |
| Q159 | isopropyl | propargyl |
| Q159 | propargyl | propargyl |
| Q160 | ethyl | n-propyl |
| Q160 | n-propyl | n-propyl |
| Q160 | isopropyl | 2-chloro-2-propenyl |
| Q160 | isopropyl | 2-methyl-2-propenyl |
| Q160 | isopropyl | propargyl |
| Q160 | propargyl | propargyl |
| Q161 | ethyl | n-propyl |
| Q161 | n-propyl | n-propyl |
| Q161 | isopropyl | 2-chloro-2-propenyl |
| Q161 | isopropyl | 2-methyl-2-propenyl |
| Q161 | isopropyl | propargyl |
| Q161 | propargyl | propargyl |
| Q162 | ethyl | n-propyl |
| Q162 | n-propyl | n-propyl |
| Q162 | isopropyl | 2-chloro-2-propenyl |
| Q162 | isopropyl | 2-methyl-2-propenyl |
| Q162 | isopropyl | propargyl |
| Q162 | propargyl | propargyl |
| Q163 | methyl | isopropyl |
| Q163 | ethyl | ethyl |
| Q163 | ethyl | n-propyl |
| Q163 | ethyl | isopropyl |
| Q163 | n-propyl | n-propyl |
| Q163 | isopropyl | isopropyl |
| Q164 | methyl | isopropyl |
| Q164 | ethyl | ethyl |
| Q164 | ethyl | isopropyl |
| Q164 | isopropyl | isopropyl |
| Q165 | methyl | isopropyl |
| Q165 | ethyl | ethyl |
| Q165 | ethyl | isopropyl |
| Q165 | isopropyl | isopropyl |
| Q166 | methyl | isopropyl |
| Q166 | ethyl | ethyl |
| Q166 | ethyl | n-propyl |
| Q166 | ethyl | isopropyl |
| Q166 | ethyl | cyclopropyl |
| Q166 | ethyl | s-butyl |
| Q166 | ethyl | cyclohexyl |
| Q166 | n-propyl | isopropyl |
| Q166 | isopropyl | isopropyl |
| Q166 | isopropyl | phenyl |
| Q167 | methyl | isopropyl |
| Q167 | ethyl | ethyl |
| Q167 | ethyl | n-propyl |
| Q167 | ethyl | isopropyl |
| Q167 | ethyl | cyclopropyl |
| Q167 | ethyl | s-butyl |
| Q167 | ethyl | cyclohexyl |
| Q167 | n-propyl | isopropyl |
| Q167 | isopropyl | isopropyl |
| Q167 | isopropyl | phenyl |
| Q168 | methyl | isopropyl |
| Q168 | ethyl | ethyl |
| Q168 | ethyl | n-propyl |
| Q168 | ethyl | isopropyl |
| Q168 | ethyl | cyclopropyl |
| Q168 | ethyl | s-butyl |
| Q168 | ethyl | cyclohexyl |
| Q168 | n-propyl | isopropyl |
| Q168 | isopropyl | isopropyl |
| Q168 | isopropyl | phenyl |
| Q169 | methyl | isopropyl |

TABLE 1-continued

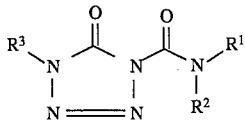

| R³ | R¹ | R² |
|---|---|---|
| Q169 | ethyl | ethyl |
| Q169 | ethyl | n-propyl |
| Q169 | ethyl | isopropyl |
| Q169 | ethyl | cyclopropyl |
| Q169 | ethyl | s-butyl |
| Q169 | ethyl | cyclohexyl |
| Q169 | n-propyl | isopropyl |
| Q169 | isopropyl | isopropyl |
| Q169 | isopropyl | phenyl |
| Q170 | methyl | isopropyl |
| Q170 | ethyl | ethyl |
| Q170 | ethyl | n-propyl |
| Q170 | ethyl | isopropyl |
| Q170 | ethyl | cyclopropyl |
| Q170 | ethyl | s-butyl |
| Q170 | ethyl | cyclohexyl |
| Q170 | n-propyl | isopropyl |
| Q170 | isopropyl | isopropyl |
| Q170 | isopropyl | phenyl |
| Q171 | methyl | isopropyl |
| Q171 | ethyl | ethyl |
| Q171 | ethyl | n-propyl |
| Q171 | ethyl | isopropyl |
| Q171 | ethyl | cyclopropyl |
| Q171 | ethyl | s-butyl |
| Q171 | ethyl | cyclohexyl |
| Q171 | n-propyl | isopropyl |
| Q171 | isopropyl | isopropyl |
| Q171 | isopropyl | phenyl |
| Q172 | methyl | isopropyl |
| Q172 | ethyl | ethyl |
| Q172 | ethyl | n-propyl |
| Q172 | ethyl | isopropyl |
| Q172 | ethyl | cyclopropyl |
| Q172 | ethyl | s-butyl |
| Q172 | ethyl | cyclopropyl |
| Q172 | n-propyl | isopropyl |
| Q172 | isopropyl | isopropyl |
| Q172 | isopropyl | phenyl |
| Q173 | methyl | isopropyl |
| Q173 | ethyl | ethyl |
| Q173 | ethyl | n-propyl |
| Q173 | ethyl | isopropyl |
| Q173 | ethyl | cyclopropyl |
| Q173 | ethyl | s-butyl |
| Q173 | ethyl | cyclohexyl |
| Q173 | n-propyl | isopropyl |
| Q173 | isopropyl | isopropyl |
| Q173 | isopropyl | phenyl |
| Q174 | methyl | isopropyl |
| Q174 | ethyl | ethyl |
| Q174 | ethyl | n-propyl |
| Q174 | ethyl | isopropyl |
| Q174 | ethyl | cyclopropyl |
| Q174 | ethyl | s-butyl |
| Q174 | ethyl | cyclohexyl |
| Q174 | n-propyl | isopropyl |
| Q174 | isopropyl | isopropyl |
| Q174 | isopropyl | phenyl |
| Q175 | methyl | isopropyl |
| Q175 | ethyl | ethyl |
| Q175 | ethyl | n-propyl |
| Q175 | ethyl | isopropyl |
| Q175 | ethyl | cyclopropyl |
| Q175 | ethyl | s-butyl |
| Q175 | ethyl | cyclohexyl |
| Q175 | n-propyl | isopropyl |
| Q175 | isopropyl | isopropyl |
| Q175 | isopropyl | phenyl |
| Q176 | methyl | isopropyl |

TABLE 1-continued

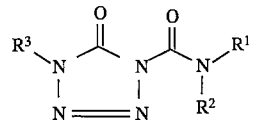

| R³ | R¹ | R² |
|---|---|---|
| Q176 | ethyl | ethyl |
| Q176 | ethyl | n-propyl |
| Q176 | ethyl | isopropyl |
| Q176 | ethyl | cyclopropyl |
| Q176 | ethyl | s-butyl |
| Q176 | ethyl | cyclohexyl |
| Q176 | n-propyl | isopropyl |
| Q176 | isopropyl | isopropyl |
| Q176 | isopropyl | phenyl |
| Q177 | methyl | isopropyl |
| Q177 | ethyl | ethyl |
| Q177 | ethyl | n-propyl |
| Q177 | ethyl | isopropyl |
| Q177 | ethyl | cyclopropyl |
| Q177 | ethyl | allyl |
| Q177 | ethyl | cyclohexyl |
| Q177 | n-propyl | isopropyl |
| Q177 | isopropyl | isopropyl |
| Q177 | isopropyl | phenyl |
| Q177 | methyl | isopropyl |
| Q177 | ethyl | ethyl |
| Q177 | ethyl | n-propyl |
| Q177 | ethyl | isopropyl |
| Q177 | ethyl | cyclopropyl |
| Q177 | ethyl | s-butyl |
| Q177 | ethyl | cyclopropyl |
| Q177 | n-propyl | isopropyl |
| Q177 | isopropyl | isopropyl |
| Q177 | isopropyl | phenyl |
| Q178 | methyl | isopropyl |
| Q178 | ethyl | ethyl |
| Q178 | ethyl | n-propyl |
| Q178 | ethyl | isopropyl |
| Q178 | ethyl | cyclopropyl |
| Q178 | ethyl | s-butyl |
| Q178 | ethyl | cyclohexyl |
| Q178 | n-propyl | isopropyl |
| Q178 | isopropyl | isopropyl |
| Q178 | isopropyl | phenyl |
| Q179 | methyl | isopropyl |
| Q179 | ethyl | ethyl |
| Q179 | ethyl | n-propyl |
| Q179 | ethyl | isopropyl |
| Q179 | ethyl | cyclopropyl |
| Q179 | ethyl | s-butyl |
| Q179 | ethyl | cyclohexyl |
| Q179 | n-propyl | isopropyl |
| Q179 | isopropyl | isopropyl |
| Q179 | isopropyl | phenyl |

TABLE 2

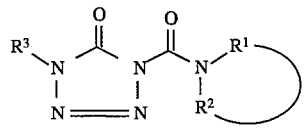

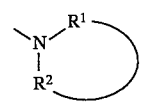

| R³ | |
|---|---|
| Q1 | 2-methylpiperidino |
| Q2 | 2,5-dimethyl-3-pyrrolin-1-yl |
| Q3 | pyrrolidin-1-yl |

TABLE 2-continued $$\begin{array}{c} R^3\text{-N} \underset{\|}{\overset{O}{\text{-}}}\text{-N} \underset{\|}{\overset{O}{\text{-}}}\text{-N} \underset{R^2}{\overset{R^1}{\diagup}} \\ \text{N} = \text{N} \end{array}$$

$$R^3\diagdown \underset{R^2}{\overset{R^1}{\text{N}\diagup}}$$

| R³ | |
|---|---|
| Q3 | piperidino |
| Q3 | 2-methylpiperidino |
| Q3 | 2,5-dimethyl-3-pyrrolin-1-yl |
| Q3 | 2-methyl-1,2,3,4-tetrahydroquinolin-1-yl |
| Q4 | 2-methylpiperidino |
| Q4 | 2,5-dimethyl-3-pyrrolin-1-yl |
| Q5 | pyrrolidin-1-yl |
| Q5 | 2-methylpiperidino |
| Q6 | piperidino |
| Q6 | 2-methylpiperidino |
| Q7 | 2-methylpiperidino |
| Q7 | 2,5-dimethyl-3-pyrrolin-1-yl |
| Q8 | pyrrolidin-1-yl |
| Q8 | piperidino |
| Q8 | morpholino |
| Q8 | 2-methylpiperidino |
| Q8 | 2,5-dimethyl-3-pyrrolin-1-yl |
| Q8 | 2,6-dimethylpiperidino |
| Q9 | pyrrolidin-1-yl |
| Q9 | piperidino |
| Q9 | morpholino |
| Q9 | 2-methylpiperidino |
| Q9 | 2,5-dimethyl-3-pyrrolin-1-yl |
| Q9 | 2,6-dimethylpiperidino |
| Q9 | 2-methyl-1,2,3,4-tetrahydroquinolin-1-yl |
| Q10 | pyrrolidin-1-yl |
| Q10 | 2-methylpiperidino |
| Q11 | 2-methylpiperidino |
| Q12 | pyrrolidin-1-yl |
| Q13 | pyrrolidin-1-yl |
| Q13 | piperidino |
| Q13 | 2-methylpiperidino |
| Q13 | 2,5-dimethyl-3-pyrrolin-1-yl |
| Q14 | pyrrolidin-1-yl |
| Q14 | piperidino |
| Q14 | morpholino |
| Q14 | 2-methylpiperidino |
| Q14 | 2,5-dimethyl-3-pyrrolin-1-yl |
| Q14 | 2,6-dimethylpiperidino |
| Q14 | 2-methyl-1,2,3,4-tetrahydroquinolin-1-yl |
| Q15 | pyrrolidin-1-yl |
| Q15 | piperidino |
| Q15 | 2-methylpiperidino |
| Q15 | 2,5-dimethyl-3-pyrrolin-1-yl |
| Q16 | 2-methylpiperidino |
| Q16 | 2,5-dimethyl-3-pyrrolin-1-yl |
| Q18 | 2-methylpiperidino |
| Q19 | 2-methylpiperidino |
| Q20 | 2,5-dimethyl-3-pyrrolin-1-yl |
| Q21 | 2-methylpiperidino |
| Q22 | 2,5-dimethyl-3-pyrrolin-1-yl |
| Q23 | pyrrolidin-1-yl |
| Q23 | piperidino |
| Q23 | morpholino |
| Q23 | 2-methylpiperidino |
| Q23 | 2,5-dimethyl-3-pyrrolin-1-yl |
| Q23 | 2,6-dimethylpiperidino |
| Q23 | 2-methyl-1,2,3,4-tetrahydroquinolin-1-yl |
| Q24 | pyrrolidin-1-yl |
| Q24 | piperidino |
| Q24 | 2-methylpiperidino |
| Q24 | 2,5-dimethyl-3-pyrrolin-1-yl |
| Q24 | 2-methyl-1,2,3,4-tetrahydroquinolin-1-yl |
| Q25 | 2-methylpiperidino |
| Q25 | 2-methyl-1,2,3,4-tetrahydroquinolin-1-yl |
| Q26 | 2-methylpiperidino |
| Q26 | 2,5-dimethyl-3-pyrrolin-1-yl |
| Q27 | 2,5-dimethyl-3-pyrrolin-1-yl |
| Q28 | 2-methylpiperidino |
| Q29 | pyrrolidin-1-yl |
| Q29 | piperidino |
| Q29 | 2-methylpiperidino |
| Q29 | 2,5-dimethyl-3-pyrrolin-1-yl |
| Q29 | 2-methyl-1,2,3,4-tetrahydroquinolin-1-yl |
| Q30 | pyrrolidin-1-yl |
| Q30 | piperidino |
| Q30 | morpholino |
| Q30 | 2-methylpiperidino |
| Q30 | 2,5-dimethyl-3-pyrrolin-1-yl |
| Q30 | 2,6-dimethylpiperidino |
| Q30 | 2-methyl-1,2,3,4-tetrahydroquinolin-1-yl |
| Q31 | pyrrolidin-1-yl |
| Q31 | piperidino |
| Q31 | 2-methylpiperidino |
| Q31 | 2,5-dimethyl-3-pyrrolin-1-yl |
| Q31 | 2-methyl-1,2,3,4-tetrahydroquinolin-1-yl |
| Q32 | 2,5-dimethyl-3-pyrrolin-1-yl |
| Q33 | 2-methylpiperidino |
| Q34 | pyrrolidin-1-yl |
| Q34 | piperidino |
| Q34 | 2-methylpiperidino |
| Q34 | 2,5-dimethyl-3-pyrrolin-1-yl |
| Q34 | 2-methyl-1,2,3,4-tetrahydroquinolin-1-yl |
| Q35 | 2-methylpiperidino |
| Q36 | 2-5-dimethyl-3-pyrrolin-1-yl |
| Q37 | 2-methylpiperidino |
| Q38 | 2-methylpiperidino |
| Q39 | 2,5-dimethyl-3-pyrrolin-1-yl |
| Q40 | 2-methylpiperidino |
| Q41 | 2-methylpiperidino |
| Q42 | 2-methylpiperidino |
| Q42 | 2,5-dimethyl-3-pyrrolin-1-yl |
| Q43 | 2-methylpiperidino |
| Q44 | 2,5-dimethyl-3-pyrrolin-1-yl |
| Q46 | 2,5-dimethyl-3-pyrrolin-1-yl |
| Q47 | pyrrolidin-1-yl |
| Q47 | 2-methylpiperidino |
| Q47 | morpholino |
| Q47 | 2-methylpiperidino |
| Q47 | 2,5-dimethyl-3-pyrrolin-1-yl |
| Q47 | 2,6-dimethylpiperidino |
| Q47 | 2-methyl-1,2,3,4-tetrahydroquinolin-1-yl |
| Q48 | 2,5-dimethyl-3-pyrrolin-1-yl |
| Q49 | pyrrolidin-1-yl |
| Q49 | piperidino |
| Q49 | morpholino |
| Q49 | 2-methylpiperidino |
| Q49 | 2,6-dimethyl-3-pyrrolin-1-yl |
| Q49 | 2,5-dimethylpiperidino |
| Q49 | 2-methyl-1,2,3,4-tetrahydroquinolin-1-yl |
| Q50 | 2-methylpiperidino |
| Q51 | 2,5-dimethyl-3-pyrrolin-1-yl |
| Q52 | 2-methylpiperidino |
| Q53 | 2,5-dimethyl-3-pyrrolin-1-yl |
| Q54 | 2-methylpiperidino |
| Q55 | 2,5-dimethyl-3-pyrrolin-1-yl |
| Q56 | pyrrolidin-1-yl |
| Q56 | piperidino |
| Q56 | 2-methylpiperidino |
| Q56 | 2,5-dimethyl-3-pyrrolin-1-yl |
| Q56 | 2-methyl-1,2,3,4-tetrahydroquinolin-1-yl |
| Q57 | pyrrolidin-1-yl |

TABLE 2-continued

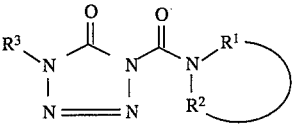

| | R³ | |
|---|---|---|
| | Q57 | piperidino |
| | Q57 | morpholino |
| | Q57 | 2-methylpiperidino |
| | Q57 | 2,5-dimethyl-3-pyrrolin-1-yl |
| | Q57 | 2,6-dimethylpiperidino |
| | Q57 | 2-methyl-1,2,3,4-tetrahydroquinolin-1-yl |
| | Q58 | 2-methylpiperidino |
| | Q58 | 2,5-dimethyl-3-pyrrolin-1-yl |
| | Q59 | pyrrolidin-1-yl |
| | Q59 | piperidino |
| | Q59 | morpholino |
| | Q59 | 2-methylpiperidino |
| | Q59 | 2,5-dimethyl-3-pyrrolin-1-yl |
| | Q59 | 2,6-dimethylpiperidino |
| | Q59 | 2-methyl-1,2,3,4-tetrahydroquinolin-1-yl |
| | Q60 | pyrrolidin-1-yl |
| | Q60 | piperidino |
| | Q60 | 2-methylpiperidino |
| | Q60 | 2,5-dimethyl-3-pyrrolin-1-yl |
| | Q60 | 2-methyl-1,2,3,4-tetrahydroquinolin-1-yl |
| | Q61 | pyrrolidin-1-yl |
| | Q61 | piperidino |
| | Q61 | morpholino |
| | Q61 | 2-methylpiperidino |
| | Q61 | 2,5-dimethyl-3-pyrrolin-1-yl |
| | Q61 | 2,6-dimethylpiperidino |
| | Q61 | 2-methyl-1,2,3,4-tetrahydroquinolin-1-yl |
| | Q62 | 2-methylpiperidino |
| | Q63 | 2,5-dimethyl-3-pyrrolin-1-yl |
| | Q64 | pyrrolidin-1-yl |
| | Q64 | piperidino |
| | Q64 | 2-methylpiperidino |
| | Q64 | 2,5-dimethyl-3-pyrrolin-1-yl |
| | Q64 | 2-methyl-1,2,3,4-tetrahydroquinolin-1-yl |
| | Q65 | 2-methylpiperidino |
| | Q65 | 2,5-dimethyl-3-pyrrolin-1-yl |
| | Q66 | 2-methylpiperidino |
| | Q67 | pyrrolidin-1-yl |
| | Q67 | piperidino |
| | Q67 | 2-methylpiperidino |
| | Q67 | 2,5-dimethyl-3-pyrrolin-1-yl |
| | Q67 | 2-methyl-1,2,3,4-tetrahydroquinolin-1-yl |
| | Q68 | 2-methylpiperidino |
| | Q69 | 2,5-dimethyl-3-pyrrolin-1-yl |
| | Q70 | 2-methylpiperidino |
| | Q71 | 2,6-dimethylpiperidino |
| | Q72 | pyrrolidin-1-yl |
| | Q72 | piperidino |
| | Q72 | 2-methylpiperidino |
| | Q72 | 2,5-dimethyl-3-pyrrolin-1-yl |
| | Q72 | 2-methyl-1,2,3,4-tetrahydroquinolin-1-yl |
| | Q73 | 2-methylpiperidino |
| | Q73 | 2,5-dimethyl-3-pyrrolin-1-yl |
| | Q74 | pyrrolidin-1-yl |
| | Q74 | piperidino |
| | Q74 | 2-methylpiperidino |
| | Q74 | 2,5-dimethyl-3-pyrrolin-1-yl |
| | Q74 | 2-methyl-1,2,3,4-tetrahydroquinolin-1-yl |
| | Q75 | 2-methylpiperidino |
| | Q75 | 2,5-dimethyl-3-pyrrolin-1-yl |
| | Q76 | 2-methylpiperidino |
| | Q77 | 2,5-dimethyl-3-pyrrolin-1-yl |
| | Q78 | pyrrolidin-1-yl |
| | Q78 | piperidino |
| | Q78 | 2-methylpiperidino |
| | Q78 | 2,5-dimethyl-3-pyrrolin-1-yl |

TABLE 2-continued

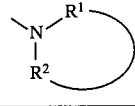

| | R³ | |
|---|---|---|
| | Q78 | 2-methyl-1,2,3,4-tetrahydroquinolin-1-yl |
| | Q79 | 2-methylpiperidino |
| | Q79 | 2,5-dimethyl-3-pyrrolin-1-yl |
| | Q80 | 2-methylpiperidino |
| | Q81 | pyrrolidin-1-yl |
| | Q81 | piperidino |
| | Q81 | 2-methylpiperidino |
| | Q81 | 2,5-dimethyl-3-pyrrolin-1-yl |
| | Q81 | 2-methyl-1,2,3,4-tetrahydroquinolin-1-yl |
| | Q82 | 2,5-dimethyl-3-pyrrolin-1-yl |
| | Q83 | pyrrolidin-1-yl |
| | Q83 | piperidino |
| | Q83 | morpholino |
| | Q83 | 2-methylpiperidino |
| | Q83 | 2,5-dimethyl-3-pyrrolin-1-yl |
| | Q83 | 2,6-dimethylpiperidino |
| | Q83 | 2-methyl,1,2,3,4-tetrahydroquinolin-1-yl |
| | Q84 | pyrrolidin-1-yl |
| | Q84 | piperidino |
| | Q84 | morpholino |
| | Q84 | 2-methylpiperidino |
| | Q84 | morpholino |
| | Q84 | 2-methylpiperidino |
| | Q84 | 2,5-dimethyl-3-pyrrolin-1-yl |
| | Q84 | 2,6-dimethylpiperidino |
| | Q84 | 2-methyl-1,2,3,4-tetrahydroquinolin-1-yl |
| | Q85 | 2-methylpiperidino |
| | Q86 | pyrrolidin-1-yl |
| | Q86 | piperidino |
| | Q86 | morpholino |
| | Q86 | 2-methylpiperidino |
| | Q86 | 2,5-dimethyl-3-pyrrolin-1-yl |
| | Q86 | 2,6-dimethylpiperidino |
| | Q86 | 2-methyl-1,2,3,4-tetrahydroquinolin-1-yl |
| | Q87 | 2-methylpiperidino |
| | Q88 | pyrrolidin-1-yl |
| | Q88 | 2-methylpiperidino |
| | Q88 | 2,5-dimethyl-3-pyrrolin-1-yl |
| | Q89 | 2,5-dimethyl-3-pyrrolin-1-yl |
| | Q90 | pyrrolidin-1-yl |
| | Q90 | piperidino |
| | Q90 | morpholino |
| | Q90 | 2-methylpiperidino |
| | Q90 | 2,5-dimethyl-3-pyrrolin-1-yl |
| | Q90 | 2,6-dimethylpiperidino |
| | Q90 | 2-methyl-1,2,3,4-tetrahydroquinolin-1-yl |
| | Q91 | pyrrolidin-1-yl |
| | Q91 | piperidino |
| | Q91 | morpholino |
| | Q91 | 2-methylpiperidino |
| | Q91 | 2,5-dimethyl-3-pyrrolin-1-yl |
| | Q91 | 2,6-dimethylpiperidino |
| | Q91 | 2-methyl-1,2,3,4-tetrahydroquinolin-1-yl |
| | Q92 | pyrrolidin-1-yl |
| | Q92 | piperidino |
| | Q92 | 2-methylpiperidino |
| | Q92 | 2,5-dimethyl-3-pyrrolin-1-yl |
| | Q92 | 2-methyl-1,2,3,4-tetrahydroquinolin-1-yl |
| | Q93 | 2-methylpiperidino |
| | Q94 | 2,5-dimethyl-3-pyrrolin-1-yl |
| | Q95 | 2-methylpiperidino |
| | Q96 | 2,5-dimethyl-3-pyrrolin-1-yl |
| | Q97 | 2-methylpiperidino |
| | Q98 | 2,5-dimethyl-3-pyrrolin-1-yl |
| | Q99 | 2-methylpiperidino |
| | Q100 | 2,5-dimethyl-3-pyrrolin-1-yl |

TABLE 2-continued

[Structure: R³-N(-N=N-)-C(=O)-N(-C(=O)-)-NR¹R² ring; and R³ / NR¹R² fragment]

| | R³ | |
|---|---|---|
| Q101 | 2,5-dimethyl-3-pyrrolin-1-yl | |
| Q102 | 2,5-dimethyl-3-pyrrolin-1-yl | |
| Q103 | 2-methylpiperidino | |
| Q104 | 2,5-dimethyl-3-pyrrolin-1-yl | |
| Q105 | pyrrolidin-1-yl | |
| Q105 | piperidino | |
| Q105 | 2-methylpiperidino | |
| Q105 | 2,5-dimethyl-3-pyrrolin-1-yl | |
| Q105 | 2-methyl-1,2,3,4-tetrahydroquinolin-1-yl | |
| Q106 | 2-methylpiperidino | |
| Q106 | 2,5-dimethyl-3-pyrrolin-1-yl | |
| Q107 | pyrrolidin-1-yl | |
| Q107 | piperidino | |
| Q107 | morpholino | |
| Q107 | 2-methylpiperidino | |
| Q107 | 2,5-dimethyl-3-pyrrolin-1-yl | |
| Q107 | 2,6-dimethylpiperidino | |
| Q107 | 2-methyl-1,2,3,4-tetrahydroquinolin-1-yl | |
| Q108 | 2-methylpiperidino | |
| Q108 | 2,5-dimethyl-3-pyrrolin-1-yl | |
| Q109 | pyrrolidin-1-yl | |
| Q109 | piperidino | |
| Q109 | morpholino | |
| Q109 | 2-methylpiperidino | |
| Q109 | 2,5-dimethyl-3-pyrrolin-1-yl | |
| Q109 | 2,6-dimethylpiperidino | |
| Q109 | 2-methyl-1,2,3,4-tetrahydroquinolin-1-yl | |
| Q110 | pyrrolidin-1-yl | |
| Q110 | piperidino | |
| Q110 | 2-methylpiperidino | |
| Q110 | 2,5-dimethyl-3-pyrrolin-1-yl | |
| Q110 | 2-methyl-1,2,3,4-tetrahydroquinolin-1-yl | |
| Q110 | 2-methylpiperidino | |
| Q111 | 2,5-dimethyl-3-pyrrolin-1-yl | |
| Q112 | pyrrolidin-1-yl | |
| Q112 | piperidino | |
| Q112 | morpholino | |
| Q112 | 2-methylpiperidino | |
| Q112 | 2,5-dimethyl-3-pyrrolin-1-yl | |
| Q112 | 2,6-dimethylpiperidino | |
| Q112 | 2-methyl-1,2,3,4-tetrahydroquinolin-1-yl | |
| Q113 | pyrrolidin-1-yl | |
| Q113 | piperidino | |
| Q113 | 2-methylpiperidino | |
| Q113 | 2,5-dimethyl-3-pyrrolin-1-yl | |
| Q113 | 2-methyl-1,2,3,4-tetrahydroquinolin-1-yl | |
| Q114 | pyrrolidin-1-yl | |
| Q114 | piperidino | |
| Q114 | morpholino | |
| Q114 | 2-methylpiperidino | |
| Q114 | 2,5-dimethyl-3-pyrrolin-1-yl | |
| Q114 | 2,6-dimethylpiperidino | |
| Q114 | 2-methyl-1,2,3,4-tetrahydroquinolin-1-yl | |
| Q115 | pyrrolidin-1-yl | |
| Q115 | piperidino | |
| Q115 | morpholino | |
| Q115 | 2-methylpiperidino | |
| Q115 | 2,5-dimethyl-3-pyrrolin-1-yl | |
| Q115 | 2,6-dimethylpiperidino | |
| Q115 | 2-methyl-1,2,3,4-tetrahydroquinolin-1-yl | |
| Q116 | pyrrolidin-1-yl | |
| Q116 | piperidino | |
| Q116 | morpholino | |
| Q116 | 2-methylpiperidino | |
| Q116 | 2,5-dimethyl-3-pyrrolin-1-yl | |
| Q116 | 2,6-dimethylpiperidino | |
| Q116 | 2-methyl-1,2,3,4-tetrahydroquinolin-1-yl | |
| Q117 | pyrrolidin-1-yl | |
| Q117 | piperidino | |
| Q117 | morpholino | |
| Q117 | 2-methylpiperidino | |
| Q117 | 2,5-dimethyl-3-pyrrolin-1-yl | |
| Q117 | 2,6-dimethylpiperidino | |
| Q117 | 2-methyl-1,2,3,4-tetrahydroquinolin-1-yl | |
| Q118 | pyrrolidin-1-yl | |
| Q118 | piperidino | |
| Q118 | morpholino | |
| Q118 | 2-methylpiperidino | |
| Q118 | 2,5-dimethyl-3-pyrrolin-1-yl | |
| Q118 | 2,6-dimethylpiperidino | |
| Q118 | 2-methyl-1,2,3,4-tetrahydroquinolin-1-yl | |
| Q119 | pyrrolidin-1-yl | |
| Q119 | piperidino | |
| Q119 | 2-methylpiperidino | |
| Q119 | 2,5-dimethyl-3-pyrrolin-1-yl | |
| Q119 | 2-methyl-1,2,3,4-tetrahydroquinolin-1-yl | |
| Q120 | pyrrolidin-1-yl | |
| Q120 | piperidino | |
| Q120 | morpholino | |
| Q120 | 2-methylpiperidino | |
| Q120 | 2,5-dimethyl-3-pyrrolin-1-yl | |
| Q120 | 2,6-dimethylpiperidino | |
| Q120 | 2-methyl-1,2,3,4-tetrahydroquinolin-1-yl | |
| Q121 | pyrrolidin-1-yl | |
| Q121 | piperidino | |
| Q121 | morpholino | |
| Q121 | 2-methylpiperidino | |
| Q121 | 2,5-dimethyl-3-pyrrolin-1-yl | |
| Q121 | 2,6-dimethylpiperidino | |
| Q121 | 2-methyl-1,2,3,4-tetrahydroquinolin-1-yl | |
| Q122 | pyrrolidin-1-yl | |
| Q122 | piperidino | |
| Q122 | 2-methylpiperidino | |
| Q122 | 2,5-dimethyl-3-pyrrolin-1-yl | |
| Q122 | 2-methyl-1,2,3,4-tetrahydroquinolin-1-yl | |
| Q123 | 2-methylpiperidino | |
| Q123 | 2,5-dimethyl-3-pyrrolin-1-yl | |
| Q124 | pyrrolidin-1-yl | |
| Q124 | piperidino | |
| Q124 | 2-methylpiperidino | |
| Q124 | 2,5-dimethyl-3-pyrrolin-1-yl | |
| Q124 | 2-methyl-1,2,3,4-tetrahydroquinolin-1-yl | |
| Q125 | pyrrolidin-1-yl | |
| Q125 | piperidino | |
| Q125 | morpholino | |
| Q125 | 2-methylpiperidino | |
| Q125 | 2,5-dimethyl-3-pyrrolin-1-yl | |
| Q125 | 2,6-dimethylpiperidino | |
| Q125 | 2-methyl-1,2,3,4-tetrahydroquinolin-1-yl | |
| Q126 | pyrrolidin-1-yl | |
| Q126 | 2-5-dimethyl-3-pyrrolin-1-yl | |
| Q126 | piperidino | |
| Q126 | 5-methyl-2-pyrrolin-1-yl | |
| Q126 | morpholino | |
| Q126 | 2-methylpiperidino | |
| Q126 | 2,5-dimethyl-3-pyrrolin-1-yl | |
| Q126 | 2,5-dimethyl-3-pyrrolin-1-yl | |
| Q126 | 2,6-dimethylpiperidino | |
| Q126 | 2-methyl-1,2,3,4-tetrahydroquinolin-1-yl | |
| Q126 | perhydroquinolin-1-yl | |
| Q126 | perhydroquinolin-1-yl | |
| Q127 | 2-methylpiperidino | |

TABLE 2-continued

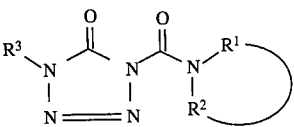

| | |
|---|---|
| Q127 | 2,5-dimethyl-3-pyrrolin-1-yl |
| Q128 | pyrrolidin-1-yl |
| Q128 | piperidino |
| Q128 | 2-methylpiperidino |
| Q128 | 2,5-dimethyl-3-pyrrolin-1-yl |
| Q128 | 2-methyl-1,2,3,4-tetrahydroquinolin-1-yl |
| Q129 | 2-methylpiperidino |
| Q129 | 2,5-dimethyl-3-pyrrolin-1-yl |
| Q129 | 2-methylpiperidino |
| Q131 | pyrrolidin-1-yl |
| Q131 | piperidino |
| Q131 | morpholino |
| Q131 | 2-methylpiperidino |
| Q131 | 2,5-dimethyl-3-pyrrolin-1-yl |
| Q131 | 2,6-dimethylpiperidino |
| Q131 | 2-methyl-1,2,3,4-tetrahydroquinolin-1 |
| Q132 | pyrrolidin-1-yl |
| Q132 | piperidino |
| Q132 | 2-methylpiperidino |
| Q132 | 2,5-dimethyl-3-pyrrolin-1-yl |
| Q132 | 2-methyl-1,2,3,4-tetrahydroquinolin-1-yl |
| Q133 | 2-methylpiperidino |
| Q134 | 2,5-dimethyl-3-pyrrolin-1-yl |
| Q135 | 2-methylpiperidino |
| Q136 | 2-methylpiperidino |
| Q136 | 2-methylpiperidino |
| Q137 | 2,5-dimethyl-3-pyrrolin-1-yl |
| Q138 | 2-methylpiperidino |
| Q138 | 2,5-dimethyl-3-pyrrolin-1-yl |
| Q139 | 2-methylpiperidino |
| Q139 | 2,5-dimethyl-3-pyrrolin-1-yl |
| Q140 | 2-methylpiperidino |
| Q140 | 2,5-dimethyl-3-pyrrolin-1-yl |
| Q141 | 2-methylpiperidino |
| Q141 | 2,5-dimethyl-3-pyrrolin-1-yl |
| Q142 | 2-methylpiperidino |
| Q142 | 2,5-dimethyl-3-pyrrolin-1-yl |
| Q143 | 2-methylpiperidino |
| Q143 | 2,5-methyl-3-pyrrolin-1-yl |
| Q144 | 2-methylpiperidino |
| Q144 | 2,5-dimethyl-3-pyrrolin-1-yl |
| Q145 | 2-methylpiperidino |
| Q145 | 2,5-dimethyl-3-pyrrolin-1-yl |
| Q146 | 2-methylpiperidino |
| Q146 | 2,5-dimethyl-3-pyrrolin-1-yl |
| Q147 | 2-methylpiperidino |
| Q147 | 2,5-dimethyl-3-pyrrolin-1-yl |
| Q148 | 2-methylpiperidino |
| Q148 | 2,5-dimethyl-3-pyrrolin-1 |
| Q149 | 2-methylpiperidino |
| Q149 | 2,5-dimethyl-3-pyrrolin-1-yl |
| Q150 | 2-methylpiperidino |
| Q150 | 2,5-dimethyl-3-pyrrolin-1-yl |
| Q151 | 2-methylpiperidino |
| Q151 | 2,5-dimethyl-3-pyrrolin-1-yl |
| Q152 | 2-methylpiperidino |
| Q152 | 2,5-dimethyl-3-pyrrolin-1-yl |
| Q153 | 2-methylpiperidino |
| Q153 | 2,5-dimethyl-3-pyrrolin-1-yl |
| Q154 | 2-methylpiperidino |
| Q154 | 2,5-dimethyl-3-pyrrolin-1-yl |
| Q155 | 2-methylpiperidino |
| Q155 | 2-5-dimethyl-3-pyrrolin-1-yl |
| Q156 | 2-methylpiperidino |
| Q156 | 2,5-dimethyl-3-pyrrolin-1-yl |
| Q157 | 2-methylpiperidino |

TABLE 2-continued

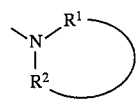

| | |
|---|---|
| Q157 | 2,5-dimethyl-3-pyrrolin-1-yl |
| Q158 | 2,5-dimethyl-3-pyrrolin-1-yl |
| Q158 | 2-methylpiperidino |
| Q159 | 2,5-dimethyl-3-pyrrolin-1-yl |
| Q159 | 2-methylpiperidino |
| Q160 | 2,5-dimethyl-3-pyrrolin-1-yl |
| Q161 | 2,5-dimethyl-3-pyrrolin-1-yl |
| Q161 | 2-methylpiperidino |
| Q162 | 2,5-dimethyl-3-pyrrolin-1-yl |
| Q163 | 2,5-dimethyl-3-pyrrolin-1-yl |
| Q163 | 2-methylpiperidino |
| Q164 | 2,5-dimethyl-3-pyrrolin-1-yl |
| Q165 | 2,5-dimethyl-3-pyrrolin-1-yl |
| Q165 | 2-methylpiperidino |
| Q166 | 2-methylpiperidino |
| Q166 | 2,5-dimethyl-3-pyrrolin-1-yl |
| Q167 | 2-methylpiperidino |
| Q167 | 2,5-dimethyl-3-pyrrolin-1-yl |
| Q168 | 2-methylpiperidino |
| Q168 | 2,5-dimethyl-3-pyrrolin-1-yl |
| Q169 | 2-methylpiperidino |
| Q169 | 2,5-dimethyl-3-pyrrolin-1-yl |
| Q170 | 2-methylpiperidino |
| Q170 | 2,5-dimethyl-3-pyrrolin-1-yl |
| Q171 | 2-methylpiperidino |
| Q171 | 2,5-dimethyl-3-pyrrolin-1-yl |
| Q172 | 2-methylpiperidino |
| Q172 | 2,5-dimethyl-3-pyrrolin-1-yl |
| Q173 | 2-methylpiperidino |
| Q173 | 2,5-dimethyl-3-pyrrolin-1-yl |
| Q174 | 2-methylpiperidino |
| Q174 | 2,5-dimethyl-3-pyrrolin-1-yl |
| Q175 | 2-methylpiperidino |
| Q175 | 2,5-dimethyl-3-pyrrolin-1-yl |
| Q176 | 2-methylpiperidino |
| Q176 | 2,5-dimethyl-3-pyrrolin-1-yl |
| Q177 | 2-methylpiperidino |
| Q177 | 2,5-dimethyl-3-pyrrolin-1-yl |
| Q178 | 2-methylpiperidino |
| Q178 | 2,5-dimethyl-3-pyrrolin-1-yl |
| Q179 | 2-methylpiperidino |
| Q179 | 2,5-dimethyl-3-pyrrolin-1-yl |

If use is made, in the above-mentioned process a), of 1-(5-chloro-1,3-dimethyl-4-pyrazolyl)-5(4H)-tetrazolinone and diethylcarbamoyl chloride as starting materials, for example, the reaction can be expressed as follows:

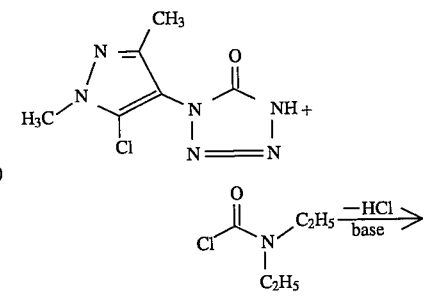

-continued

[Structure: pyrazole with CH3, N-N-H3C, Cl substituents connected via N to C(=O)-N(N=N)-C(=O)-N(C2H5)(C2H5)]

If use is made, in the above-mentioned process b), of 1-(1-benzyl-2,5-dimethyl-3-pyrrolyl)-4-(N,N-diethylcarbamoyl)-5(4H)-tetrazolinone and hydrogen gas as starting materials, for example, the reaction can be expressed as follows:

[Structure: benzyl-pyrrolyl-tetrazolinone starting material]

$$\xrightarrow{H_2 \text{ palladium catalyst}}$$

[Structure: product with HN-pyrrolyl and toluene byproduct]

In the above-mentioned process a), the starting compounds of the formula (II) are those having the substituents $R^3$ set forth hereinabove, preferably those having the preferred substituents $R^3$ set forth herinabove.

The compounds of the formula (II), are new compounds, and the present invention extends to said compounds and also to processes for producing them.

The compounds of the formula (II) can be synthesized by the following processes.

Process c):

Reaction of a compound represented by the formula $$R^3-\overset{O}{\underset{\|}{C}}-Cl \quad (V)$$

wherein $R^3$ has the same meanings as defined above, with trimethylsilylazide or Process d):

Reaction of a compound represented by the formula $$R-^{(-3)}-NCO \quad (VI)$$

wherein $R^3$ has the same meanings as defined above, with trimethylsilylazide or Process e):

Reaction of a compound represented by the formula $$R^3\underset{H}{\overset{O}{\underset{\|}{N}}}\overset{}{-}O-C_6H_5 \quad (VII)$$

wherein $R^3$ has the same meanings as defined above, with sodium azide.

In the above-mentioned process c), the starting compounds of the formula (V) have the substituents defined hereinabove for $R^3$, preferably the preferred substituents defined hereinabove.

The compounds of the formula (V) are well known compounds in the field of organic chemistry (being sold generally as a reagent) and the following compounds, for example, can be mentioned:

2-furoyl chloride,
2-thenoyl chloride,
3-chloro-2-thenoyl chloride,
3,5-dimethylisoxazole-4-carbonyl chloride, and
5-methylisoxazole-3-carbonyl chloride.

The compounds of the formula (V) can also easily be obtained by chlorinating in a usual manner the compounds represented by the formula $$R^3-\overset{O}{\underset{\|}{C}}-OH \quad (VIII)$$

wherein $R^3$ has the same meanings as defined above.

The compounds represented by the formula (VIII) are well known compounds in the field of organic chemistry. Said compounds are described, for example, in Patents DE3013908-A, DE3713774-A, EP-199675-A, EP-262873-A, EP-306868-A, EP-371950-A, EP-371594-A, EP-372470-A, EP-442430-A, EP-538231-A, EP-550111-A, EP-555153-A, EP-570706-A, EP-538231-A, ES2005136-A, FR-1535810, JP Hei.1-61463-A, JP Hei.2-42061-A, JP Hei.2-53776-A, JP Hei.2-129171-A, JP Hei.3-56478-A, JP Hei.4-120005-A, JP Hei.4-120059-A, JP Hei.5-59024-A, NL6607796, U.S. Pat. Nos. 3,271,407, 3,294,783, 4,226,877, 4,785,012, 5,201,938, 5,276,025, WO9308155-A, WO9311117-A, WO9314083-A, etc., as well as in scientific journals such as Acta. Chem. Scand., 24 (9), 3107–15, (1970), Agric. Biol. Chem., 48 (1), 45, (1984), Angew. Chem., 104 (6), 758–9, Arch. Pharm. (Weinheim, Ger.), 325 (2), 83–7, (1992), Boll. Chim. Farm., 119 (12), 725–30, (1980), Bull. Soc. Chim. Fr. (1), 242–5, (1971), Chem. Lett. (4) 585–8 (1991), Chem. Scr., 16 (1–2), 38–41, (1980), do. 16 (4), 117–121, (1980), Eur. J. Med. Chem., 27 (6), 581–93, (1992), Heterocycles, 23 (6), 1431–5, (1985), do. 29 (4), 667–677 (1989), Indian J. Chem., Sect B, 17B (3), 222, (1979), J. Am. Chem. Soc., 89 (21), 5461–2, (1967), do. 114 (23), 8783–94 (1992), J. Chem. Soc. C., (2), 172–85, (1968), do. (2), 172–85, (1968), J. Chem. Soc., Perkin Trans. 1, (4), 791–4 (1983), do. (7), 1875–9, (1988), do. (6), 1139–45, (1989), do. (10), 2417–28 (1991), do. (10), 2600–2601, (1991), do. (2), 215–19, (1992), J. Chin. Chem. Soc. (Taipei), 39 (4), 319–23, (1992), J. Heterocycl. Chem., 14 (5), 725–8, (1977), do. 19 (3), 561–6 (1982), do. 22 (6), 1621–30, (1985), do. 28 (4), 1003, (1991), J. Org. Chem., 42 (20), 3230–3, (1977), do. 50 (26), 5660–6, (1985), Kenkyu Hokoku-Asahi Garasm, 60, 167–174, Khim. Geterotsikl. Soedin., (8), 1024–1025, (1973), Mohatsh. Chem., 114 (2), 249–25, (1983), Symth. Commun., 24 (1), 95–101, Systhesis (1), 69–70, (1986), do. (9), 753–5, (1986), do. (11), 829–30, (1978), do. (10), 767–71, (1988), Tetrahedron, 27 (15), 3307–15 (1971), do. 32 (4), 507–13, (1976), Tetrahedron Lett., 26 (14), 1777, (1985), Zh. Obsch. Khim., 52 (11), 2529, (1982), Zh. Org. Kim., 26 (7), 1560–6, (1990), J. Pesticide Sci. 18 (3), 245–51, (1993), Journal of Pharmacy 90 (1), 32–5, (1970), etc., or are sold generally as a reagent and, as examples of said compounds, there may be mentioned the following compounds:

3-furoic acid,
3-chloro-2-furoic acid,
3-methyl-2-furoic acid,
3-methoxy-2-furoic acid,
2-methyl-3-furoic acid,
2-chloro-3-furoic acid,
2-methyl-4-trifluoromethyl-3-furoic acid,
2,4-dimethyl-3-furoic acid,
2,5-dimethyl-3-furoic acid,
3-thenoic acid,
2-methyl-3-thenoic acid,
2-methyl-4-methoxy-3-thenoic acid,
4-fluoro-3-thenoic acid,
4-methyl-3-thenoic acid,
5-trifluoromethyl-2-thenoic acid,
5-chloro-3-methoxy-2-thenoic acid,
3-fluoro-2-thenoic acid,
3,4,5-trichloro-2-thenoic acid,
2-methoxy-3-thenoic acid,
4-chloro-2-methyl-3-thenoic acid,
2-chloro-3-thenoic acid,
4-chloro-3-thenoic acid,
3-methoxy-2-thenoic acid,
3-methylthio-2-thenoic acid,
3-methyl-2-thenoic acid,
2-chloro-4-methyl-3-thenoic acid,
2-methyl-3-thenoic acid,
2,4,5-trimethyl-3-thenoic acid,
5-chloro-2-thenoic acid,
2,5-dimethyl-3-thenoic acid,
1-methyl-2-pyrrolecarboxylic acid,
1,3-dimethyl-2-pyrrolecarboxylic acid,
1,2-dimethyl-3-pyrrolecarboxylic acid,
5-chloro-1-methyl-2-pyrrolecarboxylic acid,
1-benzyl-2,5-dimethyl-3-pyrrolecarboxylic acid,
4-methyl-5-oxazolecarboxylic acid,
2,4-dimethyl-5-oxazolecarboxylic acid,
5-chloro-2-methyl-4-oxazolecarboxylic acid,
2,5-dimethyl-4-oxazolecarboxylic acid,
4-ethoxy-2-methyl-5-oxazolecarboxylic acid,
5-methyl-4-oxazolecarboxylic acid,
2-methyl-5-oxazolecarboxylic acid,
5-oxazolecarboxylic acid,
3,5-dimethyl-4-isoxazolecarboxylic, acid,
3-isoxazolecarboxylic acid,
5-chloro-3-methyl-4-isoxazolecarboxylic acid,
5-methyl-3-isoxazolecarboxylic acid,
3-methyl-5-isoxazolecarboxylic acid,
4-isoxazolecarboxylic acid,
3-methoxy-5-isoxazolecarboxylic acid,
3-isoxazolecarboxylic acid,
3-chloro-5-isoxazolecarboxylic acid,
3-methyl-4-isoxazolecarboxylic acid,
3-ethyl-5-methyl-4-isoxazolecarboxylic acid,
3-ethoxy-5-methyl-4-isoxazolecarboxylic acid,
3-chloro-5-methyl-4-isoxazolecarboxylic acid,
5-methyl-4-isoxazolecarboxylic acid,
3-methyl-5-methoxy-4-isoxazolecarboxylic acid,
4-chloro-3-methyl-5-isoxazolecarboxylic acid,
3,4-dichloro-5-isoxazolecarboxylic acid,
5-cyclopropyl-4-isoxazolecarboxylic acid,
3-bromo-5-methyl-4-isoxazolecarboxylic acid,
4,5-dimethyl-3-isoxazolecarboxylic acid,
3-methyl-5-isopropyl-4-isoxazolecarboxylic acid
3,4-dimethyl-5-isoxazolecarboxylic acid,
4-thiazolecarboxylic acid,
5-thiazolecarboxylic acid,
2-thiazolecarboxylic acid,
3-methyl-5-thiazolecarboxylic acid,
2-chloro-4-methyl-5-thiazolecarboxylic acid,
2,4-dichloro-5-thiazolecarboxylic acid,
2,4-dimethyl-5-thiazolecarboxylic acid,
2-methyl-4-thiazolecarboxylic acid,
2-methyl-4-trifluoromethyl-5-thiazolecarboxylic acid,
2,5-dichloro-4-thiazolecarboxylic acid,
2,5-dimethyl-4-thiazolecarboxylic acid,
4-methyl-2-methoxy-5-thiazolecarboxylic acid,
5-methyl-4-thiazolecarboxylic acid,
3-chloro-5-methoxy-4-isothiazolecarboxylic acid,
3,5-dichloro-4-isothiazolecarboxylic acid,
3-isothiazolecarboxylic acid,
3,5-dimethylthio-4-isothiazolecarboxylic acid,
4-methyl-5-isothiazolecarboxylic acid,
3-methyl-4-isothiazolecarboxylic acid,
5-isothiazolecarboxylic acid,
5-chloro-3-methyl-4-isothiazolecarboxylic acid,
3,5-dimethyl-4-isothiazolecarboxylic acid,
3,4-dichloro-5-isothiazolecarboxylic acid,
3-methoxy-4-isothiazolecarboxylic acid,
3-methyl-5-isothiazolecarboxylic acid,
4,5-dichloro-3-isothiazolecarboxylic acid,
4-chloro-5-isothiazolecarboxylic acid,
4-chloro-3-methyl-5-isothiazolecarboxylic acid,
4-isothiazolecarboxylic acid,
1-methyl-2-imidazolecarboxylic acid,
1-benzyl-2-imidazolecarboxylic acid,
1-methyl-4-imidazolecarboxylic acid,
1-methyl-5-imidazolecarboxylic acid,
1,2-dimethyl-5-imidazolecarboxylic acid,
1,4-dimethyl-5-imidazolecarboxylic acid,
1,5-dimethyl-4-imidazolecarboxylic acid,
1-methyl-4-methylthio-5-imidazolecarboxylic acid,
1,3,5-trimethyl-4-pyrazolecarboxylic acid,
1,4-dimethyl-3-pyrazolecarboxylic acid,
4-chloro-1-methyl-5-pyrazolecarboxylic acid,
4-chloro-1-methyl-3-pyrazolecarboxylic acid,
1,3-dimethyl-4-pyrazolecarboxylic acid,
5-fluoro-1-methyl-3-trifluoromethyl-4-pyrazolecarboxylic acid
3-chloro-1-methyl-4-pyrazolecarboxylic acid,
5-chloro-3-ethyl-1-methyl-4-pyrazolecarboxylic acid,
1,3-dimethyl-5-methoxy-4-pyrazolecarboxylic acid,
1,3-dimethyl-5-methylthio-4-pyrazolecarboxylic acid,
4-chloro-3-ethyl-1-methyl-5-pyrazolecarboxylic acid,
4-chloro-1-methyl-3-trifluoromethyl-5-pyrazolecarboxylic acid
1-methyl-3-trifluoromethyl-5-pyrazolecarboxylic acid,
3,5-dichloro-1-methyl-4-pyrazolecarboxylic acid,
4-chloro-1,3-dimethyl-5-pyrazolecarboxylic acid,
1-methyl-3-methoxy-4-pyrazolecarboxylic acid,
1-methyl-3-trifluoromethyl-5-pyrazolecarboxylic acid,
1-methyl-5-methoxy-4-pyrazolecarboxylic acid,
1-ethyl-3,5-dimethyl-4-pyrazolecarboxylic acid,
5-chloro-1,3-dimethyl-4-pyrazolecarboxylic acid,
1,5-dimethyl-4-pyrazolecarboxylic acid,
4-chloro-1,3-dimethyl-5-pyrazolecarboxylic acid,
5-chloro-1-methyl-4-pyrazolecarboxylic acid,
1-methyl-5-pyrazolecarboxylic acid,
1,4-dimethyl-5-pyrazolecarboxylic acid,
1,3-dimethyl-5-pyrazolecarboxylic acid,
1-methyl-4-pyrazolecarboxylic acid,
4-chloro-1,5-dimethyl-3-pyrazolecarboxylic acid,
1-benzyl-3,5-dimethyl-4-pyrazolecaboxylic acid.

The reaction of the above-mentioned process c) can be carried out in a manner similar to the synthesis of tetrazolinones described in Journal of the Chemical Society, Perkin Transactions 1, 1992, pages 1101–1104, or The Journal of American Chemical Society, Vol. 81, 1959, pages 3076–3079.

In the above-mentioned process d), the starting compounds of the formula (VI), have the substituents defined hereinabove for $R^3$, preferably having the preferred substituents defined hereinabove for $R^3$.

The compounds of the formula (VI) are well known compounds in the field of organic chemistry and are described, for example, in Patents AT352745, JP Sho. 60-72889-A, JP Sho.61-167675-A, WO 82/04047-A, EP-13817, U.S. Pat. No. 4,863,947, etc. as well as in the scientific journals such as J. Chem. Soc., Perkin Trans. 1, 1992, pages 1101–1104, Chem. Ber. Vol. 89, page 1473, 1956, Chem. Pharm. Bull. Vol. 29, page 237, 1981, J. Heterocyle. Chem. Vol. 28, page 1003, 1991, etc. As examples of said compounds, there may be mentioned the following compounds:

2-chloro-3-isocyanato-4-methylthiophene,
2-isocyanato-3-methylthiophene,
3-isocyanatothiophene,
3-furoylisocyanate,
2-isocyanatothiophene,
2,5-dichloro-4-isocyanatothiazole,
2-chloro-5-trifluoromethyl-4-isocyanatothiazole,
4-isocyanato-3,5-dimethylisoxazole,
3-isocyanato-4-phenyl-1,2,5-oxadiazole,
3-isocyanato-4-(4-chlorophenyl)-1,2,5-oxadiazole,
2-isocyanato-5-tert-butyl-1,3,4-thiadiazole,
5-isocyanato-(1H)-tetrazole.

Said compounds of the formula (VI) can also easily be prepared by Curtius rearrangement of the compounds represented by the above-mentioned formula (VIII) or by Schmidt rearrangement of the compounds

$$R{-}^{(-3)}{-}NH_2 \qquad (IX)$$

wherein $R^3$ has the same meaning as defined above.

The reactions of the above-mentioned processes can be carried out as described in Chem. Rev. Vol. 72, pages 457–496 (1972) or in a manner similar thereto.

In the above-mentioned process, the compounds of the formula (IX) have the substituents defined hereinabove for $R^3$, preferably the preferred substituents defined hereinabove for $R^3$.

The compounds represented by the formula (IX) are well known compounds in the field of organic chemistry (being sold generally as reagent) and, as examples of said compounds, there may be mentioned the following compounds:

5-amino-3-methylisoxazole,
3-amino-5-methylisoxazole,
2-aminothiazole,
5-amino-3-methylisothiazole,
4-amino-1,2,3-oxadiazole,
1-methyl-5-amino-1,2,4-triazole,
2-amino-1,3,4-oxadiazole,
5-amino-1,2,4-thiadiazole,
3-amino-1,2,4-oxadiazole,
5-amino-1,2,3-thiadiazole,
5-amino-1-benzyl-1,2,3-triazole.

The reaction of the process d) can be carried out in a manner similar to the synthesis—of tetrazolinones described in J. Org. Chem. Vol. 45, pages 5130–5136, 1980 or J. Am. Chem. Soc. Vol. 81, pages 3076–3079, 1959.

In the above-mentioned process e), the starting compounds of the formula (VII) have the substituents defined before hereinabove for $R^3$, preferably the preferred substituents defined hereinabove for $R^3$.

The compounds of the formula (VII) can be prepared easily by the following known process.

Process (f)

Reacting a compound represented by the above-mentioned formula (IX) with phenylchloroformate.

The above-mentioned process (f) can be carried out in the same manner as or in a manner similar to the method described in Japanese Patent Laid-Open Application Sho 54 (1979)-73777;

In the above-mentioned process (a), as examples of the compounds of the formula (II), there may be mentioned the following compounds:

1-(2-thienyl)-5(4H)-tetrazolinone,
1-(3-thienyl)-5(4H)-tetrazolinone,
1-(2-furyl)-5(4H)-tetrazolinone,
1-(3-furyl)-5(4H)-tetrazolinone,
1-(3-chloro-2-furyl)-5(4H)-tetrazolinone,
1-(3-methyl-2-furyl)-5(4H)-tetrazolinone,
1-(3-methoxy-2-furyl)-5(4H)-tetrazolinone,
1-(2-methyl-3-furyl)-5(4H)-tetrazolinone,
1-(2-chloro-3-furyl)-5(4H)-tetrazolinone,
1-(2-methyl-4-trifluoromethyl-3-furyl)-5(4H)-tetrazolinone,
1-(2,4-dimethyl-3-furyl)-5(4H)-tetrazolinone,
1-(2,5-dimethyl-3-furyl)-5(4H)-tetrazolinone,
1-(2-methyl-3-thienyl)-5(4H)-tetrazolinone,
1-(2-methyl-4-methoxy-3-thienyl)-5(4H)-tetrazolinone,
1-(4-fluoro-3-thienyl)-5(4H)-tetrazolinone,
1-(4-methyl-3-thienyl)-5(4H)-tetrazolinone,
1-(5-trifluoromethyl-2-thienyl)-5(4H)-tetrazolinone,
1-(5-chloro-3-methoxy-2-thienyl)-5(4H)-tetrazolinone,
1-(3-fluoro-2-thienyl)-5(4H)-tetrazolinone,
1-(3,4,5-trichloro-2-thienyl)-5(4H)-tetrazolinone,
1-(2-methoxy-3-thienyl)-5(4H)-tetrazolinone,
1-(4-chloro-2-methyl-3-thienyl)-5(4H)-tetrazolinone,
1-(chloro-3-thienyl)-5(4H)-tetrazolinone,
1-(4-chloro-3-thienyl)-5(4H)-tetrazolinone,
1-(3-chloro-2-thienyl)-5(4H)-tetrazolinone,
1-(3-methoxy-2-thienyl)-5(4H)-tetrazolinone,
1-(3-methylthio-2-thienyl)-5(4H)-tetrazolinone,
1-(3-methyl-2-thienyl)-5(4H)-tetrazolinone,
1-(2-chloro-4-methyl-3-thienyl)-5(4H)-tetrazolinone,
1-(2,4,5-trimethyl-3-thienyl)-5(4H)-tetrazolinone,
1-(5-chloro-3-thienyl)-5(4H)-tetrazolinone,
1-(2,5-dimethyl-3-thienyl)-5(4H)-tetrazolinone,
1-(1-methyl-2-pyrrolyl)-5(4H)-tetrazolinone,
1-(1,3-dimethyl-2-pyrrolyl)-5(4H)-tetrazolinone,
1-(1,2-dimethyl-3-pyrrolyl)-5(4H)-tetrazolinone,
1-(5-chloro-1-methyl-2-pyrrolyl)-5(4H)-tetrazolinone,
1-(1-benzyl-2,5-dimethyl-3-pyrrolyl)-5(4H)-tetrazolinone,
1-(4-methyl-5-oxazolyl)-5(4H)-tetrazolinone,
1-(2,4-dimethyl-5-oxazolyl)-5(4H)-tetrazolinone,
1-(5-chloro-2-methyl-4-oxazolyl)-5(4H)-tetrazolinone,
1-(2,5-dimethyl-4-oxazolyl)-5(4H)-tetrazolinone,
1-(4-ethoxy-2-methyl-5-oxazolyl)-5(4H)-tetrazolinone,
1-(5-methyl-4-oxazolyl)-5(4H)-tetrazolinone,
1-(5-methyl-2-oxazolyl)-5(4H)-tetrazolinone,
1-(5-oxazolyl)-5(4H)-tetrazolinone,
1-(3-isoxazolyl)-5(4H)-tetrazolinone,
1-(5-chloro-3-methyl-4-isoxazolyl)-5(4H)-tetrazolinone,
1-(4-isoxazolyl)-5(4H)-tetrazolinone,
1-(3-methoxy-5-isoxazolyl)-5(4H)-tetrazolinone,
1-(3-chloro-5-isoxazolyl)-5(4H)-tetrazolinone, 1-(3-methyl-4-isoxazolyl)-5(4H)-tetrazolinone,
1-(3-ethyl-5-methyl-4-isoxazolyl)-5(4H)-tetrazolinone,
1-(3-ethoxy-5-methyl-4-isoxazolyl)-5(4H)-tetrazolinone,
1-(3-chloro-5-methyl-4-isoxazolyl)-5(4H)-tetrazolinone,
1-(5-methyl-4-isoxazolyl)-5(4H)-tetrazolinone,
1-(3-methyl-5-methoxy-4-isoxazolyl)-5(4H)-tetrazolinone,
1-(4-chloro-3-methyl-5-isoxazolyl)-5(4H)-tetrazolinone,
1-(3,4-dichloro-5-isoxazolyl)-5(4H)-tetrazolinone,
1-(5-cyclopropyl-4-isoxazolyl)-5(4H)-tetrazolinone,
1-(3-bromo-5-methyl-4-isoxazolyl)-5(4H)-tetrazolinone,
1-(4,5-dimethyl-3-isoxazolyl)-5(4H)-tetrazolinone,
1-(3-methyl-5-isopropyl-4-isoxazolyl)-5(4H)-tetrazolinone,
1-(3,4-dimethyl-5-isoxazolyl)-5(4H)-tetrazolinone,
1-(3-methyl-5-isoxazolyl)-5(4H)-tetrazolinone,
1-(4-chloro-5-methyl-3-isoxazolyl)-5(4H)-tetrazolinone,
1-(5-isoxazolyl)-5(4H)-tetrazolinone,
1-(5-methyl-3-isoxazolyl)-5(4H)-tetrazolinone,
1-(3,5-dimethyl-4-isoxazolyl)-5(4H)-tetrazolinone,
1-(4-thiazolyl)-5(4H)-tetrazolinone,
1-(5-thiazolyl)-5(4H)-tetrazolinone,
1-(2-thiazolyl)-5(4H)-tetrazolinone,
1-(4-methyl-2-thiazolyl)-5(4H)-tetrazolinone,
1-(2-chloro-4-methyl-5-thiazolyl)-5(4H)-tetrazolinone,
1-(2,4-dichloro-5-thiazolyl)-5(4H)-tetrazolinone,
1-(2,4-dimethyl-5-thiazolyl)-5(4H)-tetrazolinone,
1-(4-methyl-2-methylthio-5-thiazolyl)-5(4H)-tetrazolinone,
1-(2-methyl-4-thiazolyl)-5(4H)-tetrazolinone,
1-(2-methyl-4-trifluoromethyl-5-thiazolyl)-5(4H)-tetrazolinone,
1-(2,5-dichloro-4-thiazolyl)-5(4H)-tetrazolinone,
1-(2,5-dimethyl-4-thiazolyl)-5(4H)-tetrazolinone,
1-(4-methyl-2-methoxy-5-thiazolyl)-5(4H)-tetrazolinone,
1-(5-methyl-4-thiazolyl)-5(4H)-tetrazolinone,
1-(3-chloro-5-methoxy-4-isothiazolyl)-5(4H)-tetrazolinone,
1-(3,5-dichloro-4-isothiazolyl)-5(4H)-tetrazolinone,
1-(3-isothiazolyl)-5(4H)-tetrazolinone,
1-(3,5-dimethylthio-4-isothiazolyl)-5(4H)-tetrazolinone,
1-(4-methyl-5-isothiazolyl)-5(4H)-tetrazolinone,
1-(3-methyl-4-isothiazolyl)-5(4H)-tetrazolinone,
1-(5-isothiazolyl)-5(4H)-tetrazolinone,
1-(5-chloro-3-methyl-4-isothiazolyl)-5(4H)-tetrazolinone,
1-(3,5-dimethyl-4-isothiazolyl)-5(4H)-tetrazolinone,
1-(3,4-dimethyl-5-isothiazolyl)-5(4H)-tetrazolinone,
1-(3-methoxy-4-isothiazolyl)-5(4H)-tetrazolinone,
1-(3-methyl-5-isothiazolyl)-5(4H)-tetrazolinone,
1-(4,5-dichloro-3-isothiazolyl)-5(4H)-tetrazolinone,
1-(4-chloro-5-isothiazolyl)-5(4H)-tetrazolinone,
1-(4-chloro-3-methyl-5-isothiazolyl)-5(4H)-tetrazolinone,
1-(4-isothiazolyl)-5(4H)-tetrazolinone,
1-(1-methyl-2-imidazolyl)-5(4H)-tetrazolinone,
1-(1-benzyl-2-imidazolyl)-5(4H)-tetrazolinone,
1-(1-methyl-5-imidazolyl)-5(4H)-tetrazolinone,
1-(1-methyl-4-imidazolyl)-5(4H)-tetrazolinone,
1-(1,2-dimethyl-5-imidazolyl)-5(4H)-tetrazolinone,
1-(1,4-dimethyl-5-imidazolyl)-5(4H)-tetrazolinone,
1-(1,5-dimethyl-4-imidazolyl)-5(4H)-tetrazolinone,
1-(1-methyl-4-methylthio-5-imidazolyl)-5(4H)-tetrazolinone,
1-(1,3,5-trimethyl-4-pyrazolyl)-5(4H)-tetrazolinone,
1-(1,4-dimethyl-3-pyrazolyl)-5(4H)-tetrazolinone,
1-(4-chloro-1-methyl-5-pyrazolyl)-5(4H)-tetrazolinone,
1-(4-chloro-1-methyl-3-pyrazolyl)-5(4H)-tetrazolinone,
1-(1,3-dimethyl-4-pyrazolyl)-5(4H)-tetrazolinone,
1-(5-fluoro-1-methyl-3-trifluoromethyl-4-pyrazolyl)-5(4H)-tetrazolinone,
1-(3-chloro-1-methyl-4-pyrazolyl)-5(4H)-tetrazolinone,
1-(5-chloro-3-ethyl-1-methyl-4-pyrazolyl)-5(4H)-tetrazolinone,
1-(1,3-dimethyl-5-methoxy-4-pyrazolyl)-5(4H)-tetrazolinone,
1-(1,3-dimethyl-5-methylthio-4-pyrazolyl)-5(4H)-tetrazolinone,
1-(4-chloro-3-ethyl-1-methyl-5-pyrazolyl)-5(4H)-tetrazolinone,
1-(4-chloro-1-methyl-3-trifluoromethyl-5-pyrazolyl)-5(4H)-tetrazolinone,
1-(1-methyl-3-trifluoromethyl-5-pyrazolyl)-5(4H)-tetrazolinone,
1-(3,5-dichloro-1-methyl-4-pyrazolyl)-5(4H)-tetrazolinone,
1-(4-chloro-1,3-dimethyl-5-pyrazolyl)-5(4H)-tetrazolinone,
1-(1-methyl-3-methoxy-4-pyrazolyl)-5(4H)-tetrazolinone,
1-(1-methyl-3-trifluoromethyl-4-pyrazolyl)-5(4H)-tetrazolinone,
1-(1-methyl-5-methoxy-4-pyrazolyl)-5(4H)-tetrazolinone,
1-(3,5-dimethyl-1-ethyl-4-pyrazolyl)-5(4H)-tetrazolinone,
1-(5-chloro-1,3-dimethyl-4-pyrazolyl)-5(4H)-tetrazolinone,
1-(1,5-dimethyl-4-pyrazolyl)-5(4H)-tetrazolinone,
1-(4-chloro-1,3-dimethyl-5-pyrazolyl)-5(4H)-tetrazolinone,
1-(5-chloro-1-methyl-4-pyrazolyl)-5(4H)-tetrazolinone,
1-(1-methyl-5-pyrazolyl)-5(4H)-tetrazolinone,
1-(1,4-dimethyl-5-pyrazolyl)-5(4H)-tetrazolinone,
1-(1,3-dimethyl-5-pyrazolyl)-5(4H)-tetrazolinone,
1-(1-methyl-4-pyrazolyl)-5(4H)-tetrazolinone,
1-(4-chloro-1,5-dimethyl-3-pyrazolyl)-5(4H)-tetrazolinone,
1-(1-benzyl-3,5-dimethyl-4-pyrazolyl)-5(4H)-tetrazolinone,
1-(3-methyl-5-isothiazolyl)-5(4H)-tetrazolinone.

In the above-mentioned process a), the starting compounds of the formula (III) have the substituents defined hereinabove for $R^1$ and $R^2$, preferably the preferred substituents defined hereinabove for $R^1$ and $R^2$.

The compounds of the formula (III) are well known compounds in the field of organic chemistry, being sold as reagents and, as examples of said compounds, there may be mentioned the following compounds:
Diisopropylcarbamoylchloride and bromide,
Diethylcarbamoylchloride and bromide,
Dimethylcarbamoylchloride and bromide,
N-methyl-N-ethylcarbamoylchloride and bromide,
N-methyl-N-n-propylcarbamoylchloride and bromide,
N-methyl-N-isopropylcarbamoylchloride and bromide,
N-methyl-N-cyclopropylcarbamoylchloride and bromide,
N-methyl-N-s-butylcarbamoylchloride and bromide,
N-methyl-N-cyclopentylcarbamoylchloride and bromide,
N-methyl-N-cyclohexylcarbamoylchloride and bromide,
N-methyl-N-phenylcarbamoylchloride and bromide,
N-methyl-N-1-methyl-2-propenylcarbamoylchloride and bromide,
N-ethyl-N-n-propylcarbamoylchloride and bromide,
N-ethyl-N-isopropylcarbamoylchloride and bromide,
N-ethyl-N-cyclopropylcarbamoylchloride and bromide,
N-ethyl-N-s-butylcarbamoylchloride and bromide,
N-ethyl-N-cyclopentylcarbamoylchloride and bromide,
N-ethyl-N-cyclohexylcarbamoylchloride and bromide,
N-ethyl-N-phenylcarbamoylchloride and bromide,
N-n-propyl-N-isopropylcarbamoylchloride and bromide,
N-n-propyl-N-cyclopropylcarbamoylchloride and bromide,
N-n-propyl-N-s-butylcarbamoylchloride and bromide,
N-n-propyl-N-cyclopentylcarbamoylchloride and bromide,
N-n-propyl-N-cyclohexylcarbamoylchloride and bromide,
N-n-isopropyl-N-cyclohexylcarbamoylchloride and bromide,
N-isopropyl-N-phenylcarbamoylchloride and bromide,
N-isopropyl-N-allylcarbamoylchloride and bromide,
pyrrolidin-1-ylcarbonylchloride and bromide,
piperidinocarbonylchloride and bromide, morpholinocarbonylchloride and bromide,
2-methylpiperidinocarbonylchlride and bromide,
2,5-dimethylpyrrolidin-1-ylcarbonylchlride and bromide,
2,6-dimethylpiperidinocarbonylchloride and bromide,
2-methyl-1,2,3,4-tetrahydroquinolin-1-ylcarbonylchloride and bromide, and
perhydroquinolin-1-ylcarbonylchloride and bromide.

In the above-mentioned process b), in the starting compounds of formula (IV) the radicals $R^1$, $R^2$ and

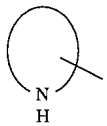

have the definitions and preferred definitions set forth hereinabove.

The compounds of the formula (IV) are also compounds of the present invention and can be synthesized by the above-mentioned process (a). As examples of said compounds, there may be mentioned the following compounds:

1-(1-benzyl-2,5-dimethyl-3-pyrrolyl)-4-(N,N-dimethylcarbamoyl)-5(4H)-tetrazolinone,
1-(1-benzyl-2-imidazolyl)-4-(N,N-dimethylcarbamoyl)-5(4H)-tetrazolinone,
1-(1-benzyl-3,5-dimethyl-4-pyrazolyl)-4-(N,N-dimethylcarbamoyl)-5(4H)-tetrazolinone,
1-(1-benzyl-2,5-dimethyl-3-pyrrolyl)-4-(N-ethyl-N-isopropylcarbamoyl)-5(4H)-tetrazolinone,
1-(1-benzyl-2-imidazolyl)-4-(N-ethyl-N-isopropylcarbamoyl)-5(4H)-tetrazolinone,
1-(1-benzyl-3,5-dimethyl-4-pyrazolyl)-4-(N-ethyl-N-isopropylcarbamoyl)-5(4H)-tetrazoline,
1-(1-benzyl-2,5-dimethyl-3-pyrrolyl)-4-(N-ethyl-N-cyclohexylcarbamoyl)-5(4H)-tetrazolinone,
1-(1-benzyl-2-imidazolyl)-4-(N-ethyl-N-cyclohexylcarbamoyl)-5(4)-tetrazolinone,
1-(1-benzyl-3,5-dimethyl-4-pyrazolyl)-4-(N-ethyl-N-cyclohexylcarbamoyl)-5(4H)-tetrazolinone.

In carrying out the process a) mentioned above, use may be made, as a suitable diluent, of any inert organic solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as diethyl ether, methyl ethyl ether, di-iso-propyl ether, dibutyl ether, dioxane, dimethoxyethane (DME), tetrahydrofuran (THF), diethylene glycol dimethyl ether (DGM) and the like; nitriles such as acetonitrile, propionitrile, and the like; acid amides such as dimethyl formamide (DMF), dimethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane and the like; and bases such as pyridine.

The above-mentioned process a) may be carried out in the presence of an acid binder. As the acid binder there may be mentioned, for example, inorganic bases including hydroxides, carbonates, bicarbonates, and alcolates of alkali metals, such as sodium hydrogen carbonate, potassium hydrogen carbonate, sodium carbonate, potassium carbonate, lithium hydroxide, sodium hydroxide, potassium hydroxide, calcium hydroxide, potassium tert-butoxide and the like; and inorganic amides of alkali metals such as lithium amide, sodium amides, potassium amide and the like; and organic bases including tertiary amines, dialkylaminoanilines and pyridines, such as trimethylamine, triethylamine, 1,1,4,4-tetramethylethylenediamine (TMEDA), N,N-dimethylaniline, N,N-diethylaniline, pyridine, 4-dimethylamino pyridine (DMAP), 1,4-diazabicyclo[2,2,2]octane (DABCO), 1,8-diazabicyclo-[5,4,0]undec-7-ene (DBU), and the like. Furthermore, use may be made of organic lithium compounds such as methyl lithium, n-butyl lithium, sec-butyl lithium, tert-butyl lithium, phenyl lithium, dimethyl copper lithium, lithium diisopropyl amide, lithium cyclohexylisopropyl amide, lithium dicyclohexyl amide n-butyl lithium.DABCO, n-butyl lithium.DBU, n-butyl lithium.TMEDA and the like.

In the above-mentioned process a), the reaction temperature can be varied within a substantially, wide range. In general, the reaction is carried out at a temperature of from about −30° C. to about 200° C., preferably from about −20° C. to about 130° C.

Further, the reaction is preferably carried out under normal pressure, although it it also possible to employ a higher or reduced pressure.

When the above-mentioned process a) is carried out, use may be made, for example, of 1 to 1.5 mols of the compound of the formula (III) in a diluent such as toluene per mol of the compound of the formula (II) in the presence of 1 to 1.5 mols of the acid binder to obtain the desired compound.

In carrying out the above-mentioned process b), the reduction conditions are described in Organic Reaction, Vol. VIII, page 263, 1953, John Wiley & Sons, Inc. Pub.

In carrying out the process b) mentioned above, use may be made, as a suitable diluent, of any inert organic solvent.

Examples of such diluents are water; aliphatic, cycloaliphatic and aromatic hydrocarbons, such as pentane, hexane, cyclohexane, petroleum ether, ligroin, benzene, toluene, xylene, and the like; ethers such as ethyl ether, methyl ethyl ether, isopropyl ether, butyl ether, dioxane, dimethoxyethane (DME), tetrahydrofuran (THF), diethylene glycol dimethyl ether (DGM) and the like; alcohols such as methanol, ethanol, isopropanol, butanol, ethylene glycol and the like; acid amides such as dimethyl formamide (DMF), dimethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane and the like.

The process (b) is carried out in the presence of a palladium catalyst and there may be mentioned those carried on activated carbon, silica, alumina, barium sulfate, calcium carbonate, etc.

In the process b), the reaction temperature can be varied within a substantially wide range. In general, the reaction is carried out at a temperature of from about −70° C. to about 200° C., preferably. from about 0° C. to about 120° C.

Further, the reaction is preferably carried out under a normal pressure, although it is also possible to employ a higher or reduced pressure.

When the above-mentioned process b) is carried out, use may be made, for example, of 1 mol to 100 moles of hydrogen gas in a diluent such as ethanol per mol of the compound of the formula (IV) in the presence of palladium-charcoal to obtain the desired compound.

The active compounds according to the present invention can be used as herbicides for controlling weeds.

By the term "weeds", in the broadest sense, are meant all plants which grow in locations where they are not desired.

The compounds according to the present invention act as either selective or non-selective herbicides depending on their concentration to be employed.

The active compounds according to the present invention may be used, for example, in the case of the following plants:

Dicotyledon weeds such as mustard (Sinapis), cress (Lepidium), bed straw (Galium), chickweed (Stellaria), goosefoot (Chenopodium), annual nettle (Urtica), groundsell (Senecio), pigweed (Amaranthus), purslane (Portulaca), cocklebur (Xanthium), morning glory (Ipomoea), knotweed (Polygonum), ragweed (Ambrosia), spear thistle (Cirsium), sow thistle (Sonchus), egg plant, potato (Solanum), field cress (Rorippa), deadnettle (Lamium), speedwell (Veronica), thornapple (Datura), violet (Viola), hemp-nettle (Galeopals), poppy (Papaver), knapweed (Centsurea), gallant soldier (Galinsoga), toothcup (Rotala) and false pimpernel (Lindernia);

dicotyledon cultured such as cotton (Gossypium), soya bean (Glycine), beet (Beta), carrot (Daucus), bean (Phaseolus), pea (Pisum), potato (Solanum), flax (Linum), sweet potato (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cucurbita);

monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), ryegrass (Lolium), cheat (Bromus), oats (Avena), flatsedge (Cyperus), sorghum (Sorghum), quackgrass (Agropyron), monochoria (Monochoria), fimbristylis (Fimbristylis), arrowhead (Sagittaris), spikerush (Eleocharis) bulrush (Scirpus), paspalum (Paspalum), (Ischaemum), redtop (Agrostis), meadow foxtail (Alopecurus), and Bermuda grass (Cynodon); and monocotyledon cultured such as rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the present invention is in no way restricted only to the above-mentioned plants but extends to other plants similarly.

Depending on the concentration, the active compounds can be used for non-selective control of weeds, for example, on industrial terrain and railway tracks and on paths and squares with and without trees. Equally, the active compounds can be employed for combating weeds in perennial cultures, for example, forestry plantings, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective controlling of weeds in annual cultures.

The active compounds according to the present invention can be converted into customary formulations, such as solutions, wettable powders, emulsions, suspensions, powders, foams, pastes, granules, aerosols, natural and synthetic materials impregnated with active compounds, micro-capsules, coating compositions for use on seeds, and formulations used with burning equipment, such as fumigating cartridges, fumigating cans and fumigating coils, as well as ULV (cold mist and warm mist) formulations.

These formulations may be prepared in a manner known in themselves, for example, by mixing the active compounds with extenders, that is to say, liquid or liquefied gaseous or solid diluents or carriers, optionally with the use of surface-active agents, that is to say, emulsifying agents and/or dispersing agents and/or foam-forming agents. In the case of the use of water as an extender, organic solvents can, for example, also be used as auxiliary solvents.

As liquid diluents or carriers there may be mentioned, in general, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as yell as their ethers and esters, ketones, such as acetone, methylethyl ketone, methylisobutyl ketone or cyclohexanone, or strongly polar solvents, such as dimethylformamide and dimethylsulfoxide, as well as water.

By liquefied gaseous diluents or carriers are meant liquids which would be gaseous at normal temperature and under normal pressure, such as, for example, butane, propane, nitrogen gas and carbon dioxide, and aerosol propellants, such as halogenated hydrocarbons.

As solid diluents there may be used ground natural minerals, such as kaoline, clays, talc, chalk, quartz, attapulgite, montmorillonite or diatomaceous earth, and ground synthetic minerals, such as highly-dispersed silicic acid, alumina and silicates.

As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example, alkylaryl polyglycol ethers, alkyl sulfonates, alkyl sulfates, aryl sulfonates as well as albumin hydrolysis products.

Dispersing agents include, for example, lignin sulfite waste liquors and methylcellulose.

Adhesives such as carboxymethylcellulose and natural and synthetic polymers such as, for example, gum arabic, polyvinyl alcohol and polyvinyl acetate, may be used in the formulations (for example, dusting agent, granules or emulsions).

It is possible to use colorants such as inorganic pigments, for example, iron oxide, titanium oxide and Prussian Blue, and organic dyestuffs, such as alizarin dyestuffs, azo dyestuffs or metal phthalocyanine dyestuffs, and to use a trace amount of nutrients, such as iron, manganese, boron, copper, cobalt, molybdenum or zinc and their salts.

The formulations in general may contain from 0.1 to 95 percent by weight of the actives compounds, preferably from 0.5 to 90 percent by weight.

The active compounds according to the present invention can be used as such or in the form of herbicidal compositions for controlling weeds. It is also possible to combine the present active compounds with other known herbicidal agents. The resulting mixture can be handled either in the form of ready-to-use formulations or in the form of other formulations which are generally called tank-mix.

As known herbicidal agents that can be combined with the present active compounds there may be mentioned:

For weed controlling in cereal plant cultivation:

4-amino-6-(1,1-dimethylethyl)-3-ethylthio-1,2,4-triazin-5(4H)-one, 1-amino-6-ethylthio-3-(2,2-dimethylpropyl)-1,3,5-triazin-2,4(1H,3H)-dione and N-(2-benzothiazolyl)-N,N'-dimethylurea, etc.

For weed controlling in sugar cane cultivation:

4-amino-3-methyl-6-phenyl-1,2,4-triazin-5(4H)-one, etc.
For weed controlling in soybean cultivation:

4-amino-6-(1,1-dimethylethyl)-3-methylthio-1,2,4-triazin-5(4H)-one, etc.

Surprisingly, several mixture formulations of the present active compounds also exhibit synergistic effects.

The present active compounds can be used as such, as their formulations such as in the forms of ready-to-use preparations, emulsions, suspensions, dusting agents, pastes and granules or as the use forms prepared therefrom by further dilution thereof.

They may be used in the customary manner, for example, by watering, spraying, atomizing, granule application, etc.

The present active compounds can be used either in the pre-, or post-emergence period of plants. It is also possible to apply the active compounds into soil before the seeds of plants are sown.

The concentration of the active compound used can vary over a—wide range. It depends essentially on the nature of the desired effect. In general, the amounts used as a herbicide are from about 0.001 to about 10 kg of the active compound per hectare, preferably from about 0.01 to about 5 kg/ha.

The production and the use of the active compounds according to the present invention will be illustrated by the following working examples. It should be noted that the scope of the invention is not limited only to the technical contents of the Examples.

EXAMPLE 1

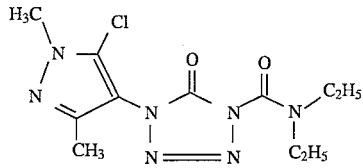

(Compound No. 1)

1-(5-Chloro-1,3-dimethyl-4-pyrazolyl)-5(4H)-tetrazolinone (1.2 g), diethylcarbamoylchloride (0.95 g) and 4-dimethylaminopyridine (0.86 g) were suspended in toluene (15 ml). The resulting suspension was heated under reflux for 6 hours. The salts were removed by filtration, and the solvent was distilled off under reduced pressure. The resulting residue was subjected to silica gel chromatography (chlorofrom) so that-1-(5-chloro-1,3-dimethyl-4-pyrazolyl)-4-(N, N-diethylcarbamoyl)-5(4H)-tetrazolinone (1.7 g) was obtained $n_D^{20}$=1.5085 Table 3 below shows other compounds of the invention which may be obtained by the same method as above.

TABLE 3-1

| Compound No. | $R^3$ | $R^1$ | $R^2$ | Physical constant |
|---|---|---|---|---|
| 2 | Q6 | ethyl | cyclohexyl | $n_D^{20} = 1.5250$ |
| 3 | Q6 | ethyl | isopropyl | $n_D^{20} = 1.5137$ |
| 4 | Q6 | methyl | isoproyl | $n_D^{20} = 1.5235$ |
| 5 | Q9 | ethyl | cyclohexyl | $n_D^{20} = 1.5282$ |
| 6 | Q9 | ethyl | isopropyl | $n_D^{20} = 1.5089$ |
| 7 | Q9 | methyl | isopropyl | mp = 84–87° C. |
| 8 | Q10 | ethyl | cyclohexyl | $n_D^{20} = 1.5232$ |
| 9 | Q10 | ethyl | ethyl | $n_D^{20} = 1.5193$ |
| 10 | Q10 | ethyl | isopropyl | $n_D^{20} = 1.5131$ |
| 11 | Q10 | methyl | isopropyl | $n_D^{20} = 1.5189$ |
| 12 | Q11 | ethyl | cyclohexyl | $n_D^{20} = 1.5588$ |
| 13 | Q11 | ethyl | ethyl | mp = 74–75° C. |
| 14 | Q12 | ethyl | ethyl | mp = 51–52° C. |
| 15 | Q26 | ethyl | ethyl | 10% DMF Solution |
| 16 | Q29 | ethyl | ethyl | mp = 70–71° C. |
| 17 | Q29 | isoproyl | ethyl | $n_D^{20} = 1.5089$ |
| 18 | Q32 | ethyl | ethyl | $n_D^{20} = 1.5682$ |
| 19 | Q33 | ethyl | ethyl | $n_D^{20} = 1.5281$ |
| 20 | Q33 | ethyl | isopropyl | $n_D^{20} = 1.5272$ |
| 21 | Q47 | allyl | isopropyl | $n_D^{20} = 1.5125$ |
| 22 | Q47 | ethyl | cyclohexyl | $n_D^{20} = 1.5183$ |
| 23 | Q47 | ethyl | ethyl | $n_D^{20} = 1.5043$ |
| 24 | Q47 | ethyl | isopropyl | $n_D^{20} = 1.5012$ |
| 25 | Q47 | isopropyl | isopropyl | mp = 110–114° C. |
| 26 | Q47 | methoxy | isopropyl | $n_D^{20} = 1.4989$ |
| 27 | Q47 | methyl | isopropyl | $n_D^{20} = 1.5097$ |
| 28 | Q47 | methyl | methyl | mp = 122–124° C. |
| 29 | Q50 | ethyl | ethyl | $n_D^{20} = 1.5199$ |
| 30 | Q50 | phenyl | isopropyl | mp = 95.5–99° C. |
| 31 | Q75 | methyl | isopropyl | mp = 67–70° C. |
| 32 | Q94 | ethyl | ethyl | mp = 94–97° C. |
| 33 | Q107 | ethyl | cyclohexyl | $n_D^{20} = 1.5141$ |
| 34 | Q107 | ethyl | ethyl | $n_D^{20} = 1.5146$ |
| 35 | Q107 | ethyl | isopropyl | $n_D^{20} = 1.5164$ |
| 36 | Q107 | isopropyl | isopropyl | $n_D^{20} = 1.5180$ |
| 37 | Q107 | methyl | isopropyl | mp = 103–108° C. |
| 38 | Q108 | ethyl | cyclohexyl | $n_D^{20} = 1.5292$ |

TABLE 3-1-continued

| Compound No. | R³ | R¹ | R² | Physical constant |
|---|---|---|---|---|
| 39 | Q108 | ethyl | ethyl | $n_D^{20} = 1.5207$ |
| 40 | Q108 | ethyl | isopropyl | $n_D^{20} = 1.5270$ |
| 41 | Q108 | methyl | isopropyl | $n_D^{20} = 1.5258$ |
| 42 | Q111 | ethyl | cyclohexyl | mp = 106–107.5° C. |
| 43 | Q111 | ethyl | ethyl | mp = 67.5–69° C. |
| 44 | Q111 | ethyl | isopropyl | mp = 106.5–108° C. |
| 45 | Q111 | methyl | isopropyl | mp = 113–114° C. |
| 46 | Q114 | ethyl | ethyl | $n_D^{20} = 1.5246$ |
| 47 | Q114 | ethyl | isopropyl | $n_D^{20} = 1.5204$ |
| 48 | Q114 | ethyl | cyclohexyl | $n_D^{20} = 1.5278$ |
| 49 | Q114 | methyl | isopropyl | mp = 67–73° C. |
| 50 | Q115 | ethyl | ethyl | $n_D^{20} = 1.5279$ |
| 51 | Q116 | ethyl | ethyl | $n_D^{20} = 1.5257$ |
| 52 | Q116 | ethyl | isopropyl | $n_D^{20} = 1.5300$ |
| 53 | Q116 | methyl | isopropyl | $n_D^{20} = 1.5292$ |
| 54 | Q123 | ethyl | cyclohexyl | $n_D^{20} = 1.1940$ |
| 55 | Q123 | ethyl | ethyl | $n_D^{20} = 1.488$ |
| 56 | Q123 | ethyl | isopropyl | $n_D^{20} = 1.4844$ |
| 57 | Q123 | methyl | isopropyl | $n_D^{20} = 1.4900$ |
| 58 | Q126 | allyl | allyl | $n_D^{20} = 1.5375$ |
| 59 | Q126 | allyl | isopropyl | $n_D^{20} = 1.5269$ |
| 60 | Q126 | ethyl | cyclohexyl | $n_D^{20} = 1.5317$ |
| 61 | Q126 | ethyl | n-butyl | $n_D^{20} = 1.5181$ |
| 62 | Q126 | ethyl | n-propyl | $n_D^{20} = 1.5235$ |
| 63 | Q126 | isopropyl | 2-chloro-2-propenyl | $n_D^{20} = 1.5256$ |
| 64 | Q126 | isopropyl | 2-methyl-2-propenyl | $n_D^{20} = 1.5170$ |
| 65 | Q126 | isopropyl | ethyl | $n_D^{20} = 1.5168$ |
| 66 | Q126 | isopropyl | isopropyl | $n_D^{20} = 1.5132$ |
| 67 | Q126 | isopropyl | phenyl | mp = 87–90° C. |
| 68 | Q126 | isopropyl | propargyl | $n_D^{20} = 1.5229$ |
| 69 | Q126 | methoxy | cyclohexyl | $n_D^{20} = 1.5260$ |
| 70 | Q126 | methoxy | isopropyl | $n_D^{20} = 1.5010$ |
| 71 | Q126 | methyl | allyl | mp = 85.5–85° C. |
| 72 | Q126 | methyl | cyclohexyl | $n_D^{20} = 1.5220$ |
| 73 | Q126 | methyl | ethyl | $n_D^{20} = 1.5354$ |
| 74 | Q126 | methyl | isobutyl | $n_D^{20} = 1.5159$ |
| 75 | Q126 | methyl | isopropyl | mp = 109–110° C. |
| 76 | Q126 | methyl | methyl | mp = 130–131° C. |
| 77 | Q126 | methyl | n-propyl | $n_D^{20} = 1.5219$ |
| 78 | Q126 | methyl | propargyl | mp = 158–159° C. |
| 79 | Q126 | n-propyl | n-propyl | $n_D^{20} = 1.5251$ |
| 80 | Q128 | ethyl | cyclohexyl | $n_D^{20} = 1.5236$ |
| 81 | Q128 | ethyl | ethyl | $n_D^{20} = 1.5240$ |
| 82 | Q128 | ethyl | isopropyl | $n_D^{20} = 1.5200$ |
| 83 | Q128 | isopropyl | isopropyl | $n_D^{20} = 1.5089$ |
| 84 | Q129 | ethyl | cyclohexyl | $n_D^{20} = 1.5352$ |
| 85 | Q129 | ethyl | ethyl | mp = 90–93° C. |
| 86 | Q129 | ethyl | isopropyl | $n_D^{20} = 1.5308$ |
| 87 | Q129 | methyl | isopropyl | $n_D^{20} = 1.5360$ |
| 88 | Q132 | ethyl | ethyl | mp = 102–105° C. |
| 89 | Q134 | ethyl | cyclohexyl | $n_D^{20} = 1.5219$ |
| 90 | Q134 | ethyl | ethyl | mp = 99–101° C. |
| 91 | Q134 | ethyl | isopropyl | $n_D^{20} = 1.5165$ |
| 92 | Q134 | isoproyl | isopropyl | $n_D^{20} = 1.5116$ |
| 93 | Q134 | methyl | isopropyl | mp = 105–110° C. |
| 94 | Q134 | methyl | methyl | mp = 140.5–141.5° C. |
| 95 | Q139 | ethyl | ethyl | $n_D^{20} = 1.5455$ |
| 96 | Q155 | ethyl | ethyl | mp = 140–141° C. |
| 97 | Q155 | methyl | isopropyl | mp = 193–194° C. |
| 98 | Q156 | ethyl | cyclohexyl | $n_D^{20} = 1.5199$ |
| 99 | Q156 | ethyl | ethyl | $n_D^{20} = 1.5220$ |
| 100 | Q156 | ethyl | isopropyl | $n_D^{20} = 1.5179$ |
| 101 | Q156 | methyl | isopropyl | $n_D^{20} = 1.5209$ |
| 102 | Q157 | ethyl | isopropyl | $n_D^{20} = 1.4995$ |
| 103 | Q157 | methyl | isopropyl | $n_D^{20} = 1.5050$ |
| 104 | Q163 | ethyl | ethyl | $n_D^{20} = 1.4767$ |
| 105 | Q163 | ethyl | isopropyl | $n_D^{20} = 1.4852$ |
| 106 | Q163 | methyl | isopropyl | $n_D^{20} = 1.4911$ |
| 107 | Q164 | ethyl | cyclohexyl | $n_D^{20} = 1.4924$ |
| 108 | Q164 | ethyl | ethyl | $n_D^{20} = 1.4850$ |

TABLE 3-1-continued

| Compound No. | R³ | R¹ | R² | Physical constant |
|---|---|---|---|---|
| 109 | Q164 | ethyl | isopropyl | $n_D^{20} = 1.4821$ |
| 110 | Q164 | methyl | isopropyl | $n_D^{20} = 1.4839$ |
| 111 | Q171 | methyl | isopropyl | mp = 102–103° C. |
| 112 | Q171 | ethyl | isopropyl | $n_D^{20} = 1.4969$ |
| 113 | Q174 | ethyl | ethyl | $n_D^{20} = 1.5201$ |
| 114 | Q174 | ethyl | isopropyl | $n_D^{20} = 1.5161$ |
| 115 | Q174 | methyl | isopropyl | mp = 80–82° C. |
| 116 | Q175 | ethyl | cyclohexyl | $n_D^{20} = 1.5057$ |
| 117 | Q175 | ethyl | ethyl | $n_D^{20} = 1.4990$ |
| 118 | Q175 | ethyl | isopropyl | $n_D^{20} = 1.4962$ |
| 119 | Q175 | methyl | isopropyl | mp = 88–90° C. |

Compounds according to the invention wherein—R¹ and R² form, together with the nitrogen to which R¹ and R² are bonded, a heterocyclic ring are shown in Table 3–7.

TABLE 3-7

| Compound No. | R³ | R¹ and R² | Physical constant |
|---|---|---|---|
| 120 | Q126 | 2,6-dimethyl-piperidino | $n_D^{20} = 1.5285$ |
| 121 | Q126 | 2,5-dimethyl-pyrazolidin-1-yl | $n_D^{20} = 1.5301$ |
| 122 | Q126 | 2,5-dimethyl-3-pyrazolin-1-yl | $n_D^{20} = 1.5305$ |
| 123 | Q126 | 5-methyl-2-pyrazolin-1-yl | mp = 145–147° C. |
| 124 | Q126 | perhydroindol-1-yl | $n_D^{20} = 1.5442$ |
| 125 | Q126 | 2-methyl-piperidin-1-yl | $n_D^{20} = 1.5278$ |
| 126 | Q126 | decahydroquinolin-1-yl | $n_D^{20} = 1.5306$ |

EXAMPLE 2

Synthesis of starting material:

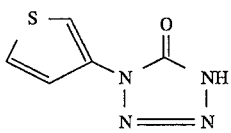

3,5-Dimethyl-4-isoxazolylcarboxylic acid (14.1 g) and thionyl chloride (15.0 g) were mixed and the resulting mixture was heated under reflux for 20 hours. The excess thionyl chloride was distilled off under reduced pressure, and trimethylsilyl azide (30.0 g) was added to the residue thus obtained. The resulting mixture was heated under reflux for 24 hours, and the excess trimethylsilyl azide was distilled off under reduced pressure and then methanol (30 ml) was added to the residue thus obtained. Thereafter, the methanol was distilled off, and the resultant residue was subjected to silica gel chromatography, using chloroform: ethanol=15:1, so that 1-(3,5-dimethyl-4-isoxazolyl)-5(4H)-tetrazolinone (10.5 g) was obtained. m.p. 191.5°–193° C. (decomposition).

The compounds prepared according to a process similar to the above-mentioned synthesis are shown below.

1-(5-isoxazolyl)-5(4H)-tetrazolinone, mp=145°–146.5° C. (decomposition), 1-(5-methyl-3-isoxazolyl)-5(4H)-tetrazolinone, mp=193°–196° C. (decomposition), 1-(2,4-dimethyl-3-furyl)-5(4H)-tetrazolinone, mp=139.5°–142° C. (decomposition), 1-(2-methyl-3-furyl)-5(4H)-tetrazolinone, mp=128°–129.5° C. (decomposition), 1-(2,5-dimethyl-3-furyl)-5(4H)-tetrazolinone, mp=109.5°–110.5° C. (decomposition).

EXAMPLE 3

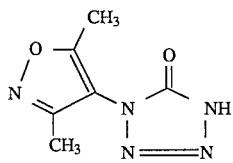

3-Thienyl isocyanate (2.5 g) was mixed with trimethylsilyl azide (4 g), and the resulting mixture was heated under reflux for 20 hours. The excess trimethylsilyl azide was distilled off under reduced pressure, and methanol was added to the residue thus obtained. Thereafter, the methanol was distilled off, and the resultant residue was subjected to silica gel column chromatography, using chloroform: ethanol=15:1, so that 1-(3-thienyl)-5(4H)-tetrazolinone (3.0 g) was obtained. m.p. 139°–141° C.

EXAMPLE 4

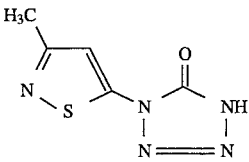

Anhydrous aluminum chloride (8.6 g) was added to dimethylformamide (50 ml) under ice-cooling and the resulting mixture was stirred for 15 minutes. Sodium azide (3.8 g) was further added to the mixture and the mixture obtained was stirred for 15 minutes. After said stirring, phenyl N-(3-methyl-5-isothiazolyl)carbamate (6.3 g) was added to the mixture, and the resulting mixture was stirred at 80° C. for 10 hours. The reaction solution was added to the mixture of sodium nitrite (4 g), water (500 ml) and ice (250 g). After acidifying with 10% hydrochloric acid solution (until coloring the potassium iodide starch paper), the solution was extracted by ethyl acetate, and then the ethyl acetate phase obtained was dried with sodium sulfate. Thereafter solvent was distilled off under reduced pressure, the resultant residue was subjected to silica gel column chromatography, so that 1-(3-methyl-5-isothiazolyl)-5(4H)-tetrazolinone was obtained (0.2 g). m.p. 160°–161.5° C. (decomposition).

EXAMPLE 5

Synthesis Example 4:

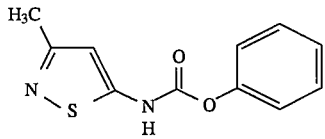

5-Amino-3-methyl isothiazole (15 g) was dissolved in pyridine (150 ml) and phenylchloroformate (15.7 g) was added dropwise to the resulting solution under cooling at 0° C. After stirring at 0° C. for 2 hours, the solvent was distilled off under reduced pressure, and water was added to the residue thus obtained. Deposited crystals were obtained by filtration and dried by air to obtain phenyl N-(3-methyl-5-isothiazolyl) carbamate (19.9 g). m.p. 186°–188.5° C.

The compound prepared according to a process similar to the above-mentioned synthesis is shown below. phenyl N-(2-thiazolyl) carbamate, m.p.=108.5°–181.5° C.

Biological tests

EXAMPLE 6

(Pre-emergence soil treatment test on upland weeds)

Formulation of Active Compounds

Carrier: 5 parts by weight of acetone

Emulsifier: 1 part by weight of benzyloxy polyglycol ether

To prepare suitable formulations, 1 part by weight of each of the active compounds was mixed with the above-stated amounts of the carrier and the emulsifier, and the resulting emulsifiable concentrate was then diluted with water to the desired concentrations.

Test Procedure

In a greenhouse, a number of test pots each having an area of 120 cm² were charged with soil taken—from a cultivated field. Seeds of barnyard grass and wild amaranth (Amaranthus blitum) were sown onto the soil surfaces in the respective test pots and each of the thus sown soil surfaces was covered with a soil layer to 1 cm depth. Predetermined dosages of the active compounds of formulations prepared as mentioned above were uniformly sprayed onto the soil surface in the respective test pots.

Four weeks after the spraying of the diluted solution of the compound formulation, the degrees of the herbicidal effect on the weeds were determined. The resulting herbicidal effects deriving therefrom were related according to the following assessment:

Completely killed:100%

Condition equivalent to non-treated pots:0%

In the above-mentioned test, for example,—compounds Nos. 1, 6, 13, 16, 18, 20, 22, 25, 27, 28, 29, 30, 34, 35, 37, 39, 40, 41, 57, 63, 75, 76, 82, 93, 99, 106, 113, 115, 120 and 121 according to the present invention showed 100% herbicidal activity against barnyard grass and wild amaranth at a dosage of 1.0 kg/ha.

EXAMPLE 7

(Post-emergence foliage treatment on upland weeds)

Test Procedure

In a greenhouse, a number of test pots each having an area of 120 cm² were charged with soil taken from a cultivated field. Seeds of barnyard grass and wild amaranth (Amaranthus blitum) were sown onto the soil surfaces in the respective test pots and each of the thus sown soil surfaces was covered with a soil layer to 1 cm depth. After ten days said sowing (average 2 leaf stage of weeds), predetermined dosages of the active compound of formulations prepared as in Example 6 were uniformly sprayed onto the foliage portions of the test plants in the respective test pots.

Three weeks after the spraying of the diluted solution of the active compound formulations, the degrees of the herbicidal activity on the weeds were determined.

In the above-mentioned test, for example, compounds Nos. 1, 6, 22, 23, 27, 28, 29, 35, 40 and 75 according to the present invention showed 100% herbicidal activity against barnyard grass and wild amaranth at a dosage of 1.0 kg/ha.

It will be understood that the specification and examples are illustrative but not limitative of the present invention and that other embodiments within the spirit and scope of the invention will suggest themselves to those skilled in the art.

We claim:

1. A substituted tetrazolinone of the formula

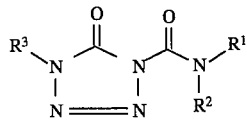

wherein

R¹ is alkyl, haloalkyl, cycloalkyl, alkenyl, haloalkenyl, alkynyl, alkoxy or phenyl which is optionally substituted, R² is alkyl, haloalkyl, cycloalkyl, alkenyl, haloalkenyl, alkynyl, alkoxy, or phenyl of which is optionally substituted, or R¹ and R² form, together with the nitrogen atom to which they are bonded, a 5- or 6-membered heterocyclic ring, optionally fused to a carboxylic ring and optionally substituted by $C_{1-4}$ alkyl, and R³ is a 5-membered heterocyclic radical containing at least one hetero atom selected from the group consisting of nitrogen, oxygen and sulfur, optionally substituted by at least one substituent selected form the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkyl-sulfonyl and $C_{3-8}$ cycloalkyl.

2. A compound according to claim 1, in which

R¹ is $C_{1-4}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynyl, $C_{1-6}$ alkoxy or phenyl, $R^2$ is $C_{1-6}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynyl, $C_{1-6}$ alkoxy or phenyl, or $R^1$ and $R^2$ form, together with the nitrogen atom to which they are bonded, a 5- or 6-membered heterocyclic ring, optionally containing a further hetero atom selected from the group consisting of nitrogen, oxygen and sulfur and said heterocyclic ring is optionally fused to a cyclohexyl or phenyl ring and is optionally substituted by methyl, $R^3$ is a 5-membered heterocyclic ring selected from the group consisting of furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl and 1,2,4-triazolyl, and said 5-membered heterocyclic ring is optionally and independently substituted by substituents selected form the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkyl-sulfonyl and $C_{3-8}$ cycloalkyl.

3. A compound according to claim 1, in which, $R^1$ is $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl, $C_{1-4}$ alkoxy or phenyl, and $R^2$ is $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl, $C_{1-4}$ alkoxy or phenyl, or $R^1$ and $R^2$ form, together with the nitrogen atom to which $R^1$ and $R^2$ are bonded, pyrrolidin-1-yl, 2,5-dimethylpyrrolidin-1-yl, pyrrolin-1-yl, 2,5-dimethyl-3-pyrrolin-1-yl, 5-methyl-2-pyrazolin-1-yl, piperidino, 2-methylpiperidino, 2,6-di-methylpiperidino, piperazin-1-yl, morpholino, 1,2,3,4-tetrahydro-quinolin-1-yl, 2-methyl-1,2,3,4-tetrahydroquinolin-1-yl, perhydroindin-1-yl or perhydroquinolin-1-yl, $R^3$ is a 5-membered heterocyclic ring selected from the group consisting of furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl and 1,2,4-triazolyl, said 5-membered heterocyclic being optionally and independently substituted by at least one substituent selected from the group consisting of fluorine, chlorine, bromine, methyl, ethyl, isopropyl, propyl, (n-iso-, sec-, tert-)butyl, cyclopropyl, cyclohexyl, cyclopentyl, methoxy, ethoxy, isopropoxy, propoxy, trifluoromethyl, fluoromethoxy, methylthio, ethylthio, propyplthio, isopropylthio, n-(iso-, sec-, tert-)butylthio, methyl-sulfonyl, ethyl-sulfonyl, n-propyl-sulfonyl, benzyl, phenyl and chlorophenyl.

4. A compound according to claim 1, wherein such compound is 1-(3,5-dimethyl-4-isoxazolyl)-4-(N-isopropyl-N-phenylcarbamoyl)-5(4H)-tetrazolinone of the formula

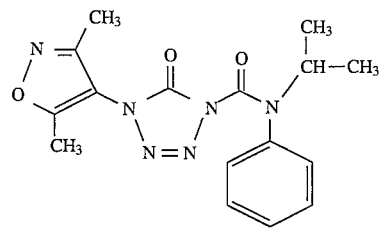

5. A compound according to claim 1, wherein such compound is 1-(4-chloro-1,5-dimethyl-3-pyrazolyl)-4-(N-isopropyl-N-methylcarbamoyl)-5-(4H)-tetrazolinone of the formula

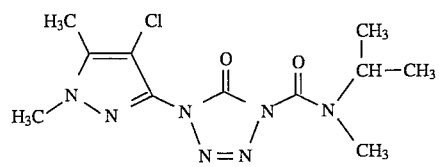

6. A herbicidal composition comprising a herbicidally effective amount of a compound according to claim 1 and a diluent.

7. A method of combatting unwanted vegetation which comprises applying to such vegetation or to a locus from which it is desired to exclude such vegetation a herbicidally effective amount of a compound according to claim 1 and a diluent.

8. The method according to claim 7, wherein such compounds is 1-(3,5-dimethyl-4-isoxazolyl)-4-(N-isopropyl-N-phenylcarbamoyl)-5(4H)-tetrazolinone, and 1-(4-chloro-1,5-dimethyl-3-pyrazolyl)-4-(N-isopropyl-N-methylcarbamoyl)-5(4H)-tetrazolinone.

9. A tetrazolinone of the formula

(II)

wherein $R^3$ is a 5-membered heterocyclic ring comprising at least one hetero atom selected from the group consisting of nitrogen, oxygen, and sulfur and said 5-membered heterocyclic ring is optionally and independently substituted by at least one substituent selected from the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $c_{1-4}$ alkylthio, $C_{1-4}$ alkyl-sulfonyl and $C_{3-8}$ cycloalkyl.

10. A compound according to claim 9, in which $R^3$ is a 5-membered heterocyclic ring selected from the group consisting of furyl, thienyl, pyrrolyl, imadazolyl, pyrazolyl, thiazolyl, isothiazolyl, oxazolyl, isoxazolyl tetrazolyl, 1,2,3-oxadiazolyl, 1,2,4-oxadiazolyl, 1,2,5-oxadiazolyl, 1,3,4-oxadiazolyl, 1,2,3-thia-diazolyl, 1,2,4-thiadiazolyl, 1,2,5-thiadiazolyl, 1,3,4-thiadiazolyl, 1,2,3-triazolyl and 1,2,4-triazolyl, and said 5-membered heterocyclic ring is optionally and independently substituted by substituents selected from the group consisting of halogen, benzyl, phenyl, halogen-substituted phenyl, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ alkyl-sulfonyl and $C_{3-8}$ cycloalkyl.

11. A compound according to claim 9, in which

R³ is a 5-membered heterocyclic ring selected from the group consisting of furyl, thienyl, pyrrolyl, imidazolyl, pyrazolyl, thiazolyl, isothiazolyl, oxazolyl, isoxazolyl, tetrazolyl, 1,2,3-oxadiazolyl, 1,2,4-oxadiazolyl, 1,2,5-oxadiazolyl, 1,3,4-oxadiazolyl, 1,2,3-thiadiazolyl, 1,2, 4-thiadiazolyl, 1,2,5-thiadiazolyl, 1,3,4-thiadiazolyl, 1,2,3-triazolyl, and 1,2,4-triazolyl, and said 5-membered heterocyclic ring is optionally and independently substituted by substituents selected from the group consisting of fluorine, chlorine, bromine, methyl, ethyl, isopropyl, propyl, n-(iso-, sec-, tert-)butyl, cyclopropyl, cyclohexyl, cyclopentyl, methoxy, ethoxy, isopropoxy, propoxy, trifluoromethyl, fluoromethoxy, methylthio, ethylthio, propylthio, isopropylthio, n-(iso, sec-, tert-) butylthio, methyl-sulfonyl, ethyl-sulfonyl, n-propyl-sulfonyl, benzyl, phenyl and chlorophenyl.

12. A process for the preparation of a tetrazolinone

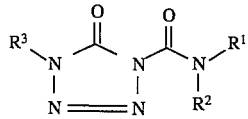   (I)

according to claim 1, which comprises (a) reacting a compound of the formula

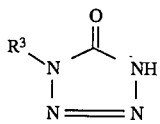   (II)

with a compound of the formula

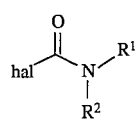   (III)

wherein hal is bromine or chlorine, in the presence of acid-binder, and in the presence of an inert solvent, or (b) if R³ represents 5-membered heterocyclic ring including the radical

N
|
H so that R³ is

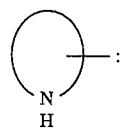

reducing a compound of the formula

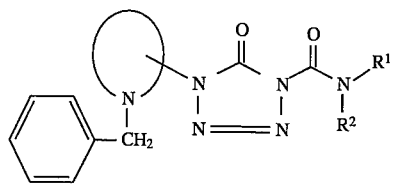   (IV)

optionally in the presence of catalyst, and in the presence of an inert solvent.

* * * * *